(12) United States Patent
Kawabata et al.

(10) Patent No.: US 8,987,358 B2
(45) Date of Patent: Mar. 24, 2015

(54) COMPOUND INCLUDING ORGANOPOLYSILOXANE OR SILSESQUIOXANE SKELETON HAVING ISOCYANURIC SKELETON, EPOXY GROUP AND SIH GROUP, THERMOSETTING RESIN COMPOSITION CONTAINING THE COMPOUND AS ADHESION-IMPARTING AGENT, HARDENED MATERIAL AND SEALING AGENT FOR OPTICAL SEMICONDUCTOR

(75) Inventors: Kiichi Kawabata, Kumamoto (JP); Akio Tajima, Kumamoto (JP); Takashi Matsuo, Kumamoto (JP); Yoshiko Watanabe, Kumamoto (JP); Koichi Ayama, Tokyo (JP)

(73) Assignee: JNC Corporation, Tokyo (JP)

( * ) Notice: Subject to any disclaimer, the term of this patent is extended or adjusted under 35 U.S.C. 154(b) by 0 days.

(21) Appl. No.: 14/130,499

(22) PCT Filed: Jun. 28, 2012

(86) PCT No.: PCT/JP2012/066540
§ 371 (c)(1),
(2), (4) Date: Jan. 29, 2014

(87) PCT Pub. No.: WO2013/005633
PCT Pub. Date: Jan. 10, 2013

(65) Prior Publication Data
US 2014/0148536 A1 May 29, 2014

(30) Foreign Application Priority Data
Jul. 4, 2011 (JP) .................................. 2011-148476

(51) Int. Cl.
*H01L 33/56* (2010.01)
*C07F 7/21* (2006.01)
(Continued)

(52) U.S. Cl.
CPC . *H01L 33/56* (2013.01); *C07F 7/21* (2013.01); *C08G 77/54* (2013.01); *C08G 77/388* (2013.01); *C08G 59/306* (2013.01); *C09D 163/00* (2013.01)

USPC .............................. 524/101; 524/493; 528/31

(58) Field of Classification Search
None
See application file for complete search history.

(56) References Cited

U.S. PATENT DOCUMENTS 8,273,843 B2 * 9/2012 Tajima et al. .................... 528/31
2006/0052623 A1 * 3/2006 Yoshida et al. ............... 556/450
(Continued)

FOREIGN PATENT DOCUMENTS

JP 2004-099751 4/2004
JP 2008-150506 7/2008
(Continued)

OTHER PUBLICATIONS

"International Search Report (Form PCT/ISA/210)", mailed on Oct. 16, 2012, with English translation thereof, p. 1-p. 4.
(Continued)

*Primary Examiner* — Robert S Loewe
(74) *Attorney, Agent, or Firm* — Jianq Chyun IP Office

(57) ABSTRACT

The invention provides an adhesion-imparting agent having heat-resistant transparency and a high refractive index best suited for an addition hardening type composition including a reaction product of silsesquioxane and organopolysiloxane. The invention relates to a compound obtained by allowing a hydrosilylation addition reaction of (A), (B), and when necessary, (C) as described below, and a compound including an organopolysiloxane or silsesquioxane skeleton including as an essential component an isocyanuric ring skeleton and an epoxy group, and having an SiH group residue: (A) a compound including an organopolysiloxane or silsesquioxane skeleton and having three or more SiH groups in one molecule; (B) an epoxy derivative having one aliphatic unsaturated group in one molecule; and (C) organopolysiloxane having two alkenyl groups in one molecule, and having a number average molecular weight of 100 to 500,000, or an isocyanurate compound having two alkenyl groups in one molecule.

10 Claims, 21 Drawing Sheets

(51) Int. Cl.
*C08G 77/54* (2006.01)
*C08G 77/388* (2006.01)
*C08G 59/30* (2006.01)
*C09D 163/00* (2006.01)

(56) References Cited

U.S. PATENT DOCUMENTS

| | | | |
|---|---|---|---|
| 2009/0163652 A1* | 6/2009 | Tajima et al. | 524/612 |
| 2009/0203822 A1 | 8/2009 | Shiobara et al. | |
| 2010/0125116 A1 | 5/2010 | Shiobara et al. | |
| 2012/0149819 A1 | 6/2012 | Inoki et al. | |
| 2013/0096249 A1* | 4/2013 | Kawabata et al. | 524/547 |

FOREIGN PATENT DOCUMENTS

| | | |
|---|---|---|
| JP | 2009-203258 | 9/2009 |
| JP | 2009-275206 | 11/2009 |
| JP | 2010-138380 | 6/2010 |
| JP | 4541842 | 9/2010 |
| JP | 2010-280766 | 12/2010 |
| JP | 2011-057755 | 3/2011 |
| WO | 2009034998 | 3/2009 |
| WO | 2011102470 | 8/2011 |
| WO | 2011145638 | 11/2011 |

OTHER PUBLICATIONS

"International Preliminary Report on Patentability of PCT application"; this report contains the following items :Form PCT/IB/373, PCT/ISA237(cover sheet), PCT/ISA237(Box No. I),PCT/ISA237(Box No. V), issued on Jan. 7, 2014, which is English translation of "Written Opinion of the International Searching Authority", p. 1-p. 10.

Wu et al., "Synthesis and characterization of a functional polyhedral oligomeric silsesquioxane and its flame retardancy in epoxy resin", Progress in Organic Coatings, Apr. 2009, p. 490-p. 497, vol. 65.

* cited by examiner

COMPOUND INCLUDING ORGANOPOLYSILOXANE OR SILSESQUIOXANE SKELETON HAVING ISOCYANURIC SKELETON, EPOXY GROUP AND SIH GROUP, THERMOSETTING RESIN COMPOSITION CONTAINING THE COMPOUND AS ADHESION-IMPARTING AGENT, HARDENED MATERIAL AND SEALING AGENT FOR OPTICAL SEMICONDUCTOR

CROSS-REFERENCE TO RELATED APPLICATION

This application is a 371 application of an international PCT application serial no. PCT/JP2012/066540, filed on Jun. 28, 2012, which claims the priority benefit of Japan application no. 2011-148476, filed on Jul. 4, 2011. The entirety of each of the above-mentioned patent applications is hereby incorporated by reference herein and made a part of this specification.

TECHNICAL FIELD

The invention relates to a compound including an organopolysiloxane or silsesquioxane skeleton having an isocyanuric skeleton, an epoxy group and an SiH group, and in particular, to an adhesion-imparting agent suitable for a thermosetting resin composition containing thermosetting resin including silsesquioxane and organopolysiloxane and having both heat-resistant transparency and a high refractive index. Moreover, the invention provides a thermosetting resin composition containing the compound as an adhesion-imparting agent, a hardened material or a coating film obtained by hardening the thermosetting resin composition, a composition for an optical semiconductor, the composition containing the thermosetting resin composition, and an optical semiconductor device including the composition for the optical semiconductor.

BACKGROUND ART

A white LED has been applied to a backlight of TV, illumination or the like. Heat generation from an LED package becomes non-negligible in connection with achieving significant power. In the case where epoxy resin is used for a seating material, avoidance of yellowing due to the heat generation becomes quite difficult, and therefore silicone resin has been used for a seating material of white LED in place of the epoxy resin. The silicone resin used for the LED is broadly classified into two kinds including phenyl silicone resin and methyl silicone resin.

The phenyl silicone resin that is generally used has a satisfactory value for a refractive index, and while the resin is superior to the epoxy resin in resistance to thermal yellowing, is not enough to address achieving significant power of LED. The methyl silicone resin has, while the resin is superb in resistance to thermal yellowing, a low refractive index, and therefore has a poor light-extraction efficiency of LED.

Therefore, an eager wish has been expressed for a sealing material that can address achieving significant power of white LED and has both a high refractive index and good heat-resistant transparency, and a thermosetting resin composition used therefor.

Patent literature No. 1 discloses a thermosetting resin composition using silsesquioxane having excellent heat resistance and transparency and having both heat-resistant transparency and a high refractive index. The thermosetting resin composition comprises a polymer of organopolysiloxane and imperfect condensation structure silsesquioxane as commonly referred to as a double decker. Double-decker silsesquioxane is ordinarily different from structure of polysilsesquioxane having random structure obtained from an alkoxysilane hydrolytic condensation reaction. The composition has controlled structure, and therefore has high heat resistance.

Meanwhile, with regard to a thermoset material due to a combination of silsesquioxane and organopolysiloxane, a ratio of double-decker silsesquioxane being a hard component to an organopolysiloxane being a soft component is changed in compounding the thermosetting resin, thereby theoretically allowing adjustment of hardness of a hardened material from a rubbery material to a lenticular material.

Moreover, heat resistance has been recently required for an LED package itself, and in place of ordinary nylon-based polyphthalamide resin that has been frequently used so far, polyamide resin (PA9T: heat-resistant grade of polyamide) or a liquid crystal polymer (LCP) having excellent heat resistance has been adopted as various kinds of package materials.

In general, as a technique for improving adhesion, a silane coupling agent, or a compound prepared by introducing an epoxy group or an alkoxysilyl group into tetracyclosiloxane is known, but an effect is small to heat-resistant resin such as PA9T or LCP as described above. Moreover, attention has been recently attracted to a compound having an isocyanurate skeleton as such a material allowing an improvement in adhesion with the heat-resistant resin.

Patent literature No. 2 discloses as an adhesive an organopolysiloxane composition in which isocyanurate having an epoxy group is of addition hardening type. Moreover, patent literature No. 3 discloses a composition in which an alkoxysilyl group is further introduced into an isocyanuric ring skeleton having an epoxy group.

Patent literature No. 4 discloses isocyanuric skeleton-containing polysiloxane prepared by allowing an addition reaction of diallyl monoglycidyl isocyanurateto to Si—H-containing polysiloxane. Moreover, patent literature No. 5 presents isocyanuric skeleton-containing polysiloxane prepared by allowing an addition reaction of monoallyl glycidyl isocyanurate to polysiloxane having an SiH group in a side chain.

CITATION LIST

Patent Literature

Patent literature No. 1: JP 2010-280766 A.
Patent literature No. 2: JP 4541842 B.
Patent literature No. 3: JP 2011-57755 A.
Patent literature No. 4: JP 2008-150506 A.
Patent literature No. 5: JP 2004-99751 A.

SUMMARY OF INVENTION

Technical Problem

A thermosetting resin composition according to patent literature No. 1 has a problem of weakened adhesion performance if double-decker silsesquioxane content decreases. Moreover, the composition has a problem of too high hardness of the resin even with improved adhesion performance, if silsesquioxane content is high, resulting in allowing no stress relaxation to easily cause peeling in a thermal shock test such as a heat cycle test.

Furthermore, a reaction product of silsesquioxane and organopolysiloxane has had a problem of poor adhesion with heat-resistant resin such as PA9T or LCP. Accordingly, an eager wish has been expressed for a material allowing overcoming of the disadvantage described above without adversely affecting an advantage of resistance to thermal yellowing and a high refractive index of thermosetting resin by the reaction product of silsesquioxane and organopolysiloxane.

Moreover, the compositions according to patent literature Nos. 2 and 3 have poor compatibility with a composition of a polymer of silsesquioxane and organopolysiloxane being a main agent of a thermosetting composition used in the invention, and in order to maintain transparency, an addition amount is restricted, and an effect is not produced.

Furthermore, in patent literature No. 4, the isocyanuric ring-containing polysiloxane is used as a main agent of a hardening resin composition, and therefore heat-resistant transparency is far from satisfactory. Moreover, the polysiloxane is a block copolymer of organopolysiloxane and an isocyanuric ring skeleton, and therefore an effect of an isocyanuric ring being an adhesion-imparting agent is hard to be produced.

Furthermore, in patent literature No. 5, isocyanuric ring-containing polysiloxane is used as an epoxy-hardened material for sealing a semiconductor, is not suitable for use in which transparency is required, and is quite difficult to be used as a material for an optical semiconductor. Moreover, isocyanuric ring-containing polysiloxane described in patent literature No. 5 has glycidyl isocyanurate in a side chain of polysiloxane, and therefore is considered that an adhesion effect due to an isocyanuric ring is easily developed. However, the polysiloxane has no SiH group, and therefore lacks performance as an adhesion material of a hardened composition of a hydrosilyl addition hardening type.

Accordingly, the invention provides an adhesion-imparting agent best suited for an addition hardening type composition that has both heat-resistant transparency and a high refractive index, and includes a reaction product of silsesquioxane and organopolysiloxane. In particular, the invention provides an adhesion-imparting agent having good adhesion with heat-resistant polyamide, a liquid crystal polymer, and also a silver surface.

Solution to Problem

The present inventors have diligently continued to conduct study so as to solve the problem. As a result, the present inventors have found that the problem can be solved upon using a compound having specific chemical structure, including an organopolysiloxane or silsesquioxane skeleton including as an essential component an isocyanuric ring skeleton and an epoxy group, and having an SiH-group residue, and thus have completed the invention.

More specifically, the invention is as described below.

Item 1. A compound obtained by allowing a hydrosilylation addition reaction of (A) and (B), and when necessary (C) as described below, the compound including an organopolysiloxane or silsesquioxane skeleton including as an essential component an isocyanuric ring skeleton and an epoxy group, and having an SiH-group residue:
(A) a compound including an organopolysiloxane or silsesquioxane skeleton, and having three or more SiH groups in one molecule;
(B) an epoxy derivative having one aliphatic unsaturated group in one molecule; and
(C) organopolysiloxane having two alkenyl groups in one molecule and having a number average molecular weight of 100 to 500,000, or an isocyanuric ring skeleton-containing compound having two alkenyl groups in one molecule.

Item 2. A compound obtained by allowing a hydrosilylation addition reaction of (A) and (B), and when necessary (C) as described below, the compound including a silsesquioxane skeleton including as an essential component an isocyanuric ring skeleton and an epoxy group, and having an SiH-group residue:
(A) a compound including a silsesquioxane skeleton, and having three or more SiH groups in one molecule;
(B) an epoxy derivative having one aliphatic unsaturated group in one molecule; and
(C) organopolysiloxane having two alkenyl groups in one molecule and having a number average molecular weight of 100 to 500,000, or an isocyanuric ring skeleton-containing compound having two alkenyl groups in one molecule.

Item 3. The compound including the organopolysiloxane or silsesquioxane skeleton including as the essential component the isocyanuric ring skeleton and the epoxy group, and having the SiH-group residue according to item 1 or 2, obtained by allowing a hydrosilylation addition reaction of (A) and (B), and when necessary (C), and also (D) as described below:
(D) a compound having an aliphatic unsaturated group, and having an alkoxysilyl group, a trialkylsilyl group, or a silyl group having a vinyl group.

Item 4. The compound including the silsesquioxane skeleton including as the essential component the isocyanuric ring skeleton and the epoxy group, and having the SiH group residue according to any one of items 1 to 3, being a compound represented by general formula (1):

Formula 1

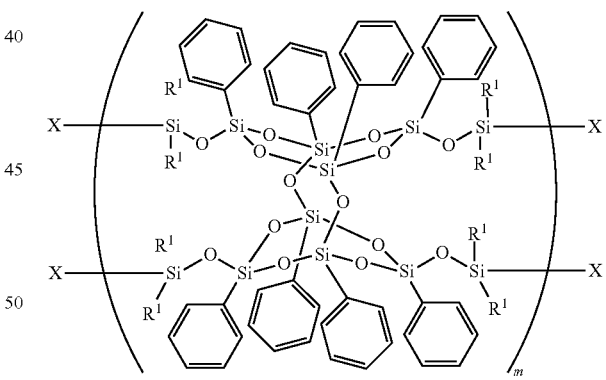

(1)

In formula (1), X is each independent a group represented by formula (a), formula (b-i), formula (b-ii), formula (b-iii), formula (c-i), formula (c-ii), formula (c-iii) or formula (d) below, and with regard to the number of groups per one molecule of compound represented by formula (1) (per one molecule on average of the compound when the compound is a mixture in which a ratio of the group represented by formula (a), a ratio of the group represented by formula (b-i) and a ratio of the group represented by formula (b-ii) and formula (b-iii) are different), in the case where the number of groups represented by formula (a) is taken as A, the number of groups represented by formula (b-i), formula (b-ii) or formula (b-iii) is taken as B, the number of groups represented by formula (c-i), formula (c-ii) or formula (c-iii) is taken as C, and the number of groups represented by formula (d-i), formula (d-ii) or formula (d-iii) is taken as D, expressions: $A+B+2C+D=4$, $0.1 \leq A \leq 3.5$, $0.1 \leq B \leq 3.5$, $0 \leq 2C \leq 2.0$, and $0 \leq D \leq 3.0$ hold.

$R^1$ is each independently a group selected from alkyl having 1 to 4 carbons, cyclopentyl and cyclohexyl, and m is 1 to 100.

Formula 2

—H (a)

Formula 3

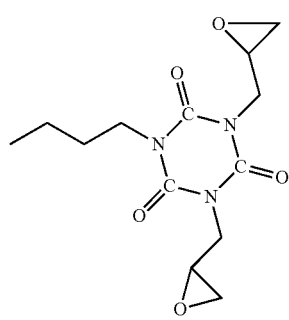

(b-i)

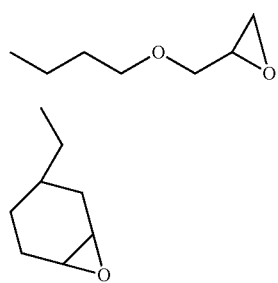

(b-ii)

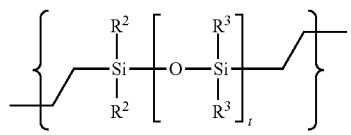

(b-iii)

Formula 4

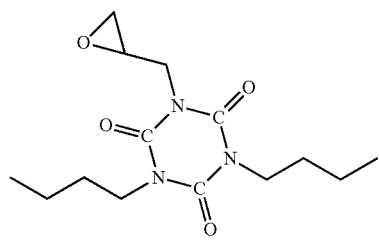

(c-i)

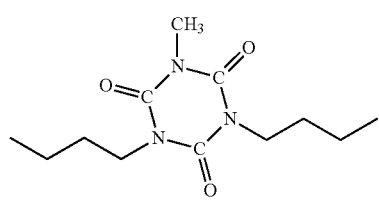

(c-ii)

(c-iii)

In formula (c-i), $R^2$ and $R^3$ are each independently a group selected from alkyl having 1 to 4 carbons, cyclopentyl, cyclohexyl and phenyl, and t is the number of repetitions of —OSi$(R^3)_2$—, and is a mean value satisfying 1 to 100.

Formula 5

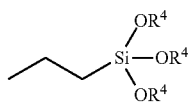

(d-i)

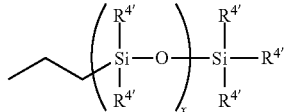

(d-ii)

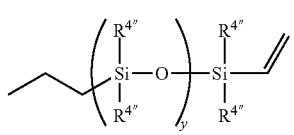

(d-iii)

In formulas (d-i) to (d-iii), $R^4$, $R^{4'}$ and $R^{4''}$ are each independently a group selected from methyl, ethyl, butyl and isopropyl, x is the number of repetitions of —OSi$(R^{4'})_2$—, and is a mean value satisfying 1 to 20, and y is the number of repetitions of —OSi$(R^{4''})_2$—, and is a mean value satisfying 1 to 20.

Item 5. A compound obtained by allowing a hydrosilylation addition reaction of (A) and (B), and when necessary (C) as described below, the compound including an organopolysiloxane skeleton including as an essential component an isocyanuric ring skeleton and an epoxy group, and having an SiH-group residue:

(A) a compound including an organopolysiloxane skeleton, and having three or more SiH groups in one molecule;

(B) an epoxy derivative having one aliphatic unsaturated group in one molecule; and (C) organopolysiloxane having two alkenyl groups in one molecule and having a number average molecular weight of 100 to 500,000, or an isocyanuric ring skeleton-containing compound having two alkenyl groups in one molecule.

Item 6. The compound including the organopolysiloxane skeleton including as the essential component the isocyanuric ring skeleton and the epoxy group, and having the SiH-group residue according to item 1, 3 or 5, represented by general formula (2):

Formula 6

$$Y-\underset{R^5}{\overset{R^5}{Si}}-\left[O-\underset{R^5}{\overset{R^5}{Si}}\right]_p\left[O-\underset{R^5}{\overset{Y}{Si}}\right]_q O-\underset{R^5}{\overset{R^5}{Si}}-Y \quad (2)$$

In formula (2), Y is each independently a group represented by formula (a), formula (b-i), formula (b-ii), formula (b-iii) or formula (d), and when a ratio of the group represented by formula (a) per the group represented by Y is taken as A, a ratio of the group represented by formula (b-i), formula (b-ii) or formula (b-iii) is taken as B, and a ratio of the group represented by formula (d) is taken as D, in one molecule of the compound represented by formula (2), expressions: $A+B+D=4$, $0.1 \leq A \leq 0.7$, $0.05 \leq B \leq 0.6$, and $0.01 \leq D \leq 0.6$ hold.

In addition, among B, the group represented by formula (b-i) is an essential ingredient, and the group represented by formula (b-ii), and the group represented by formula (b-iii) are arbitrary.

$R^5$ is each independently a group selected from alkyl having 1 to 4 carbons, cyclopentyl and cyclohexyl, aryl having 6 to 14 carbons and arylalkyl having 7 to 24 carbons. Then, p and q are the number of 1 to 100, respectively.

Formula 7

(a)
—H

Formula 8

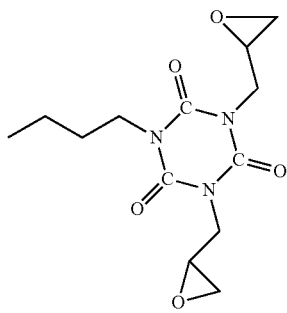
(b-i)

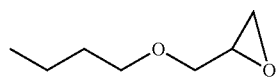
(b-ii)

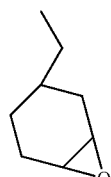
(b-iii)

Formula 9

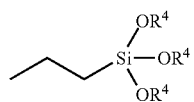
(d)

In formula (d), $R^4$ is each independently a group selected from methyl, ethyl, butyl and isopropyl.

Item 7. A thermosetting resin composition containing (I) to (IV) below:

(I) a reaction product of double-decker silsesquioxane and organopolysiloxane, and thermosetting resin having an SiH group or both an SiH group and an alkenyl group;

(II) thermosetting resin that has two or more alkenyl groups and is an organosiloxane compound that may also include a silsesquioxane skeleton;

(III) the compound according to any one of items 1 to 6 as an adhesion-imparting agent; and (IV) a Pt catalyst.

Item 8. The thermosetting resin composition according to item 7, wherein the thermosetting resin (I) is a compound represented by formula (I) below:

Formula 10

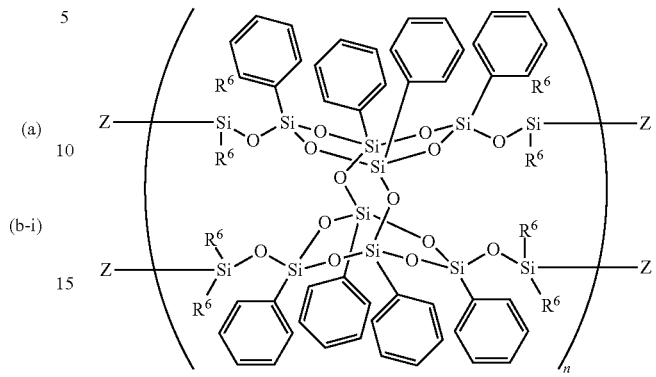
(I)

In formula (I), Z is each independently a group represented by formula (Z-i), formula (Z-ii) or formula (Z-iii) below, and with regard to the number of groups when the number of groups per one molecule of the compound represented by formula (I) (per one molecule on average of the compound being a mixture of compounds in which a ratio of the group represented by formula (Z-i), a ratio of the group represented by formula (Z-ii) and a ratio of the group represented by formula (Z-iii) are different), in the case where the number of groups represented by formula (Z-i) is taken as e, the number of groups represented by formula (Z-ii) is taken as f, and the number of groups represented by formula (Z-iii) is taken as g, expressions: $e+2f+g=4$, $1.0 \le e \le 3.0$, $0 \le 2f \le 2.0$, and $0 \le g \le 2.0$ hold.

$R^6$ is each independently a group selected from alkyl having 1 to 4 carbons, cyclopentyl and cyclohexyl, and n is 1 to 100.

Formula 11

(Z-i)
—H

Formula 12

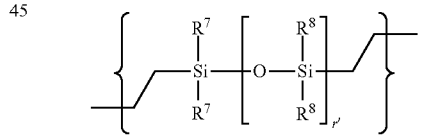
(Z-ii)

In formula (Z-ii), $R^7$ and $R^8$ are each independently a group selected from alkyl having 1 to 4 carbons, cyclopentyl, cyclohexyl and phenyl, r' is the number of repetitions of —OSi($R^8$)$_2$—, and r' is a mean value satisfying 2 to 100.

Formula 13

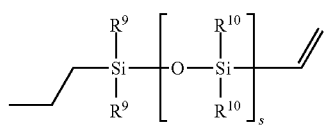
(Z-iii)

In formula (Z-iii), $R^9$ and $R^{10}$ are each independently a group selected from alkyl having 1 to 4 carbons, cyclopentyl, cyclohexyl and phenyl, s is the number of repetitions of —OSi(R$^{10}$)$_2$—, and s is a mean value satisfying 2 to 50.

Item 9. The thermosetting resin composition according to item 7 or 8, containing the thermosetting resin (I) in a ratio of 40 to 95% by mass, the thermosetting resin (II) in a ratio of 0.1 to 50% by mass, the compound (III) in a ratio of 0.01 to 15.0% by mass, and the Pt catalyst (IV) in a ratio of 0.0001 ppm to 10 ppm, based on the total amount of the thermosetting resin composition.

Item 10. The thermosetting resin composition according to any one of items 7 to 9, wherein at least one of silica or a phosphor is further dispersed thereinto.

Item 11. A hardened material, obtained by hardening the thermosetting resin composition according to any one of items 7 to 10.

Item 12. A coating film, obtained by hardening the thermosetting resin composition according to any one of items 7 to 10.

Item 13. A composition for an optical semiconductor, containing the thermosetting resin composition according to any one of items 7 to 10.

Item 14. An optical semiconductor device, including the composition for the optical semiconductor according to item 13 as a sealing agent.

Advantageous Effects of Invention

When a compound including an organopolysiloxane or silsesquioxane skeleton including as an essential component an isocyanuric ring skeleton and an epoxy group, and having an SiH group residue according to the invention is incorporated as an adhesion-imparting agent into a thermosetting resin composition containing thermosetting resin by a reaction product of silsesquioxane and organopolysiloxane, a hardened material obtained by hardening the thermosetting resin composition presents, without adversely affecting an advantage of a high refractive index and excellent resistance to thermal yellowing being an advantage of thermosetting resin by a reaction product of silsesquioxane and organopolysiloxane, excellent adhesion properties with heat-resistant resin such as PA9T or LCP to which adhesion has been difficult. Furthermore, an optical semiconductor apparatus sealed with the hardened material can be an optical semiconductor apparatus that can be withstand a severe reliability test.

DESCRIPTION OF EMBODIMENTS

Figure 1:
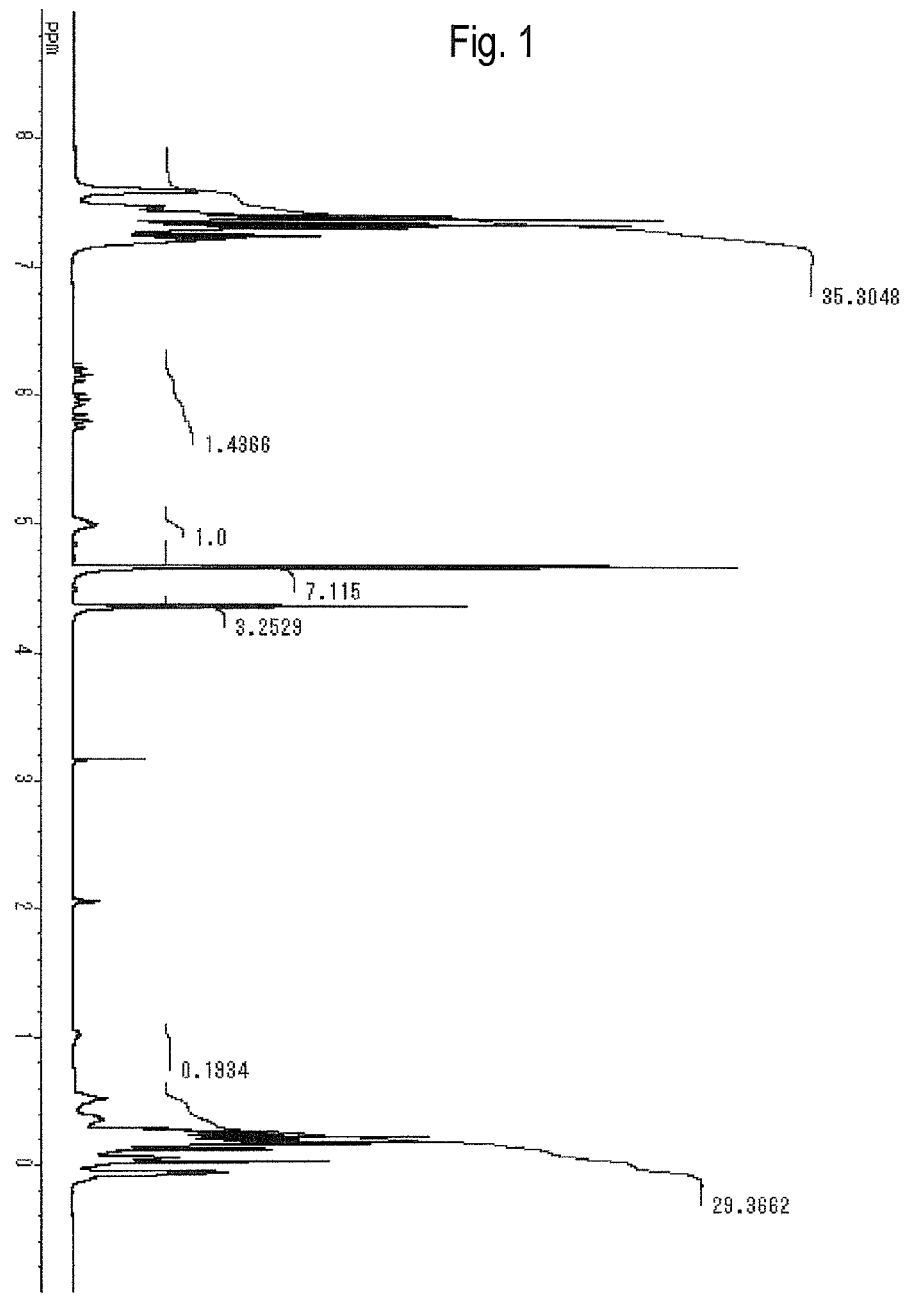
FIG. 1 shows a $^1$H-NMR chart of silsesquioxane derivative base polymer 1 obtained in Synthesis Example 1.

Terms used in the invention are explained.

A compound represented by formula (1) may be occasionally expressed as compound (1). Any other compound represented by any other formula may be occasionally abbreviated and referred to.

"Arbitrary" in the invention means that not only a position but also the number is arbitrary. Then, an expression "arbitrary A may be replaced by B or C" means inclusion of a case where at least one of A is replaced by B and a case where at least one of A is replaced by C, and also a case where at least one of A is replaced by B, and simultaneously at least one of other A is replaced by C.

In addition, a setup in which arbitrary —CH$_2$— in alkyl or alkylene may be replaced by —O— does not include a case where all of plurality of consecutive —CH$_2$— are replaced by —O—.

In Examples, data displayed on an electronic balance are expressed using g (gram) being a mass unit. Then, % by mass or a mass ratio includes data based on such a numeric value.

A compound including an organopolysiloxane or silsesquioxane skeleton including as an essential component an isocyanuric ring skeleton and an epoxy group, and having an SiH group residue according to the invention (hereinafter, referred to also as a compound of the invention) is obtained by a hydrosilylation addition reaction of (A) and (B) below, or a hydrosilylation addition reaction of (A), (B) and (C) below:

(A) a compound including an organopolysiloxane or silsesquioxane skeleton and having three or more SiH groups in one molecule;

(B) an epoxy derivative having one aliphatic unsaturated group in one molecule; and (C) organopolysiloxane having two alkenyl groups in one molecule and having a number average molecular weight of 100 to 500,000, or an isocyanuric ring-containing compound having two alkenyl groups in one molecule.

In the case where the isocyanuric ring skeleton exists in (B) described above, whether the hydrosilylation addition reaction of (C) is allowed with (A) and (B) as described above may be arbitrary. In the case where the isocyanuric ring skeleton does not exist in epoxy derivative (B) described above, the hydrosilylation addition reaction of (C) described above is allowed with (A) and (B).

In the case where the compound of (A) described above includes the silsesquioxane skeleton, the hydrosilylation addition reaction of organopolysiloxane having two alkenyl groups in one molecule and having the number average molecular weight of 100 to 500,000 as (C) described above is preferably allowed together with (A) and (B) described above.

Moreover, the compound of the invention may be obtained by allowing the hydrosilylation addition reaction of (A) and (B) described above, and when necessary, (C) and also (D). The hydrosilylation addition reaction of (A) and (B) described above, and when necessary (C) and (D) is allowed, thereby allowing an improvement of adhesion of the compound of the invention with a metal, and also an improvement of compatibility with resin:

(D) a compound having an aliphatic unsaturated group and having an alkoxysilyl group, a trialkylsilyl group or a vinyl group.

1. (A) Compound Including an Organopolysiloxane or Silsesquioxane Skeleton, and Having Three or More SiH Groups in One Molecule 1-1. Compound (A) Including a Silsesquioxane Skeleton, and Having Three or More SiH Groups in One Molecule Specific examples of compound (A) including the silsesquioxane skeleton, and having three or more SiH groups in one molecule include compounds represented by formulas (A-1) to (A-5) below.

Formula 14

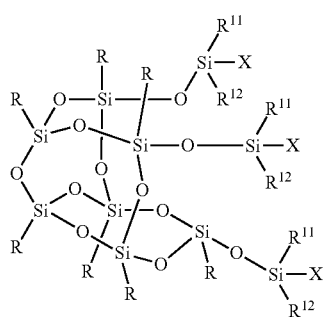

(A-1)

Formula 15

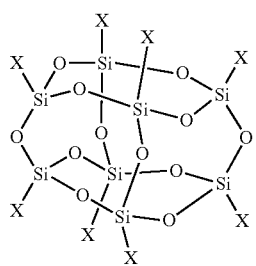

(A-2)

Formula 16

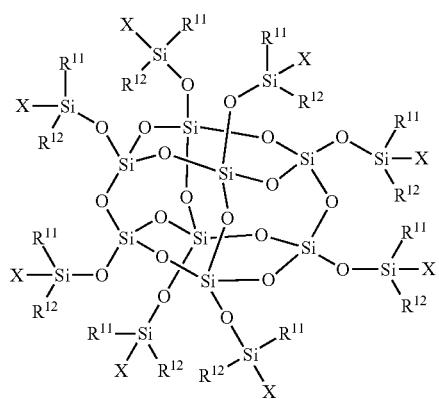

(A-3)

Formula 17

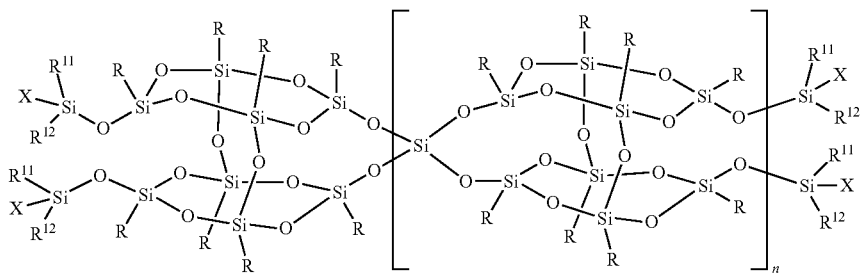

(A-4)

Formula 18

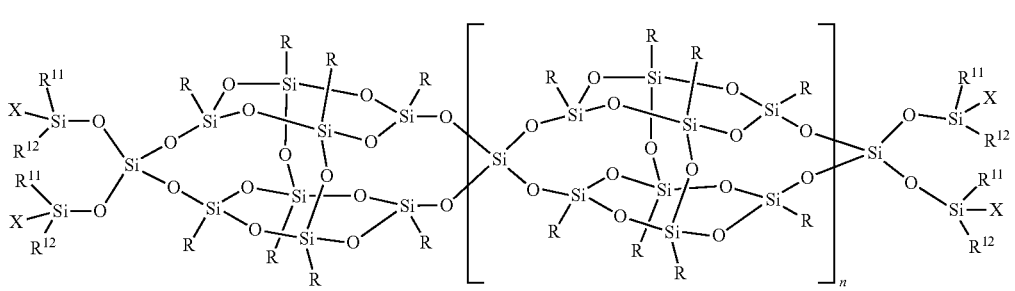

(A-5)

In formula (A-1), formula (A-4) and formula (A-5), R is each independently a group selected from alkyl having 1 to 45 carbons, cycloalkyl having 4 to 8 carbons, aryl having 6 to 14 carbons and arylalkyl having 7 to 24 carbons. In the alkyl having 1 to 45 carbons, arbitrary hydrogen may be replaced by fluorine and arbitrary non-adjacent —CH$_2$— may be replaced by —O— or —CH═CH—.

In a benzene ring in aryl and arylalkyl, arbitrary hydrogen may be replaced by halogen or alkyl having 1 to 10 carbons. In the alkyl having 1 to 10 carbons, arbitrary hydrogen may be replaced by fluorine and arbitrary non-adjacent —CH$_2$— may be replaced by —O— or —CH═CH—. The number of carbons of alkylene in arylalkyl is 1 to 10, and arbitrary non-adjacent —CH$_2$— may be replaced by —O—.

In formula (A-1), formula (A-4) and formula (A-5), R is each independently preferably a group selected from cyclopentyl, cyclohexyl, phenyl and alkyl having 1 to 10 carbons. In the alkyl having 1 to 10 carbons, arbitrary hydrogen may be replaced by fluorine and arbitrary non-adjacent —CH$_2$— may be replaced by —O—. In phenyl, arbitrary hydrogen may be replaced by halogen such as fluorine or alkyl having 1 to 10 carbons. R is further preferably cyclopentyl, cyclohexyl, or phenyl in which arbitrary hydrogen may be replaced by chlorine, fluorine, methyl, methoxy or trifluoromethyl, and still further preferably cyclohexyl or phenyl, and most preferably, phenyl.

In formula (A-1), formula (A-3), formula (A-4) and formula (A-5), $R^{11}$ and $R^{12}$ are each independently a group selected from alkyl having 1 to 4 carbons, cyclopentyl, cyclohexyl and phenyl. Examples of alkyl having 1 to 4 carbons include methyl, ethyl, propyl, 2-methylethyl, butyl and t-butyl. Preferred examples of $R^{11}$ or $R^{12}$ include methyl and phenyl. $R^{11}$ and $R^{12}$ are preferably an identical group.

In formula (A-1) to formula (A-5), at least two of X are each independently hydrogen, in one molecule of each compound, and the rest is a group selected from alkyl having 1 to 4 carbons, cyclopentyl, cyclohexyl and phenyl. In formula (A-4) and formula (A-5), n is an integer from 0 to 100.

Specific examples of compound (A-4) preferably include a compound represented by formula (A-4-1) below.

Formula 19

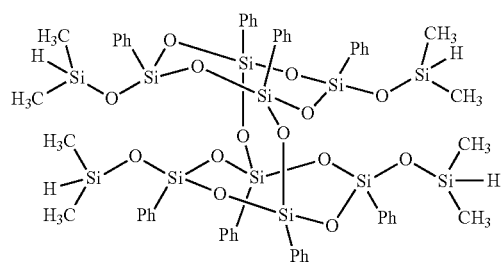

(A-4-1)

In formula (A-4-1), Ph stands for phenyl. A compound represented by formula (A-4-1) can be synthesized in accordance with the method described in WO 2004/024741 A. Moreover, any other compound can also be obtained in accordance with a publicly known method.

1-2. Compound (A) Including an Organopolysiloxane SiH Group Skeleton and Having Three or More SiH Groups in One Molecule Specific examples of compound (A) including the organopolysiloxane SiH group skeleton and having three or more SiH groups in one molecule include formula (A-6) below, and can be obtained according to a publicly known method.

Formula 20

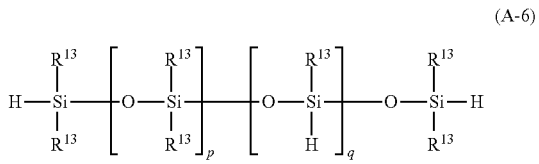
(A-6)

In formula (A-6), $R^{13}$ is each independently a group selected from alkyl having 1 to 6 carbons, cycloalkyl having 4 to 8 carbons, aryl having 6 to 14 carbons and arylalkyl having 7 to 24 carbons.

Specific examples of compound (A-6) preferably include a compound represented by formula (A-6-1) below.

Formula 21

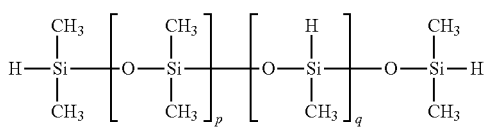
(A-6-1)

In formulas (A-6) and (A-6-1), p and q are the number from 1 to 300. An expression: $1 \leq p \leq 100$ preferably holds, an expression: $3 \leq p \leq 20$ further preferably holds, and an expression: $1 \leq q \leq 100$ preferably holds, and an expression: $1 \leq q \leq 20$ further preferably holds.

2. (B) Epoxy Derivative Having One Aliphatic Unsaturated Group in One Molecule 2-1. Epoxy Derivative (B) Having an Isocyanuric Ring Skeleton As epoxy derivative (B) having one aliphatic unsaturated group, an epoxy derivative having an isocyanuric ring skeleton is preferred, and specific examples include a compound represented by formula (B-1) below. In addition, as the compound represented by formula (B-1), a product sold as MA-DGIC by Shikoku Chemicals Corporation can be used.

In the case where epoxy derivative (B) includes an epoxy derivative having the isocyanuric ring skeleton such as the compound represented by formula (B-1) below, when a hydrosilylation addition reaction of the compound (A) and epoxy derivative (B) is performed, the compound of the invention is obtained. In the above case, whether a hydrosilylation addition reaction of isocyanurate compound (C) having two alkenyl groups in one molecule is allowed with compound (A) and epoxy derivative (B) may be arbitrary.

Formula 22

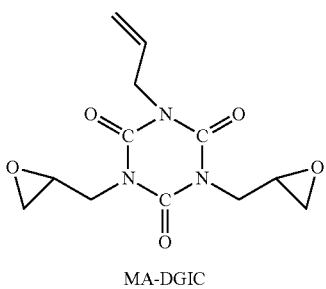
(B-1)

MA-DGIC 2-2. Epoxy Derivative (B) Having No Isocyanuric Ring Skeleton

Specific examples of any other epoxy derivative (B) include compounds represented by formula (B-2), formula (B-3) and formula (B-4) below. In the case where epoxy derivative (B) includes an epoxy derivative having no isocyanuric ring skeleton such as the compounds represented by formulas (B-2) to (B-4), a hydrosilylation addition reaction of isocyanurate compound (C) having two alkenyl groups in one molecule is allowed with the compound (A) and epoxy derivative (B).

Formula 23

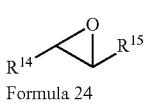
(B-2)

Formula 24

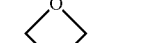
(B-3)

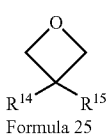

Formula 25

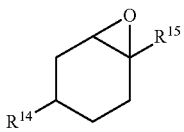
(B-4)

In formula (B-2), formula (B-3) and formula (B-4), one of $R^{14}$ and $R^{15}$ is an alkenyl group having 2 to 10 carbons, and one of —$CH_2$— in the alkenyl group may be replaced by —O— or 1,4-phenylene, and the other of $R^{14}$ and $R^{15}$ is hydrogen or alkyl having 1 to 6 carbons.

As compound (B-2), a compound represented by formula (B-2-1) below is preferred

Formula 26

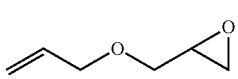
(B-2-1)

As compound (B-3), a compound represented by formula (B-3-1) below is preferred

Formula 27

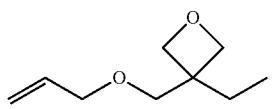
(B-3-1)

Specific examples of compound (B-4) include a compound represented by formula (B-4-1) or formula (B-4-2) below. In addition, as the compound represented by formula (B-4-1), a product sold as "Celloxide 2000" (registered trademark) by Daicel Chemical Industries, Ltd cam be used.

Formula 28

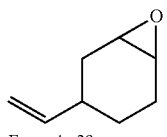
(B-4-1)

Formula 29

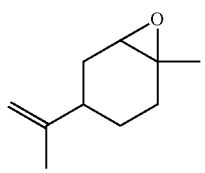
(B-4-2)

3. (C) Organopolysiloxane Having Two Alkenyl Groups in One Molecule, and Having a Number Average Molecular Weight of 100 to 500,000, or an Isocyanurate Compound Having Two Alkenyl Groups in One Molecule 3-1 Compound (C) being Organopolysiloxane Polyorganosiloxane Having Two Alkenyl Groups in One Molecule, and Having a Number Average Molecular Weight of 100 to 500,000

Specific examples of compound (C) being organopolysiloxane having two alkenyl groups in one molecule, and having a number average molecular weight of 100 to 500,000 include a compound represented by formula (C-1) below.

Formula 30

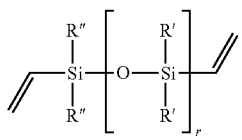
(C-1)

In formula (C-1), R' and R" are each independently a group selected from alkyl having 1 to 4 carbons, cyclopentyl, cyclohexyl and phenyl, and r is an integer from 0 to 100. R' and R" are preferably methyl. Then, r is preferably 1 to 100, and further preferably, 2 to 20.

In the case where the compound (A) includes a compound including an organopolysiloxane skeleton in the hydrosilylation addition reaction for obtaining the compound of the invention, compound (C) being organopolysiloxane having two alkenyl groups in one molecule, and having the number average molecular weight of 100 to 500,000 may be arbitrary. Moreover, in the case where the compound (A) includes a compound including a silsesquioxane skeleton, the hydrosilylation addition reaction of compound (C) being organopolysiloxane having two alkenyl groups in one molecule, and having the number average molecular weight of 100 to 500,000 is preferably allowed with (A) and (B).

3-2. Isocyanurate Compound (C) Having Two Alkenyl Groups

Specific examples of compound (C) being an isocyanurate compound having two alkenyl groups include compounds represented by formulas (C-2) and (C-3) below. As the compounds, compounds commercially available as DA-MGIC and Me-DAIC, respectively, from Shikoku Chemicals Corporation can be used.

Formula 31

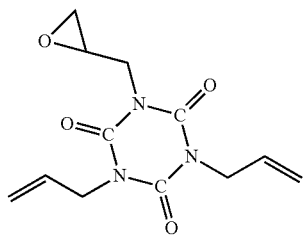
(C-2)

DA-MGIC

Formula 32

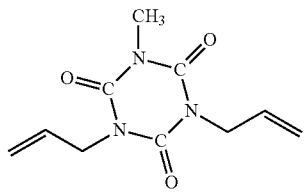
(C-3)

Me-DGIC

In the case where the epoxy derivative (B) includes an epoxy derivative having no isocyanuric ring skeleton in the hydrosilylation addition reaction for obtaining the compound of the invention, the hydrosilylation addition reaction of the isocyanurate compound (C) having two alkenyl groups is allowed with the compound (A) and epoxy derivative (B).

4. Compound (D) Having an Aliphatic Unsaturated Group and Having an Alkoxysilyl Group Specific examples of compound (D) having an aliphatic unsaturated group and having an alkoxysilyl group include a group represented by formula (D-1) below.

Formula 33

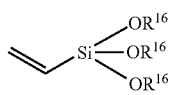
(D-1)

$R^{16}$ is each independently a group selected from methyl, ethyl, butyl and isopropyl. $R^{16}$ is preferably methyl or ethyl, and further preferably methyl.

Moreover, specific examples of compound (D) having the aliphatic unsaturated group, and having the trialkylsilyl group include a group represented by formula (D-2) below.

Formula 34

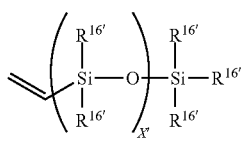
(D-2)

$R^{16'}$ is each independently a group selected from methyl, ethyl, butyl and isopropyl. $R^{16'}$ is preferably methyl or ethyl, and further preferably, methyl. X' is the number of repetitions of $-OSi(R^{16'})_2-$. X' is a mean value satisfying 1 to 20, and preferably, a mean value satisfying 1 to 10.

Specific examples of compound (D) having an aliphatic unsaturated group, and having a vinyl group include an identical compound represented by formula (C-1) above.

5. Hydrosilylation Addition Reaction

A hydrosilylation reaction is preferably performed in a solvent. The solvent used for the hydrosilylation reaction is not particularly restricted if the solvent does not adversely affect progress of the reaction. Specific examples of preferred solvents include a hydrocarbon solvent such as hexane and heptane, an aromatic hydrocarbon solvent such as benzene, toluene and xylene, an ether solvent such as diethyl ether, tetrahydrofuran (THF) and dioxane, a halogenated hydrocarbon solvent such as methylene chloride and carbon tetrachloride, and an ester solvent such as ethyl acetate.

The solvents may be used alone or in combination with a plurality of solvents. In the solvents, an aromatic hydrocarbon solvent is preferred, and among the solvents, toluene is most preferred.

The hydrosilylation reaction may be performed at room temperature. Heating may be applied in order to accelerate polymerization. Cooling may also be applied in order to control heat generation by polymerization, unfavorable polymerization or the like. In hydrosilylation polymerization, a catalyst can be used when necessary.

Addition of the hydrosilylation catalyst further easily allows progress of polymerization. As the hydrosilylation catalyst, a Karstedt catalyst, a Speier catalyst, hexachloroplatinic acid or the like can be preferably utilized.

The hydrosilylation catalysts have high reactivity, and therefore addition of a small amount thereof sufficiently allows progress of the reaction. An amount of use thereof is, in terms of a ratio of a transition metal contained in the catalyst based on a hydrosilyl group, preferably, $10^{-9}$ to 1 mol %, and further preferably, $10^{-7}$ to $10^{-3}$ mol %.

6. Compound Including an Organopolysiloxane or Silsesquioxane Skeleton Including as an Essential Component an Isocyanuric Ring Skeleton and an Epoxy Group, and Having an SiH Group Residue 6-1. Compound Including a Silsesquioxane Skeleton Including as an Essential Component an Isocyanuric Ring Skeleton and an Epoxy Group, and Having an SiH Group Residue Specific examples of the silsesquioxane skeleton including as the essential component the isocyanuric ring skeleton and the epoxy group, and including the SiH group residue as obtained by allowing the hydrosilylation addition reaction of (A) and (B), and when necessary (C) as described above include a compound represented by formula (1) below.

Formula 35

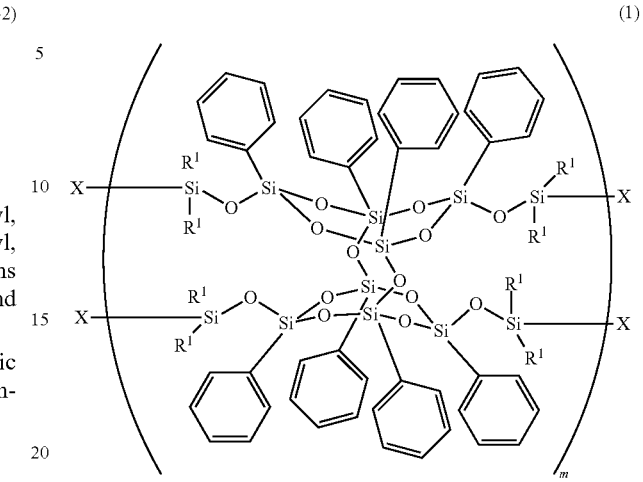
(1)

In formula (1), X is each independently a group represented by formula (a), formula (b-i), formula (b-ii), formula (b-iii), formula (c-i), formula (c-ii), formula (c-iii) or formula (d) below. $R^1$ is each independently a group selected from alkyl having 1 to 4 carbons, cyclopentyl and cyclohexyl, and preferably, methyl. Then, m is 1 to 100, and preferably, 1.

A group represented by formula (a) below is derived from the compound (A), and is an SiH group residue after the compound (A) and epoxy derivative (B), and when necessary compound (C) and compound (D) react. Accordingly, the group represented by formula (a) below can react with thermosetting resin being the reaction product of silsesquioxane and organopolysiloxane, to which resin the compound of the invention is applied as an adhesion-imparting agent, and therefore the group is considered to reinforce a function as the adhesion-imparting agent of the compound of the invention.

Formula 36

(a)

Groups represented by formulas (b-i) to (b-iii) are derived from the epoxy derivative (B). The groups represented by formulas (b-i) to (b-iii) below include a group having one unsaturated group and having an epoxy group.

Formula 37

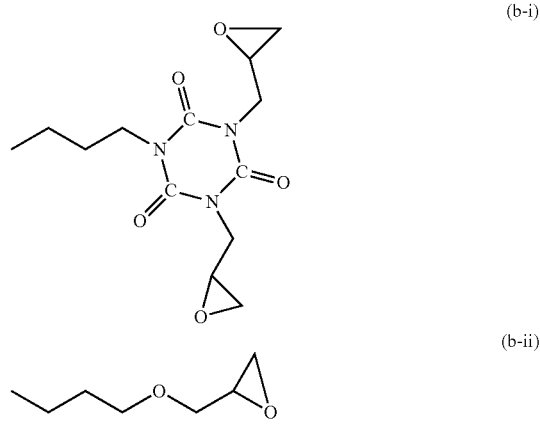

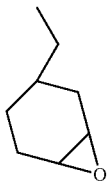
(b-iii)

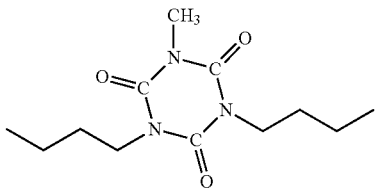
(c-iii)

In the case where the group derived from epoxy derivative (B) is represented by formula (b-i), the group has the epoxy group and the isocyanuric ring skeleton, and therefore a group derived from the compound C {group represented by formulas (c-i) to (c-iii)} may be arbitrary.

In the case where the group derived from epoxy derivative (B) is represented by formula (b-ii) or formula (b-iii), the group has the epoxy group, but has no isocyanuric ring skeleton, and therefore, as a group derived from compound (C), a group represented by formula (c-ii) or formula (c-iii) below is provided therefor, thereby allowing provision of the epoxy group and the isocyanuric ring skeleton for the compound of the invention.

The groups represented by formulas (c-i) to (c-iii) below are derived from the compound (C), and also a crosslinking component. In the case where the group derived from the compound (C) is organopolysiloxane represented by formula (c-i), flexibility or compatibility can be provided for the compound of the invention. Moreover, when the group derived from the compound (C) includes a group having an isocyanuric ring skeleton represented by formula (c-ii) or formula (c-iii), the isocyanuric ring skeleton is introduced into the compound of the invention, and therefore an improvement of adhesion can be expected.

A compound having the isocyanuric ring skeleton represented by formula (c-ii) or formula (c-iii) is, as is different from a block copolymer of a silicone component and isocyanurate, a block copolymer with silsesquioxane, and therefore can be an adhesion agent suitable for an addition hardening type composition including the reaction product of silsesquioxane and organopolysiloxane.

Formula 38

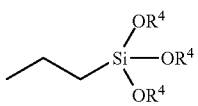
(c-i)

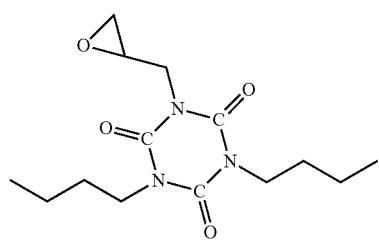
(c-ii)

In formula (c-i), $R^2$ and $R^3$ are each independently a group selected from alkyl having 1 to 4 carbons, cyclopentyl, cyclohexyl and phenyl, t is the number of repetitions of $—OSi(R^3)_2—$, and is a mean value satisfying 1 to 100.

A group represented by formula (d-i) below is derived from the compound (D), and is an arbitrary component. The group represented by formula (d-i) is introduced thereinto for the purpose of improving adhesion with a metal or improving compatibility with resin.

Formula 39

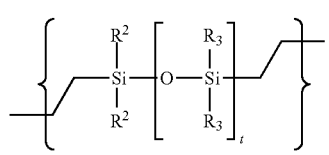
(d-i)

In formula (d-i), $R^4$ is each independently a group selected from methyl, ethyl, butyl and isopropyl.

A group represented by formula (d-ii) below is derived from the compound (D), and is an arbitrary component. The group represented by formula (d-ii) is introduced thereinto for the purpose of improving compatibility with resin, adjusting viscosity or adjusting hardness after hardening a hardening resin composition.

Formula 40

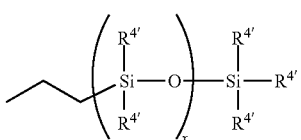
(d-ii)

In formula (d-ii), $R^{4'}$ is each independently a group selected from methyl, ethyl, butyl and isopropyl, and preferably, methyl. Then, x is the number of repetitions of $—OSi(R^{4'})_2—$. Then, x is a mean value satisfying 1 to 20, and preferably, a mean value satisfying 1 to 10.

A group represented by formula (d-iii) below is derived from the compound (D), and is an arbitrary component. The group represented by formula (d-iii) is introduced thereinto for the purpose of improving compatibility with resin, adjusting viscosity or adjusting hardness after hardening a hardening resin composition.

Formula 41

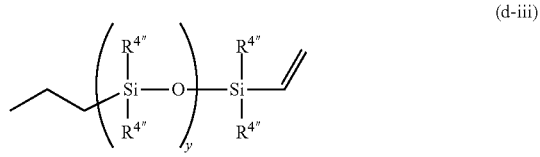

(d-iii)

In formula (d-iii), $R^{4''}$ is each independently a group selected from methyl, ethyl, butyl and isopropyl, and preferably, methyl. Then, y is the number of repetitions of $-OSi(R^{4''})_2-$. Then, y is a mean value satisfying 1 to 20, and preferably, a mean value satisfying 1 to 10.

With regard to the number of groups per one molecule of compound represented by formula (1) (per one molecule on average of the compound when the compound is a mixture in which a ratio of the group represented by formula (a), a ratio of the group represented by formula (b-i) and a ratio of the group represented by formula (b-ii) and formula (b-iii) are different), in the case where the number of groups represented by formula (a) is taken as A, the number of groups represented by formula (b-i), formula (b-ii) or formula (b-iii) is taken as B, the number of groups represented by formula (c-i), formula (c-ii) or formula (c-iii) is taken as C, and the number of groups represented by formula (d-i), formula (d-ii) or formula (d-iii) is taken as D, expressions: $A+B+2C+D=4$, $0.1 \le A \le 3.5$, $0.1 \le B \le 3.5$, $0 \le 2C \le 2.0$, and $0 \le D \le 3.0$ hold. Values from A to D can be adjusted in conformity with properties of the thermoplastic resin composition to which the compound of the invention is applied as the adhesion-imparting agent.

The group derived from the compound (C) is further explained. The group derived from the compound (C) is of a double decker and a crosslinking component. The compound of the invention specifically takes polymer structure as in a compound represented by formula (1-1) below, for example.

Formula 42

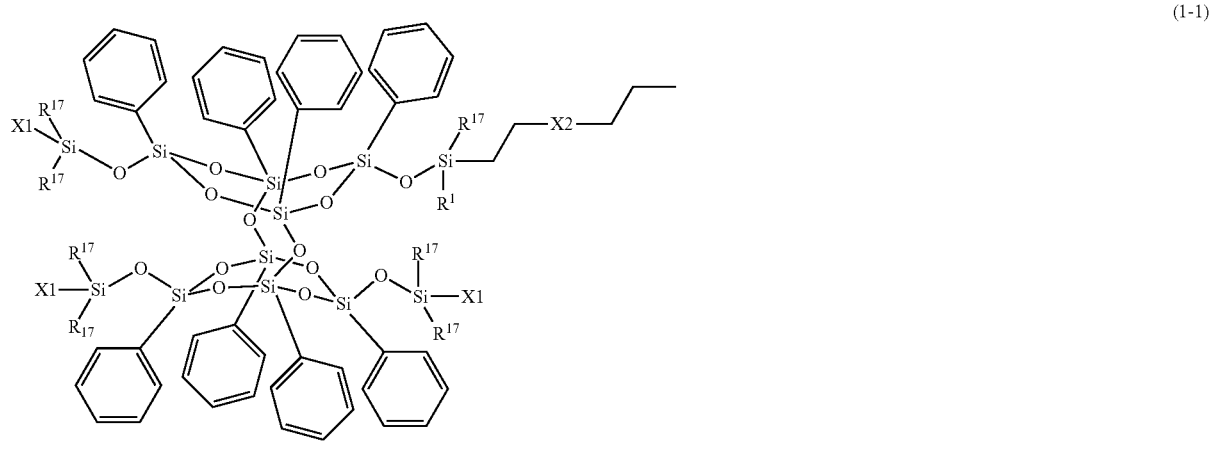

(1-1)

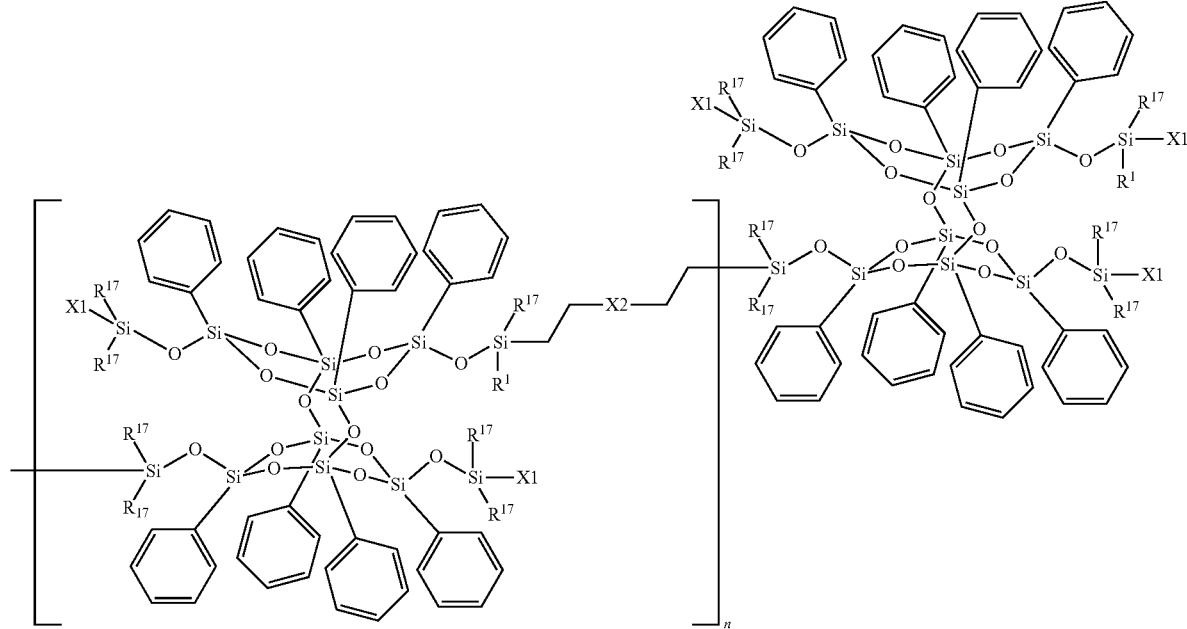

In formula (1-1), X1 and X2 are each independently a group represented by formula (a), formula (b-i), formula (b-ii) or formula (b-iii) above. $R^{17}$ is each independently a group selected from alkyl having 1 to 4 carbons, cyclopentyl and cyclohexyl, and preferably, methyl. Then, u is 0 to 1,000.

As the value of C being the number of groups represented by formula (c-i), formula (c-ii) or formula (c-iii) becomes larger, the number of the crosslinking components of molecules with each other further increases, and the compound of the invention results in a compound having higher macromolecular weight. If C=0, the compound is in a state with no crosslinking component. In the range of an expression: 0<C<1, the number of crosslinking components further increases as the value of C becomes larger, and the molecular weight further increases. In the range of an expression: c>1, the compound is in a state in which crosslinking of molecules with each other significantly progresses to become in a gel form, and therefore the compound is quite difficult to be used as thermosetting resin. The value of C is changed within the range of an expression: 0≤C≤1, thereby allowing adjustment of the molecular weight of the compound of the invention.

The group derived from the compound (D) is further explained. A reagent and a reaction method for obtaining the group represented by formula (d-ii) or formula (d-iii) are explained.

First, the reagent for obtaining the group represented by formula (d-ii) or the group represented by formula (d-iii) is explained.

As shown in the reaction formula below, an equilibration reaction of divinyltetradisiloxane (DVDS) and hexamethyldisiloxane (MM) in an excess mol is performed to cyclic octamethyl tetracyclo siloxane (D4) in the presence of an acid catalyst to give an equilibration mixture of compound a, compound b and compound c, which is taken as the reagent for obtaining the group represented by formula (d-ii) or the group represented by formula (d-iii).

Formula 43

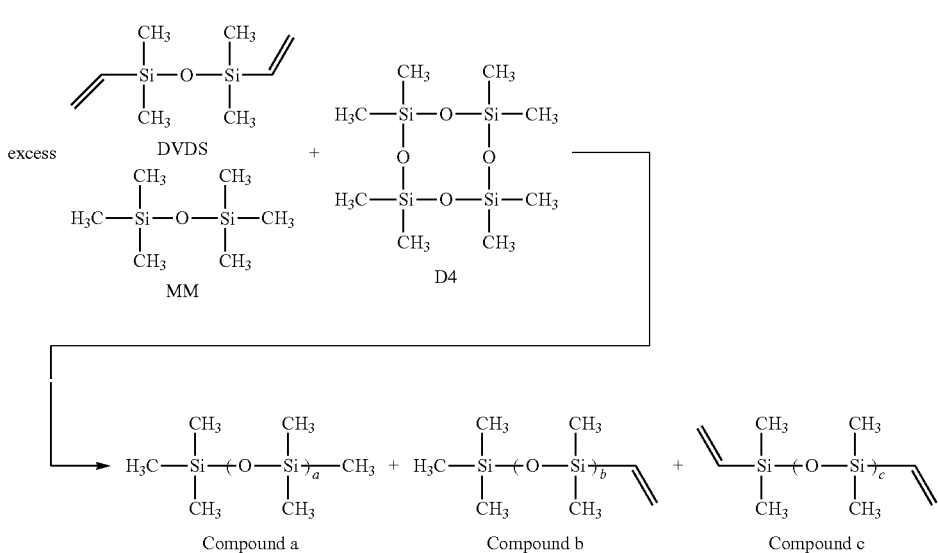

In the reaction formula, a is 1 to 20, b is 1 to 20, and c is 1 to 20.

A mole ratio of a sum of DVDS and MM to D4 in the reaction is preferably 2 or more. If the mole ratio is 2 or more, the molecular weight of a siloxane chain to be produced is short to be a component that can be removed by distillation, and removal of excess compound a, compound b and compound c that is not involved in the reaction is facilitated in a subsequent purification step.

A reaction method for obtaining the group represented by formula (d-ii) or formula (d-iii) is described.

As a reaction for the compound having the isocyanuric ring skeleton and the epoxy group, and providing the group represented by formula (d-ii) or formula (d-iii) above according to the invention, a case is explained where the group derived from epoxy derivative (B) includes a group represented by formula (b-i).

As shown in the reaction formula below, in a first-step reaction, a hydrosilylation reaction of the compound represented by formula (A-4-1) above (double decker having four SiH groups) is previously allowed with the compound represented by formula (B-1) above to first give the compound having the group represented by formula (b-i).

Formula 44

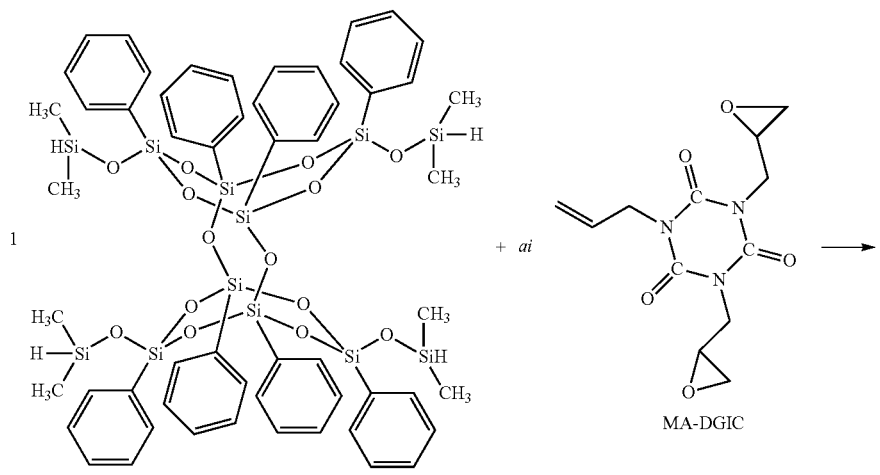

In the reaction formula, ai is 0.1 to 3.5.

Subsequently, as shown in the reaction formula below, in a second-step reaction, a hydrosilylation reaction is allowed to be excessive in the number of moles of a vinyl group of the mixture of compound a, compound b and compound c to the number of moles of the SiH group in the compound in the first step to give the product below.

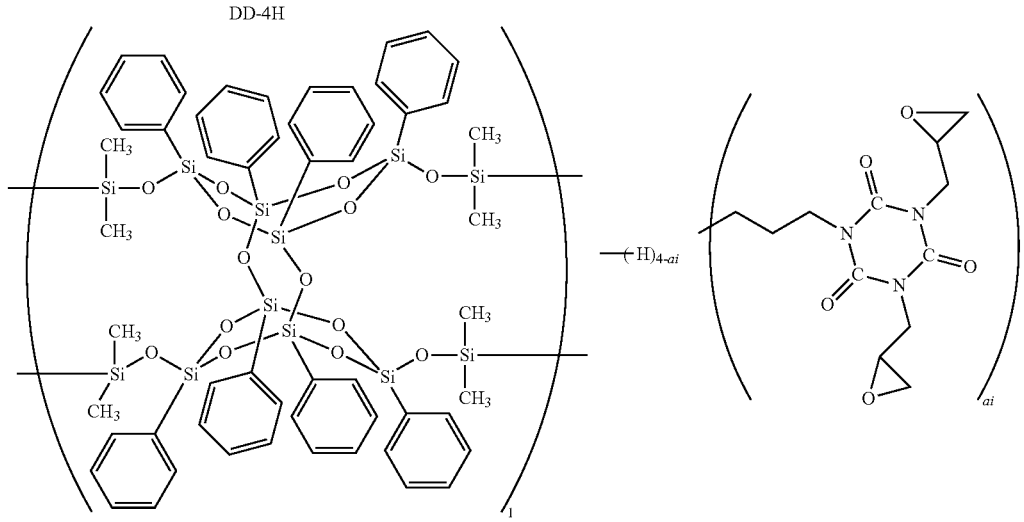

Formula 45

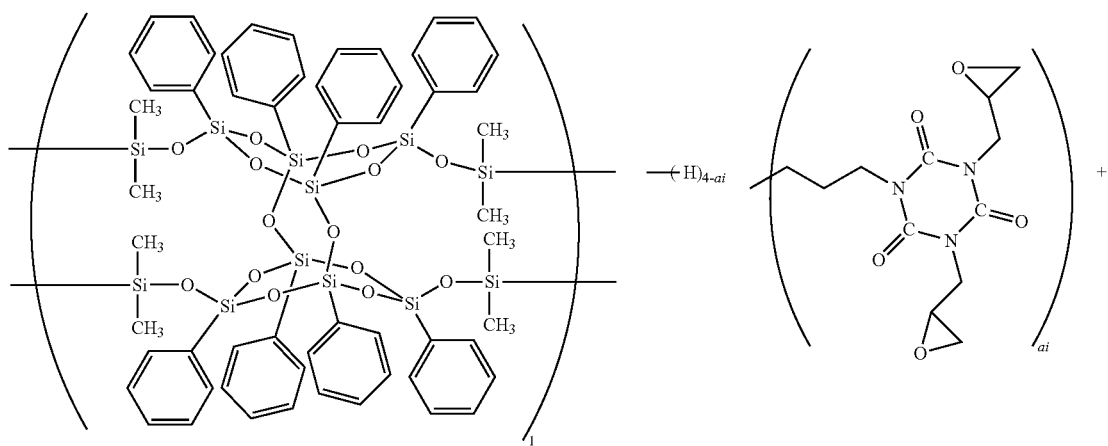

-continued

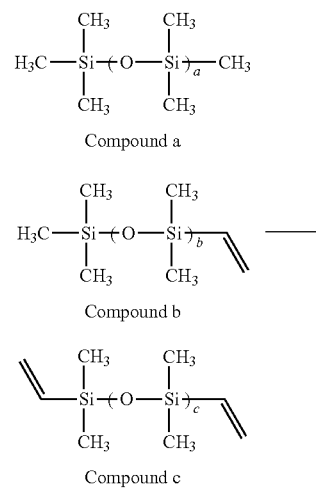

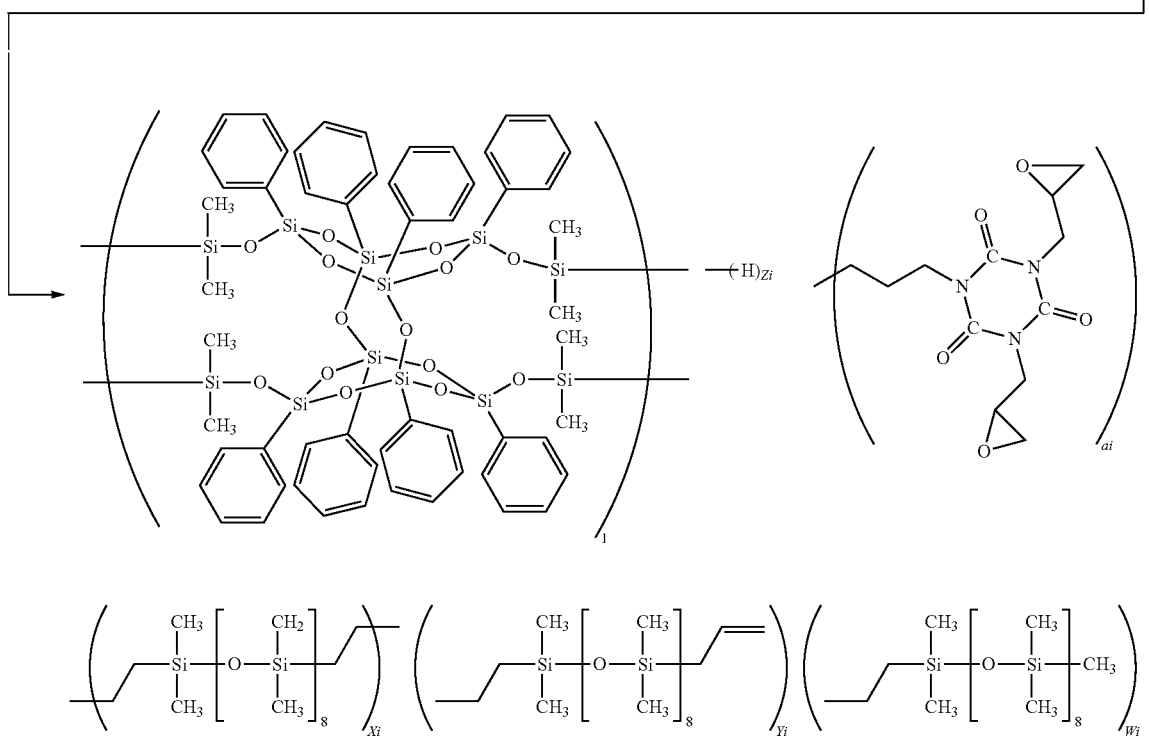

In the reaction formula, an expression: $0.1 \leq ai \leq 3.5$ holds for ai, an expression: $0 \leq 2Xi \leq 2.0$ holds for Xi, an expression: $0 \leq Yi \leq 3.0$ holds for Yi, an expression: $0.1 \leq Zi \leq 3.5$ holds for Zi, and an expression: $0 \leq Wi \leq 3.0$ holds for Wi.

The hydrosilylation reaction is allowed to be excessive in the number of moles of the vinyl group, but an SiH group has been found to exist as a remaining Si—H group without disappearance in a high temperature region of 100° C. or higher, and further 120° C. or higher.

Extra compound a, compound b and compound c that are not involved in the reaction can be distilled off by distillation using a thin-film evaporator. Alternatively, the compounds can also be removed by a solvent extraction method. Alternatively, the compounds may be arbitrarily allowed to remain as is. Temperature at which extra compound a, compound b and compound c are distilled off in distillation using the thin-film evaporator is preferably in the range of 120° C. to 180° C., and operation pressure is preferably 1 mmHg or less.

A preferred solvent for removing extra compound a, compound b and compound c in the solvent extraction method has large dissolving power, and a comparatively low boiling point. The preferred solvent is a lower alcohol. A particularly preferred solvent is methanol. A further increase of a degree of purification only needs to increase the number of repetitions of a solvent extraction operation.

Next, a method for obtaining only the group represented by formula (d-iii) is described in detail.

As shown in the reaction formula below, in a first-step reaction, a hydrosilylation reaction of the compound represented by formula (A-4-1) above (double decker having four SiH groups) is previously allowed with the compound represented by formula (B-1) above to first give the compound having the group represented by formula (b-i).

Formula 46

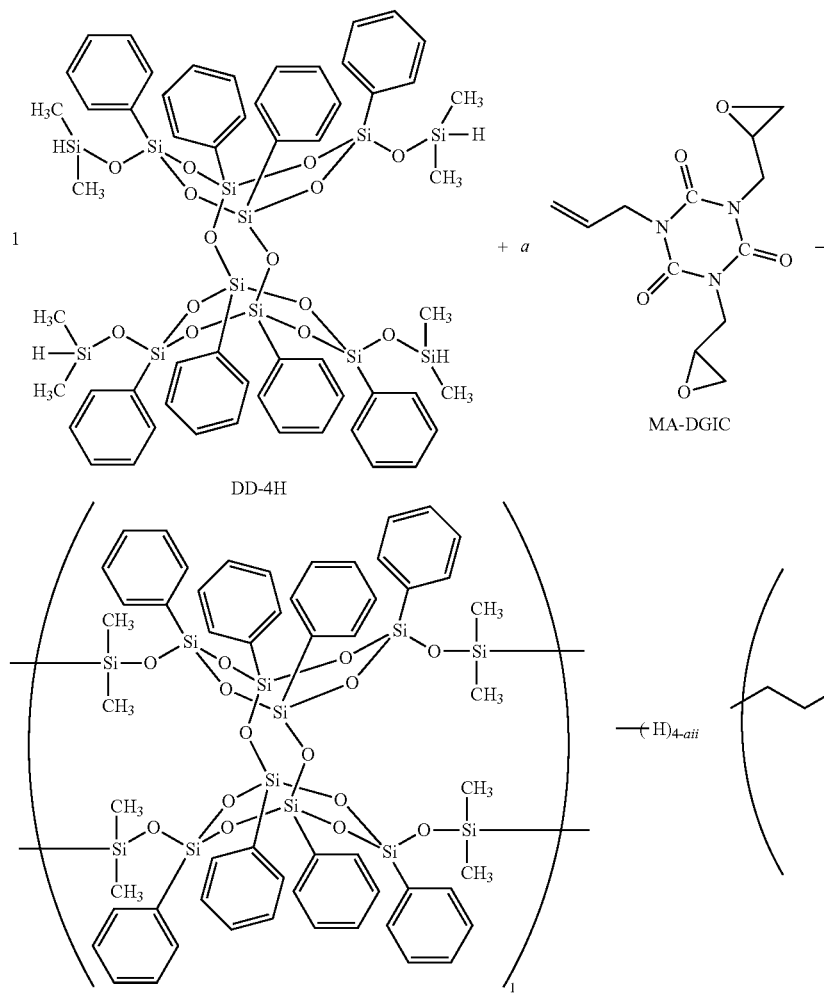

In the reaction formula, an expression: $0.1 \leq aii \leq 3.5$ holds for aii.

As a reaction product to be used in a second-step reaction, a compound represented by formula (C-1) above is used. As shown in the reaction formula below, a hydrosilylation reaction is allowed to be excessive in the number of moles of a vinyl group of the compound represented by formula (C-1) above to the number of moles of the SiH group in the compound in the first step to give the product below.

Formula 47

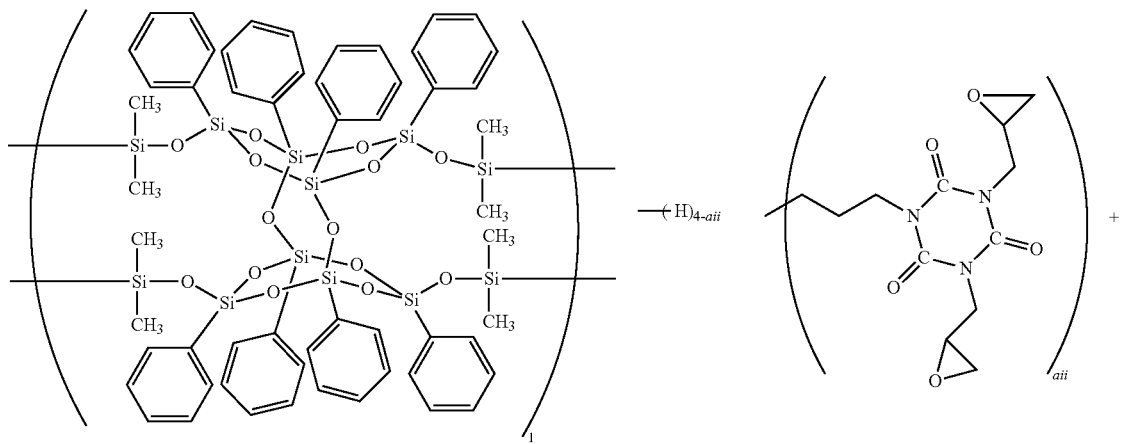

-continued

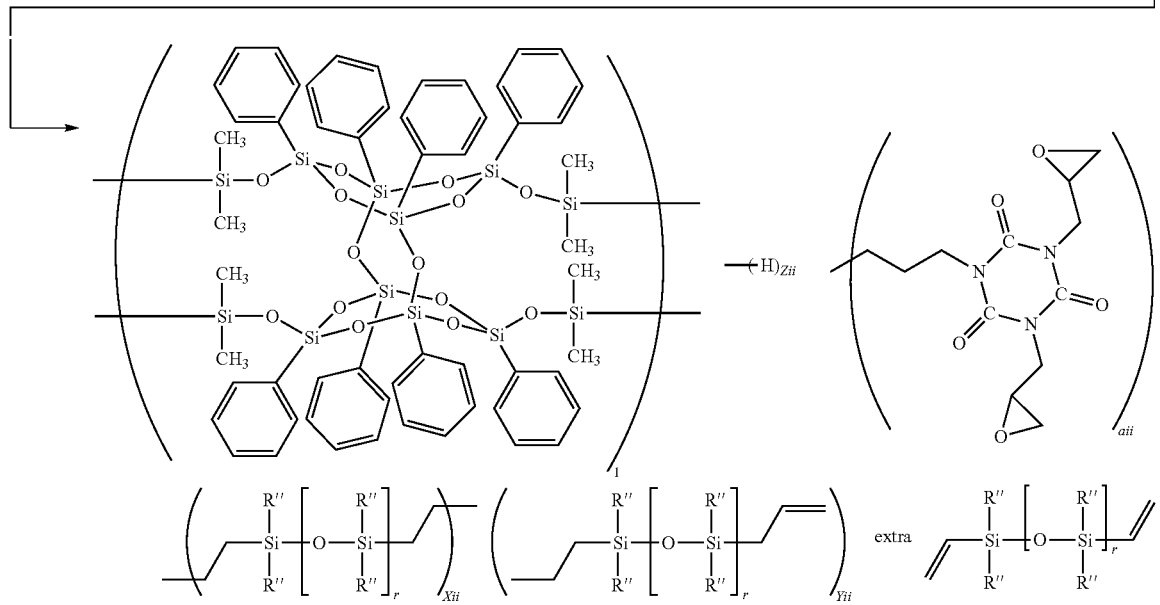

In the reaction formula, an expression: $0.1 \leq aii \leq 3.5$ holds for aii, an expression: $0 \leq 2Xii \leq 2.0$ holds for Xii, an expression: $0 \leq Yii \leq 3.0$ holds for Yii, an expression: $0.1 \leq Zii \leq 3.5$ holds for Zii, and r is 1 to 20.

The hydrosilylation reaction is allowed to be excessive in the number of moles of the vinyl group of the compound represented by formula (C-1) above, but an Si—H group has been found to exist as a remaining SiH group without disappearance in a high temperature region of 100° C. or higher, and further 120° C. or higher.

Extra organopolysiloxane that is not involved in the reaction is a compound having a vinyl group, and therefore may be allowed to remain as is, as a thermosetable resin component. Alternatively, the organopolysiloxane may be appropriately removed by solvent extraction or the like. A preferred solvent for removing extra organopolysiloxane has large dissolving power, and a comparatively low boiling point. The preferred solvent is a lower alcohol. A particularly preferred solvent is methanol. A further increase of a degree of purification only needs to increase the number of repetitions of a solvent extraction operation.

6-2. Compound Having an Organopolysiloxane Skeleton Including as an Essential Component an Isocyanuric Ring Skeleton and an Epoxy Group, and Having an SiH Group Residue Specific examples of the compound having the organopolysiloxane skeleton including as the essential component the isocyanuric ring skeleton and the epoxy group, and having the SiH group residue as obtained by allowing the hydrosilylation addition reaction of the compound (A) and the compound (B), and when necessary, the compound (C) as described above include a compound represented by formula (2) below.

Formula 48

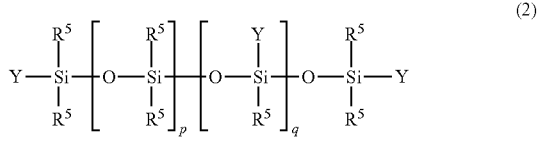

(2)

In formula (2), Y is each independently a group represented by formula (a), formula (b-i), formula (b-ii), formula (b-iii) or formula (d) below. $R^5$ is each independently a group selected from alkyl having 1 to 4 carbons, cyclopentyl and cyclohexyl, aryl having 6 to 14 carbons and arylalkyl having 7 to 24 carbons. Then, p and q are the number of 1 to 100, respectively.

Formula 49

(a)

Formula 50

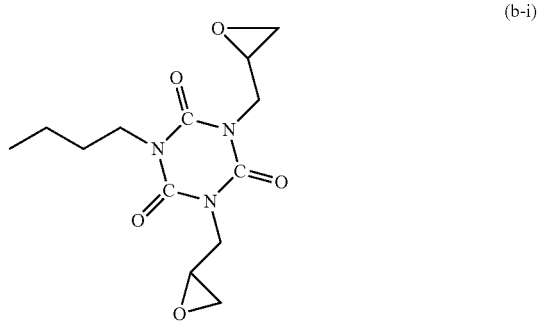

(b-i)

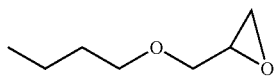

(b-ii)

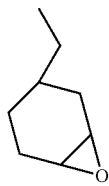

(b-iii)

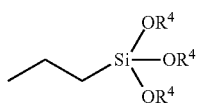

Formula 51

(d)

In formula (d), $R^4$ is each independently a group selected from methyl, ethyl, butyl and isopropyl.

In the case where a ratio of the group represented by formula (a) per the group represented by Y in one molecule of the compound represented by formula (2) is taken as A, a ratio of the group represented by formula (b-i), formula (b-ii) or formula (b-iii) is taken as B, and a ratio of the group represented by formula (d) is taken as D, expressions: $A+B+D=1$, $0.1 \leq A \leq 0.7$, $0.05 \leq B \leq 0.6$, and $0.01 \leq D \leq 0.6$ hold. In addition, among B, the group represented by formula (b-i) is an essential component, the group represented by formula (b-ii) and the group represented by formula (b-iii) are arbitrary.

7. Thermosetting Resin Composition

The compound of the invention can be added as the adhesion-imparting agent to the thermosetting resin composition. As the thermosetting resin composition according to the invention, a thermosetting resin composition containing (I) to (IV) as described below is preferred:

(I) a reaction product of double-decker silsesquioxane and organopolysiloxane, and thermosetting resin having an SiH group or both an SiH group and an alkenyl group;

(II) thermosetting resin being an organosiloxane compound that have two or more alkenyl groups and may include a silsesquioxane skeleton;

(III) as the adhesion-imparting agent, the compound of the invention; and (IV) a Pt catalyst.

7-1. (I) Reaction Product of Double-Decker Silsesquioxane and Organopolysiloxane, and Thermosetting Resin Having an SiH Group or Both an SiH Group and an Alkenyl Group Specific examples of the thermosetting resin (I) include a compound represented by formula (I) below.

Formula 52

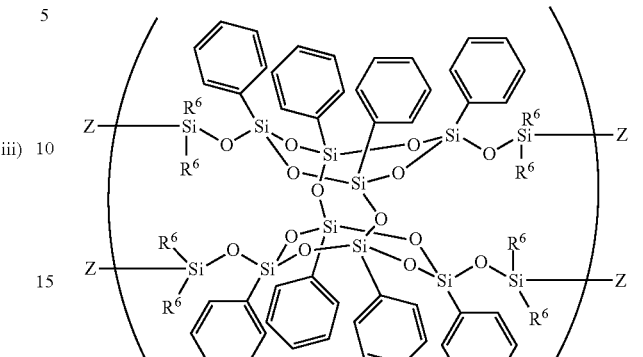

(I)

In formula (I), Z is each independently a group represented by formula (Z-i), formula (Z-ii) or formula (Z-iii) below. $R^6$ is each independently a group selected from alkyl having 1 to 4 carbons, cyclopentyl and cyclohexyl, and n is 1 to 100. Above all, n is preferably 1.

Formula 53

—H   (Z-i)

Formula 54

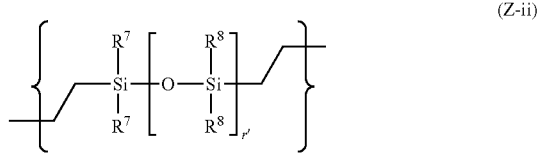

(Z-ii)

In formula (Z-ii), $R^7$ and $R^8$ are each independently a group selected from alkyl having 1 to 4 carbons, cyclopentyl, cyclohexyl and phenyl, r' is the number of repetitions of —OSi($R^8$)$_2$—, and r' is a mean value satisfying 2 to 100. Then, r' is preferably 2 to 20.

Formula 55

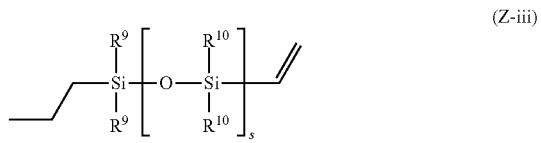

(Z-iii)

In formula (Z-iii), $R^9$ and $R^{10}$ are each independently a group selected from alkyl having 1 to 4 carbons, cyclopentyl, cyclohexyl and phenyl, s is the number of repetitions of —OSi($R^3$)$_2$—, and s is a mean value satisfying 2 to 50.

With regard to the number of groups per one molecule of the compound represented by formula (I) (per one molecule on average of the compound being a mixture of compounds in which a ratio of the group represented by formula (Z-i), a ratio of the group represented by formula (Z-ii) and a ratio of the group represented by formula (Z-iii) are different), in the case where the number of groups represented by formula (Z-i) is taken as e, the number of groups represented by formula (Z-ii)

is taken as f, and the number of groups represented by formula (Z-iii) is taken as g, expressions: e+2f+g=4, 1.0≤e≤3.0, 0≤2f≤2.0, and 0≤g≤2.0 hold.

In the invention, a compound in the range of satisfying the expressions: e+2f+g=4, 1.0≤e≤3.0, 0≤2 f≤2.0, and 0≤g≤2.0 is explained.

If e>g, the compound represented by general formula (I) has a larger number of SiH groups, on average, than the number of vinyl groups, and can be defined as so-called SiH group type thermosetting resin.

As the thermosetting resin (I), the SiH group type thermosetting resin is preferably used. As for the e, from a viewpoint of remarkably developing excellent characteristics upon forming a hardened material, e is preferably 1.0 to 3.0, and further preferably, 1.5 to 2.5.

The thermosetting resin composition according to the invention preferably contains the thermosetting resin (I) in an amount of 40 to 99% by mass, and further preferably, 70 to 95% by mass, based on the total amount of the thermosetting resin composition.

7-2. (II) Thermosetting Resin being an Organosiloxane Compound that has Two or More Alkenyl Groups in One Molecule and May Also Include a Silsesquioxane Skeleton Specific examples of the alkenyl groups include a vinyl group, an allyl group, a 1-butenyl group, a 1-hexenyl group and a propenyl group. A vinyl group is preferred from ease of synthesis.

Specific examples of thermosetting resin (II) being the organosiloxane compound that has two or more alkenyl groups in one molecule and may also include the silsesquioxane skeleton include a compound represented by formula (II-1) below.

Formula 56

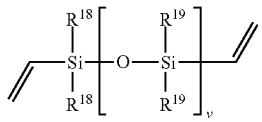
(II-1)

In formula (II-1), $R^{18}$ and $R^{19}$ are each independently a group selected from alkyl having 1 to 4 carbons, cyclopentyl, cyclohexyl and phenyl, and v is the number of 0 to 100. $R^{18}$ and $R^{19}$ are preferably methyl. Then, v is preferably 1 to 100, and further preferably, 1 to 20.

Moreover, specific examples of thermosetting resin (II) being the organosiloxane compound that has two or more alkenyl groups in one molecule and may also include the silsesquioxane skeleton include a compound represented by formula (II-2) below.

Formula 57

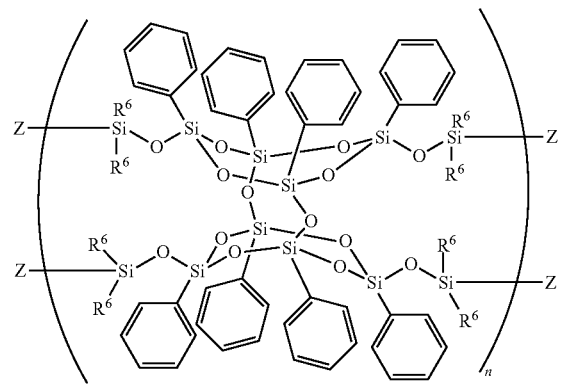
(II-2)

In formula (II-2), Z is each independently a group represented by formula (Z-ii) or formula (Z-iii) below. $R^6$ is each independently a group selected from alkyl having 1 to 4 carbons, cyclopentyl and cyclohexyl, and n is 1 to 100. Above all, n is preferably 1.

Formula 58

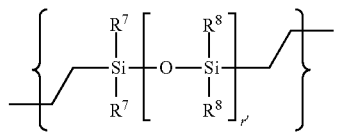
(Z-ii)

In formula (Z-ii), $R^7$ and $R^8$ are each independently a group selected from alkyl having 1 to 4 carbons, cyclopentyl, cyclohexyl and phenyl, r' is the number of repetitions of $—OSi(R^8)_2—$, and r' is a mean value satisfying 2 to 100. Then, r' is further preferably 2 to 20.

Formula 59

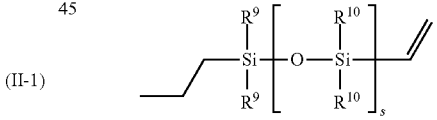
(Z-iii)

In formula (Z-iii), $R^9$ and $R^{30}$ are each independently a group selected from alkyl having 1 to 4 carbons, cyclopentyl, cyclohexyl and phenyl, s is the number of repetitions of $—OSi(R^{10})_2—$, and s is a mean value satisfying 2 to 50. Then, s is further preferable 2 to 20.

With regard to the number of groups per one molecule of the compound represented by formula (II-2) (per one molecule on average of the compound being a mixture of compounds in which a ratio of the group represented by formula (Z-ii), a ratio of the group represented by formula (Z-iii) and a ratio of the group represented by formula (Z-iii) are different), in the case where the number of groups represented by formula (Z-ii) is taken as f, and the number of groups represented by formula (Z-iii) is taken as g, expressions: 2f+g=4, 0≤2f≤2, and 2≤g≤4 hold.

The thermosetting resin composition according to the invention preferably contains the thermosetting resin (II) in an amount of 0.1 to 50% by mass, and further preferably, 5 to 30% by mass, based on the total amount of the thermosetting resin composition.

7-3. (III) Compound Including an Organopolysiloxane or Silsesquioxane Skeleton Including as an Essential Component an Isocyanuric Ring Skeleton and an Epoxy Group, and Having an SiH Group Residue Compound (III) including an organopolysiloxane or silsesquioxane skeleton including as an essential component an isocyanuric ring skeleton and an epoxy group, and having an SiH group residue is added as an adhesion-imparting agent to the thermosetting resin composition according to the invention.

The thermosetting resin composition according to the invention preferably contains the thermosetting resin (III) in an amount of 0.01 to 15.0% by mass, and further preferably, 1 to 10% by mass, based on the total amount of the thermosetting resin composition.

In addition, an isocyanuric ring skeleton part and an epoxy group part in the compound (III) can be arbitrarily introduced thereinto, and thus the thermosetting resin composition according to the invention preferably contains the compound (III) to be 0.01 to 10.0% by mass, and further preferably, 0.05 to 5.0% by mass in a total of the isocyanuric ring skeleton part and the epoxy group part in the compound (III), based on the total amount of the thermosetting resin composition.

7-4. (IV) Pt Catalyst

A Pt catalyst contains platinum, and the platinum may be unoxidized or oxidized. Specific examples of oxidized platinum include platinum oxide. Specific examples of partially oxidized platinum include an Adams catalyst.

Specific examples of the Pt catalyst include a Karstedt catalyst, a Speier catalyst and hexachloroplatinic acid. The catalysts are generally well known. Above all, a Karstedt catalyst of unoxidized type is preferably used.

The thermosetting resin composition according to the invention preferably contains the Pt catalyst (IV) in an amount of 0.0001 ppm to 10 ppm, and further preferably, 0.1 to 3 ppm, based on the total amount of the thermosetting resin composition.

In the thermosetting resin composition according to the invention, a component described below may be further compounded.

(i) Phosphor

A phosphor is dispersed into the thermosetting resin composition according to the invention, thereby having a light-emitting function, and allowing use as an LED composition. The content of the phosphor in the thermosetting resin composition according to the invention is preferably 1 to 90% by mass, and further preferably, 2 to 50% by mass.

(ii) Silica

In the thermosetting resin composition according to the invention, silica may be added for the purpose of preventing sedimentation of the phosphor. A ratio of silica in the thermosetting resin composition according to the invention is preferably 1 to 50% in a weight ratio based on the total amount of the thermosetting resin composition.

(III) Nanoparticle Dispersion Liquid of Metal Oxide Such as Zirconium Oxide, Titanium Oxide or Alumina In the thermosetting resin composition according to the invention, a nanoparticle dispersion liquid of metal oxide such as zirconium oxide, titanium oxide or alumina may be added for the purpose of increasing a refractive index, mechanical strength, and adhesion force with a metal. A ratio of the nanoparticles dispersion liquid in the thermosetting resin composition according to the invention is preferably 1 to 50% in a weight ratio based on the total amount of the thermosetting resin composition.

A method for manufacturing the thermosetting resin composition according to the invention is not particularly limited, and specific examples include a method in which a mixer such as a homodisper, a homo mixer, a universal mixer, a planetary mixer, a kneader, a three-roll, and a bead mill is used, and under ordinary temperature or warming, a predetermined amount of each of a hardening accelerator and silicone resin as described above, and when necessary, a thermosetting agent and an antioxidant and so forth as described above is mixed.

Application of the thermosetting resin composition according to the invention is not particularly limited, but the composition can be used, for example, as a sealing agent, a housing material, a die bonding material for connecting with a lead electrode or a heat sink, an underfill material when a light emitting device of an optical semiconductor device such as a light emitting diode is subjected to flip chip mounting, and a passivation film on a light emitting device. Above all, an optical semiconductor apparatus that can efficiently extract light by light emission from an optical semiconductor device can be manufactured, and thus the composition can suitably used as the sealing agent, the underfill material or the die bonding material.

The thermosetting resin composition according to the invention is preferably heated at a temperature of 60 to 200° C., and further preferably, 80 to 160° C., thereby allowing obtaining of a hardened material. The hardened material obtained is excellent in a high refractive index and heat resistance, and simultaneously exhibits excellent adhesive properties to heat-resistant resin such as PA9T or LCP, or a Ag-plated base material.

The excellent adhesive properties of the hardened material formed by thermosetting the thermosetting resin composition according to the invention to the heat-resistant resin or the Ag-plated base material is caused by bonding of the SiH group included in the adhesion material according to the invention to the thermosetting resin being the base resin, well wetting of the epoxy group to the resin, and further satisfactory alignment of the isocyanuric ring skeleton to the heat-resistant resin or on a Ag surface to achieve interaction.

The thermosetting resin composition according to the invention is thermally set and shaped, thereby allowing obtaining of a molded object according to the invention. As a method for obtaining the molded object by thermosetting the thermosetting resin composition, a conventionally known method can be applied. Specific examples include injection molding, extrusion molding and compression molding.

The thermosetting resin composition according to the invention is hardened and shaped into a coating film (hardened coating film), thereby allowing utilization in various fields. The coating film is shaped, for example, through (1) a step for coating the thermosetting resin composition on a support (coating step), (2) a step for removing a solvent from a coated thermosetting resin composition to shape a coating film, and (3) a step for thermosetting the coating film by heating (post-baking step).

Use of the thermosetting resin composition according to the invention allows heating in the post-baking step at temperature (150 to 190° C.) lower than the temperature so far applied, and also improving of hardness of the film. Hereinafter, each step is explained in the order.

Specific examples of solvents (solvent media) include toluene, hexane, acetone, tetrahydrofuran and ethyl acetate. The solvent may be used or may not be used.

(1) Coating Step

For coating the thermosetting resin composition, for example, a spin coater, a slit & spin coater, a slit coater (also referred to as a die coater or a curtain flow coater), and inkjet can be used.

(2) Step for Removing a Solvent

After coating the thermosetting resin composition, for example, vacuum drying or pre-baking, preferably, pre-baking is performed, thereby forming a smooth unhardened coating film. In pre-baking, for example, heating is performed at a temperature of 90° C. for several minutes. Thickness of the coating film after solvent removal is preferably adjusted to be 10 to 200 micrometers, for example.

(3) Post-Baking Step

Post-baking is applied to the unhardened coating film preferably at 160 to 200° C. for 5 to 30 minutes, thereby allowing formation of a hardened coating film. The coating according to the invention is useful as a remote phosphor layer or the like.

A composition for an optical semiconductor, the composition containing the thermosetting composition according to the invention, is also one aspect of the invention. A light emitting device is sealed using the composition for the optical semiconductor according to the invention, thereby allowing manufacture of an optical semiconductor device.

The light emitting device is not particularly limited, and for example, in the case where the optical semiconductor device is a light emitting diode, specific examples include a product formed by laminating a semiconducting material onto a substrate. In the above case, specific examples of the semiconductor material include GaAs, GaP, GaAlAs, GaAsP, AlGaInP, GaN, InN, AlN, InGaAlN and SiC.

Specific examples of the substrates include sapphire, spinel, SiC, Si, ZnO and a GaN single crystal. Moreover, a buffer layer may be formed, when necessary, between the substrate and the semiconducting material. Specific examples of the buffer layer include GaN and AlN.

A method for laminating the semiconducting material on the substrate is not particularly limited, and specific examples include an MOCVD method, and an HDVPE method and a liquid-phase deposition method. Specific examples of structure of the light emitting device include homostructure and each having MIS junction, PN junction and PIN junction, and double heterostructure. Moreover, the device is formed into single or multiple quantum well structure.

In the case where the light emitting device is sealed using as the sealing agent the composition for the optical semiconductor according to the invention, any other sealing agent may be simultaneously used. In the above case, the light emitting device is sealed using the composition for the optical semiconductor according to the invention, and then a circumference thereof may be sealed with any other sealing agent, or the light emitting device is sealed with any other sealing agent, and then a circumference thereof may be sealed with the sealing agent for the optical semiconductor device according to the invention.

Any other sealing agent described above is not particularly limited, and specific examples include epoxy resin, silicone resin, acrylic resin, urea resin, imide resin, and glass. Moreover, by coating a liquid containing a surface modifier, a protective layer can be provided on a surface.

A method for sealing the light emitting device using the composition for the optical semiconductor according to the invention is not particularly limited, and specific examples include a method for preliminarily injecting the composition for the optical semiconductor according to the invention into a mold form, dipping a lead frame or the like to which the light emitting device is fixed, and then hardening the composition, and a method for injecting the composition for the optical semiconductor according to the invention into a form into which a light emitting device is inserted and then hardening the composition.

Specific examples of the method for injecting the composition for the optical semiconductor according to the invention include injection by a dispenser, transfer molding and injection molding. Furthermore, specific examples of other sealing methods include a method for adding dropwise the composition for the optical semiconductor according to the invention onto a light emitting device to coat the composition thereon by stencilling, screen printing and through a mask, thereby hardening the composition, and a method for injecting by a dispenser the composition for the optical semiconductor according to the invention into a cup on which bottom a light emitting device is arranged, thereby hardening the composition.

An optical semiconductor device including a composition for an optical semiconductor device according to the invention as a sealing agent is also one aspect of the invention.

EXAMPLES

The invention is explained in greater detail by way of Examples. In addition, the invention is not limited by the Examples described below.

Measurement of Number Average Molecular Weight and Weight Average Molecular Weight A number average molecular weight and a weight average molecular weight of a polymer synthesized in the invention were measured as described below. High performance liquid chromatograph system CO-2065plus made by JASCO Corporation was used, 20 microliters of THF solution of a sample having a concentration 1% by mass was used as an analytical sample, and measurement was carried out according to a GPC method under conditions of column: Shodex KF804L (made by Showa Denko K. K.) (two columns being connected in series), column temperature: 40° C., a detector: RI, an eluate: THF, and an eluate flow rate: 1.0 mL per minute to calculate a polystyrene equivalent, and thus the molecular weight was determined.

NMR (Nuclear Magnetic Resonance Spectrum)

NMR of 400 MHZ made by JEOL Datum Co., Ltd. was used, a measuring sample was dissolved into deuterated acetone or deuterated chloroform, and measurement was carried out.

Reagents or the like used in Examples were as described below.

DVTS (1,5-divinylhexamethyl trisiloxane): made by JNC Corporation.

FM-2205 (polydimethylsiloxane having vinyl groups at both ends and having a number average molecular weight of 700): made by JNC Corporation.

FM-2210 (polydimethylsiloxane having vinyl groups at both ends and having a number average molecular weight of 900): made by JNC Corporation.

MA-DGIC (monoallyldiglycidyl isocyanurate): made by Shikoku Chemicals Corporation.

DA-MGIC (diallylmonoglycidyl isocyanurate): made by Shikoku Chemicals Corporation.

MeDAIC (methyldiallyl isocyanurate): made by Shikoku Chemicals Corporation.

S210 (vinyltrimetoxysilane): made by JNC Corporation.

AGE (allyl glycidyl ether): made by Yokkaichi Chemical Company, Limited.

S510 (3-glycidoxypropyltrimetoxysilane): made by JNC Corporation

Synthesis Example 1

Synthesis of Silsesquioxane Derivative Base Polymer 1

Then, 300 g (0.230 mol) of double-decker silsesquioxane derivative (DD-4H) manufactured by a method disclosed in WO 2004/024741 A, 52.2 g (0.073 mol) of FM-2205(0.32-fold mole based on DD-4H), and 304 g of toluene as a solvent was put, the resulting mixture was heated to 120° C. to dissolve raw materials. Thereto, addition of Pt catalyst was made to be 0.006 ppm in Pt concentration based on DD-4H. The reaction mixture was subjected to heating stirring at 120° C. for 16 hours to allow a reaction.

Thereto, 256 g (0.985 mol) of DVTS (4.3-fold mole based on DD-4H) was added to further allow a reaction for 6 hours. The reaction mixture was cooled to room temperature, toluene and DVTS were distilled off under reduced pressure conditions of 1 mmHg at 70° C. by an evaporator to give a colorless transparent liquid having a viscosity (at 25° C.) of 100 Pa·s. Molecular weight analyzed by GPC was: number average molecular weight: Mn=1,400 and weight average molecular weight: Mw=3,400.

A solution prepared by mixing 1.23 g of product obtained and 0.615 g of benzyl alcohol as an internal standard material was subjected to H-NMR measurement (deuterated acetone solvent). A $^1$H-NMR chart of the product obtained is shown in FIG. 1.

When calculation was made, in data obtained, from each integral ratio and weight ratio with regard to 4.6 ppm (—CH$_2$—), 4.9 to 5.1 ppm (Si—H) and 5.6 to 6.4 ppm (—CH═CH$_2$), an SiH equivalent was 770 g/mol and a vinyl equivalent was 1,600 g/mol. When calculation was made using the numeric values, e, f and g satisfied equations: e=2.37, g=1.14, and f=0.24, respectively.

Here, a functional group equivalent was specified as described below.

SiH group equivalent: $H=(S/I)\times(M/A)\times 54$;

Vinyl group equivalent: $V=(S/I)\times(M/B)\times 18$.

Here, each character in a formula indicates a numeric value described below.
S: weight of a product;
I: weight of an internal standard material;
A: peak area of 4.9 to 5.1 ppm in H-NMR;
B: peak area of 5.6 to 6.4 ppm in H-NMR;
M: peak area of 4.6 ppm in H-NMR.

In addition, a ratio of a:b:c was calculated and determined from the SiH group equivalent, the vinyl group equivalent, and raw material charge weight described above.

$e=(V/H)\times(V+F)/(V-260)\times(1302/X)$.

$g=(X+F)/(V-260)\times(1302/X)$.

$f=(4-a-b)/2$.

Here, each character in the formula indicates a numeric value described below.
H: SiH group equivalent (g/mol);
V: vinyl group equivalent (g/mol);
F: weight (g) of diorganosiloxane having vinyl groups at both ends used for a synthesis;
X: weight of DD-4H used for a synthesis.

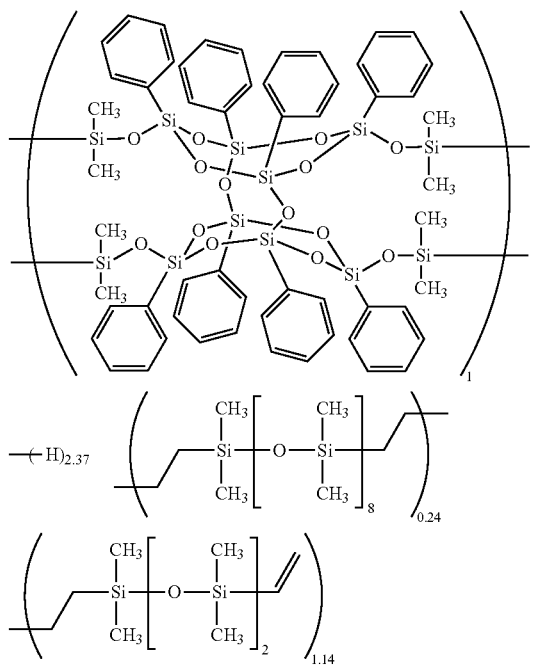

Formula 60

Synthesis Example 2

Synthesis of Silsesquioxane Derivative Base Polymer 2

Then, 780 g (0.6 mol) of DD-4H, 800 g (3.1 mol) of DVTS and 650 g of toluene as a solvent was put, heating stirring was performed under a nitrogen atmosphere. After the contents reached 115° C., a Karstedt catalyst was added to be 0.006 ppm in Pt concentration based on DD-4H, and the reaction mixture was subjected to heating stirring.

Tracing of the reaction was performed by GPC, and heating was stopped after 10 hours to terminate the reaction. The reaction mixture was transferred to a recovery flask, and toluene and extra DVTS were distilled off under reduced pressure conditions of 1 mmHg at 70° C. by an evaporator to give 1,043 g of colorless transparent liquid having a viscosity (25° C.) of 70 Pa·s. Molecular weight analyzed by GPC was: number average molecular weight: Mn=1,400 and weight average molecular weight: Mw=1,700.

Figure 2:
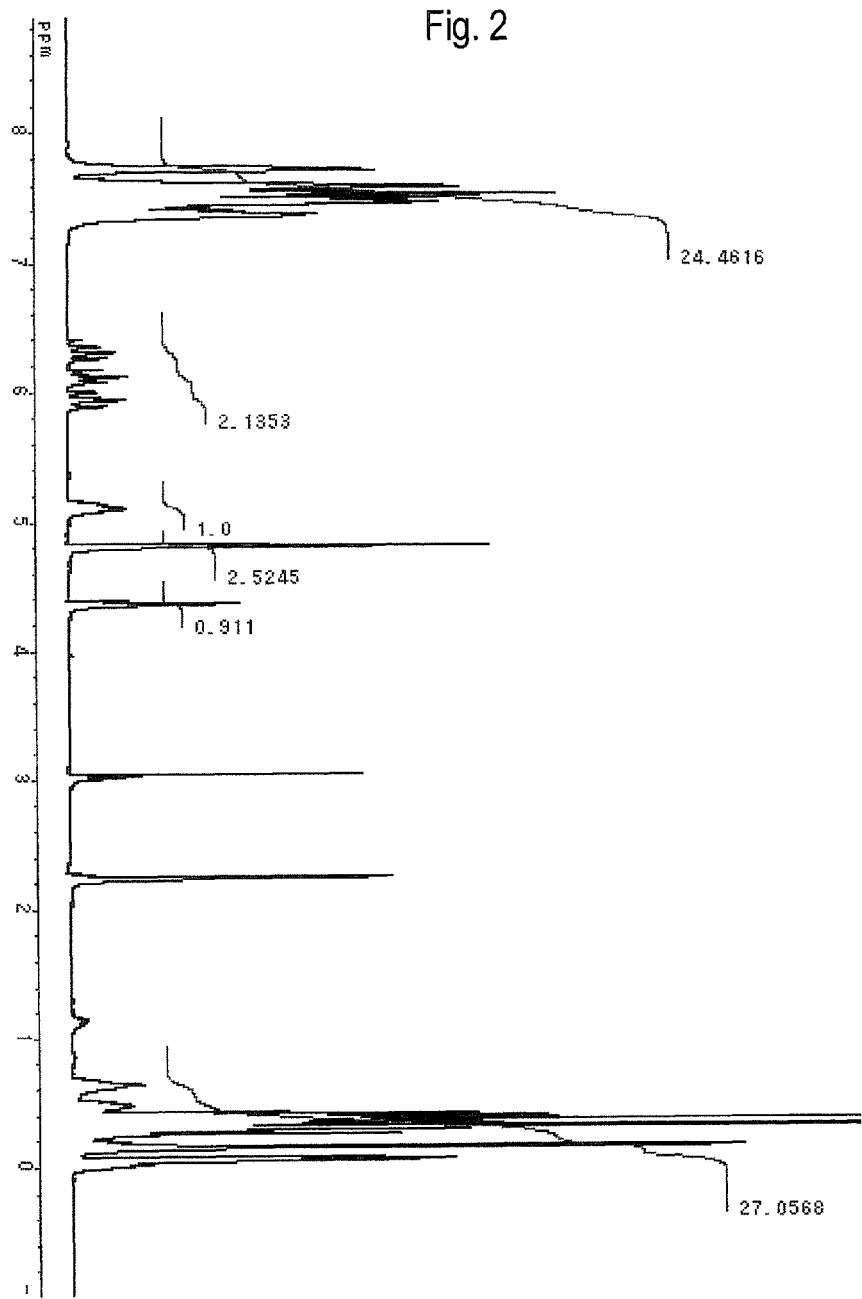
FIG. 2 shows a $^1$H-NMR chart of silsesquioxane derivative base polymer 2 obtained in Synthesis Example 2.

A solution prepared by mixing 0.107 g of product obtained and 0.0196 g of benzyl alcohol as an internal standard material was subjected to H-NMR measurement (deuterated acetone solvent). A $^1$H-NMR chart of the product obtained is shown in FIG. 2.

When calculation was made, in data obtained, from each integral ratio and weight ratio with regard to 4.6 ppm (—CH$_2$—), 4.9 to 5.1 ppm (Si—H) and 5.6 to 6.4 ppm (—CH═CH$_2$), an SiH equivalent was 741 g/mol and a vinyl equivalent was 1,042 g/mol. When calculation was made using the numeric values, e, f and g satisfied equations: e=2.34, g=0, and f=1.66, respectively.

Formula 61

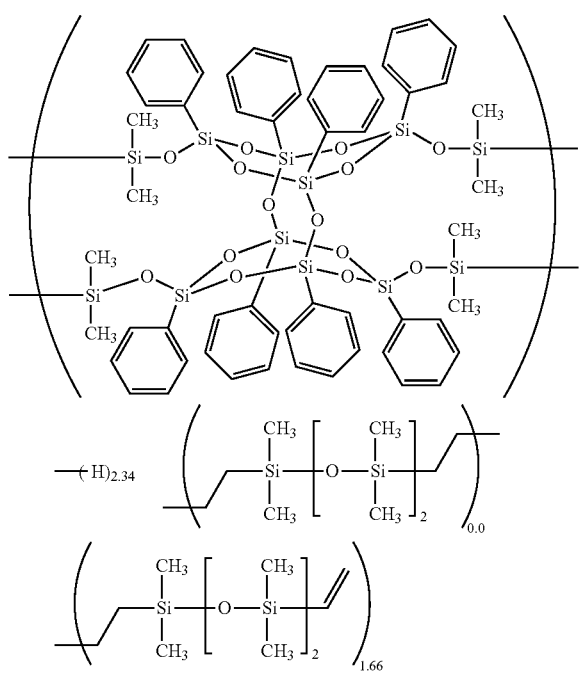

Synthesis Example 3

A porcelain stirrer, a cooling tube and a thermometer were attached to a 300 mL four-necked flask, 85.9 g (0.462 mol) of 1,1,3,3-divinyltetramethyldisiloxane, 74.8 g (0.462 mol) of hexamethyldisiloxane, 91.2 g (0.308 mol) of octamethylcyclotetrasiloxane and 2.0 g of activated clay as an acid catalyst were charged into the flask. Temperature was increased to 80° C. to allow a reaction for 3 hours, and a product was obtained by a reaction formula described below.

Cooling was made to room temperature and activated clay was removed by filtration using 5C filter paper. Thus, 247 g of colorless transparent liquid was obtained. When Si-NMR was measured, a ratio of a peak integral value of a trimethylsilyl group:a peak integral value of a vinyldimethylsilyl group:a peak integral value of a dimethylsiloxane unit was 1:1:1.34.

From the measurement, a vinyl group equivalent of the product was calculated to be 274 g/mol. The product was a mixture of compound a, compound b and compound c, and from a probability theory, a ratio of compound a, compound b and compound c is 1:2:1. The vinyl group equivalent refers to a value in the mixture as a whole.

Formula 62

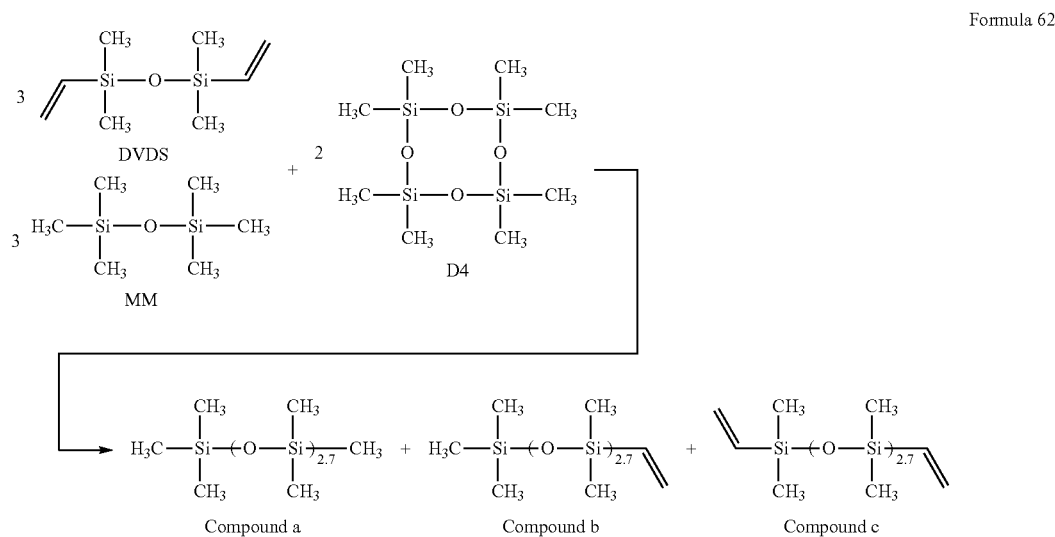

Example 1

Synthesis of Compound 1

According to the reaction formula below, compound 1 was synthesized, in which, in the formula (1) above, the number of groups is: A {formula (a)}=1.32, B {formula (b-i)}=1.30, 2C {formula (c-i)}=1.38, and D {formula (d)}=0.

Formula 63

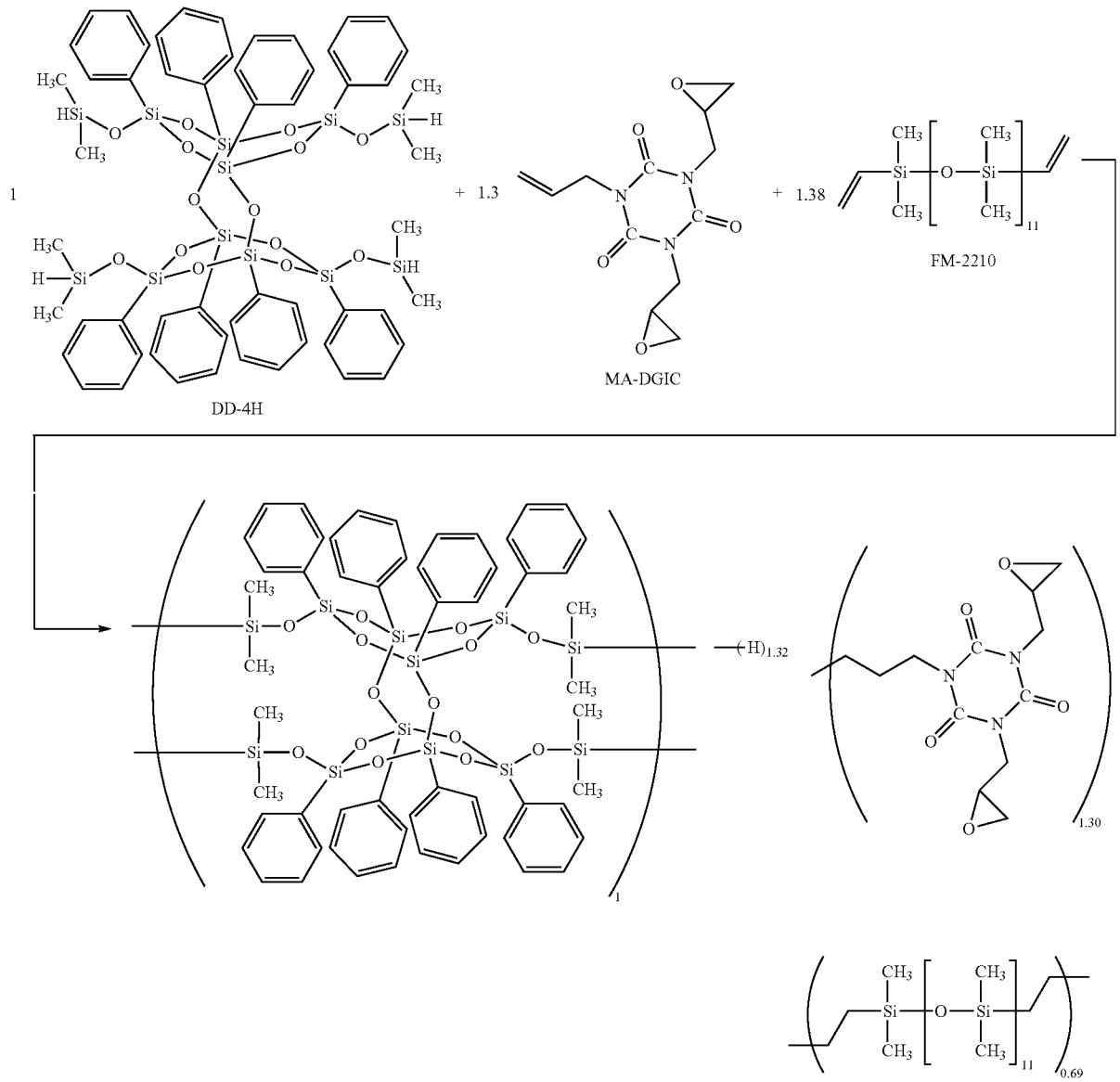

Into a 300 mL (internal volume) reaction vessel equipped with a thermometer, a reflux condenser and a stirrer, 50 g (0.0384 mol) of DD-4H, 23.8 g (0.0265 mol) of vinyl silicone (FM-2210), 14.96 g (0.05 mol) of monoallyldiepoxy isocyanurate (MA-DGIC), and 50 g of toluene as a solvent were put.

Under a nitrogen atmosphere, heating stirring was started. After the contents reached 90° C., addition of Pt catalyst was made in an amount to be 1 ppm in Pt concentration based on DD-4H, and heating stirring was performed as was for 5 hours. Disappearance of MA-DGIC was confirmed by GC to terminate the reaction. Cooling was made to room temperature, and then 1.6 g of activated carbon was added to perform stirring 3 hours or more, and then activated carbon was removed by filtration. A filtrate was put into an evaporator, and toluene being the solvent was distilled off under reduced pressure conditions of 1 mmHg at 90° C. to give 81 g of colorless transparent liquid in a starch syrup state.

Molecular weight analyzed by GPC was: number average molecular weight: Mn=4,300 and weight average molecular weight: Mw=18,700. A $^1$H-NMR chart of the product obtained is shown in FIG. 3.

Figure 3:
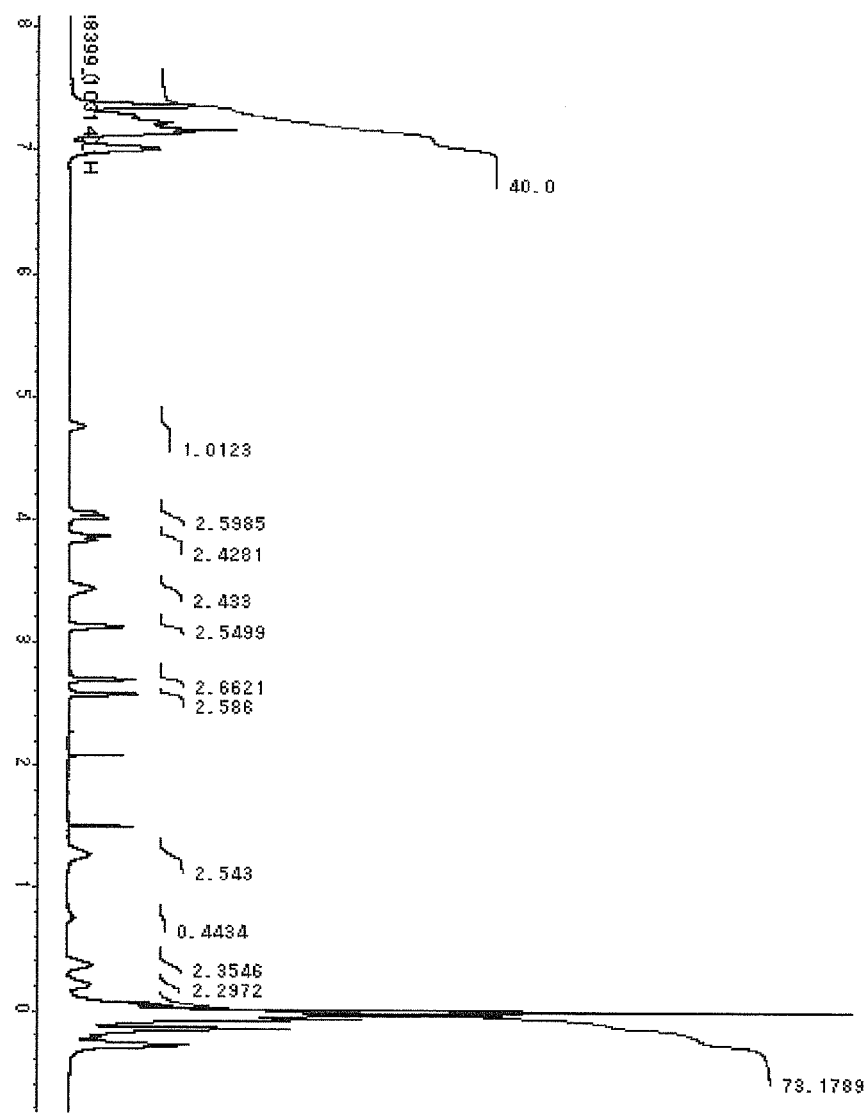
FIG. 3 shows a $^1$H-NMR chart of compound 1 obtained in Example 1.

As shown in FIG. 3, compound 1 was found to have an epoxy group, an isocyanuric ring skeleton, an alkoxysilyl group (methoxysilyl group) and also an SiH group.

Example 2

Synthesis of Compound 2

According to the reaction formula below, compound 2 was synthesized, in which, in the formula (1) above, the number of groups is: A {formula (a)}=1.32, B {formula (b-i)}=0.65, 2C {formula (c-i)}=1, and D=0.65.

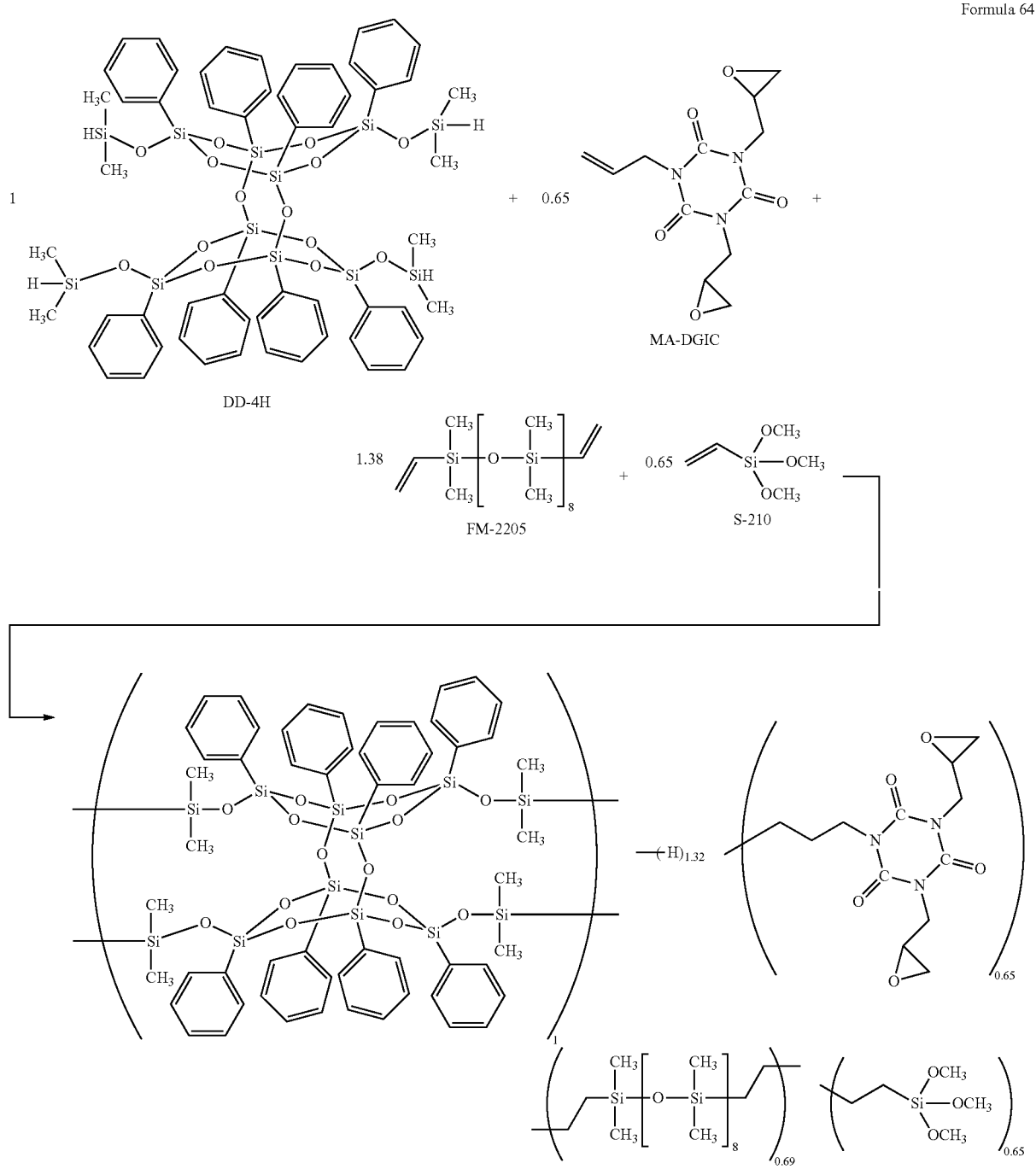

Formula 64

Into a 300 mL (internal volume) reaction vessel equipped with a thermometer, a reflux condenser and a stirrer, 50 g of silsesquioxane derivative (DD-4H), 18.6 g (0.0266 mol) of vinyl silicone (FM-2205), 7.47 g (0.0252 mol) of monoallyldiepoxy isocyanurate (MA-DGIC), 3.7 g (0.0252 mol) of S210, and 50 g of toluene as a solvent were put.

Under a nitrogen atmosphere, heating stirring was started. After the contents reached 90° C., addition of Pt catalyst was made in an amount to be 1 ppm in Pt concentration based on DD-4H, and heating stirring was performed as was for 5 hours. Disappearance of MA-DGIC was confirmed by GC to terminate the reaction. Cooling was made to room temperature, and then 1.6 g of activated carbon was added to perform stirring 3 hours or more, and then activated carbon was removed by filtration. A filtrate was put into an evaporator, and toluene being the solvent was distilled off under reduced pressure conditions of 1 mmHg at 90° C. to give 41 g of colorless transparent liquid in a starch syrup state.

Molecular weight of the resulting product analyzed by GPC was: number average molecular weight: Mn=3,900 and weight average molecular weight: Mw=18,200. A $^1$H-NMR chart of the product obtained is shown in FIG. 4.

Figure 4:
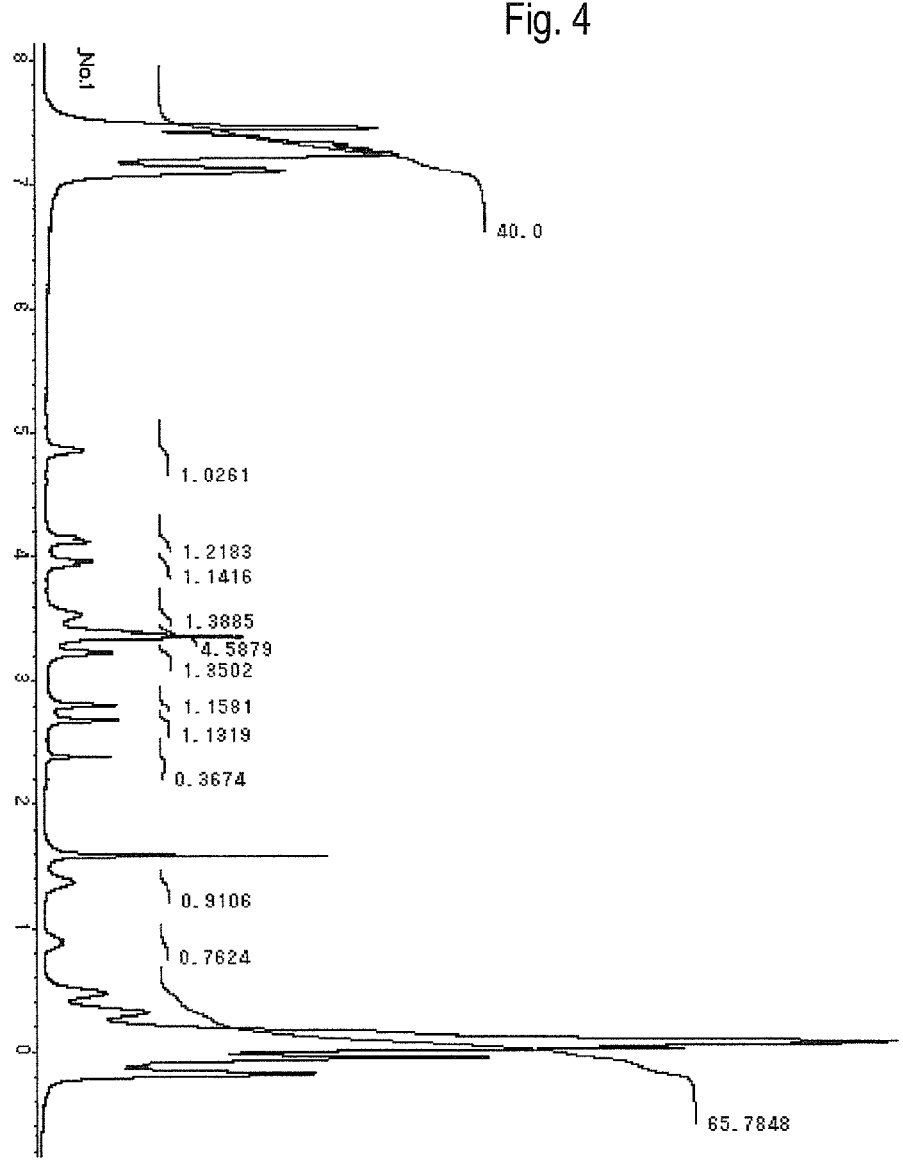
FIG. 4 shows a $^1$H-NMR chart of compound 2 obtained in Example 2.

As shown in FIG. 4, compound 2 was found to have an epoxy group, an isocyanuric ring skeleton, an alkoxysilyl group (methoxysilyl group) and also an SiH group.

Example 3

Synthesis of Compound 3

According to the reaction formula below, compound 3 was synthesized, in which, in the formula (1) above, the number of groups is: A {formula (a)}=1.32, B {formula (b-i)}=0.65, 2C {formula (c-i)}=0.69, 2C {formula (c-ii)}=0.69, and D=0.65.

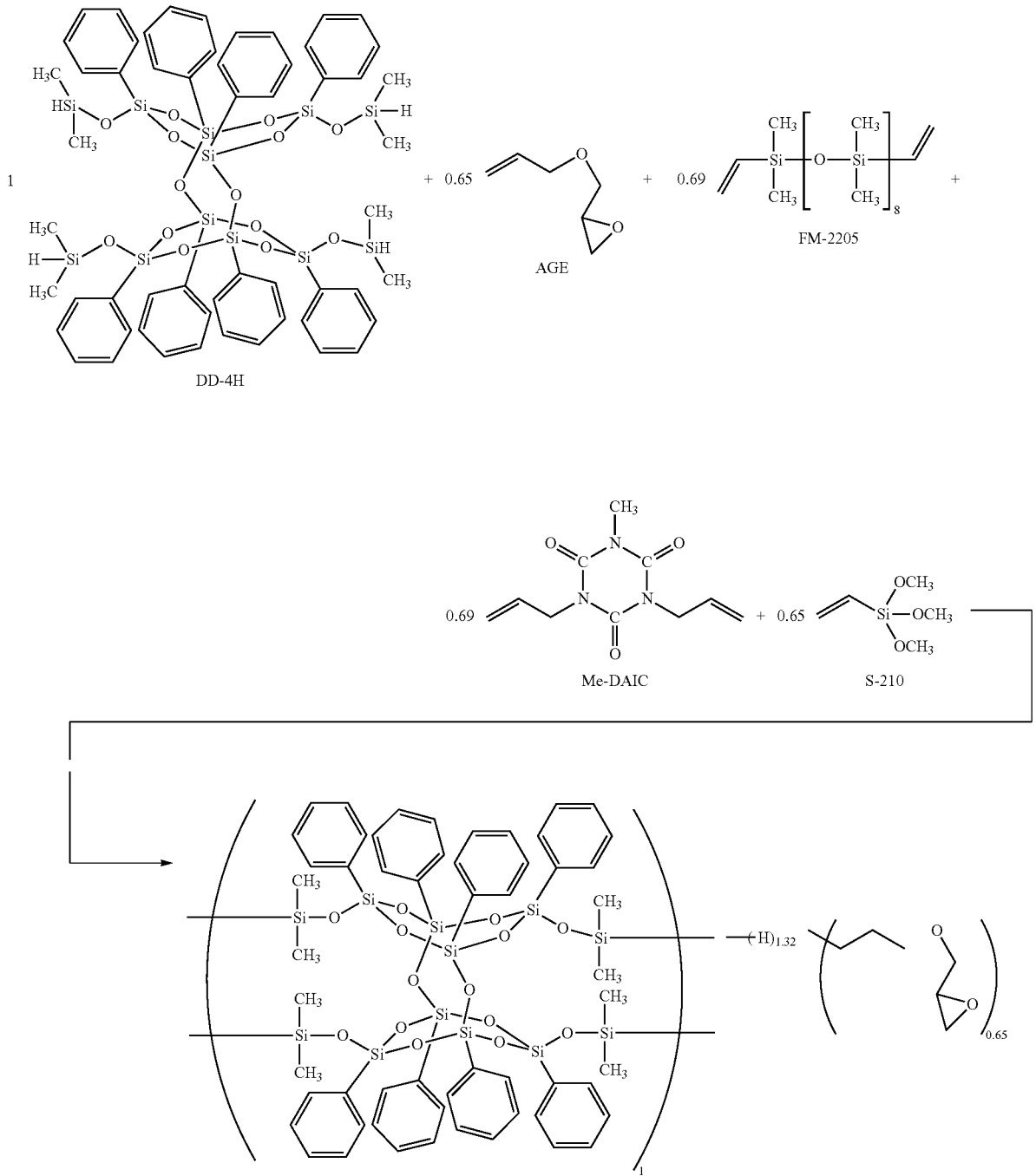

Formula 65

-continued

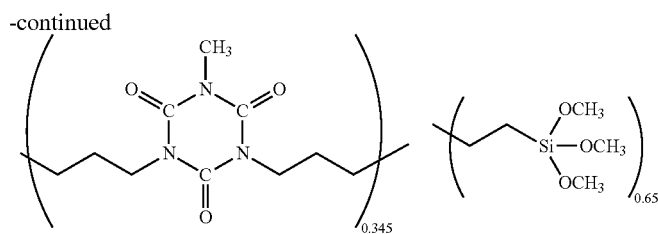

A synthesis was made to give 30 g of colorless transparent solid in a manner identical with the procedures in Example 1 except that change was for DD-4H to 25 g (0.0192 mol), vinyl silicone (FM-2205) to 4.634 g (0.0066 mol), methyldiallyl isocyanurate (MeDAIC) to 1.478 g (0.0066 mol), AGE to 1.42 g (0.0125 mol), 5210 to 1.847 g (0.0125 mol), and toluene as the solvent to 30 g. In addition, disappearance of MeDAIC was confirmed by GC herein to terminate the reaction.

Molecular weight of the resulting product analyzed by GPC was: number average molecular weight: Mn=2,000, and weight average molecular weight: Mw=4,200. A $^1$H-NMR chart of the product obtained is shown in FIG. 5.

Figure 5:
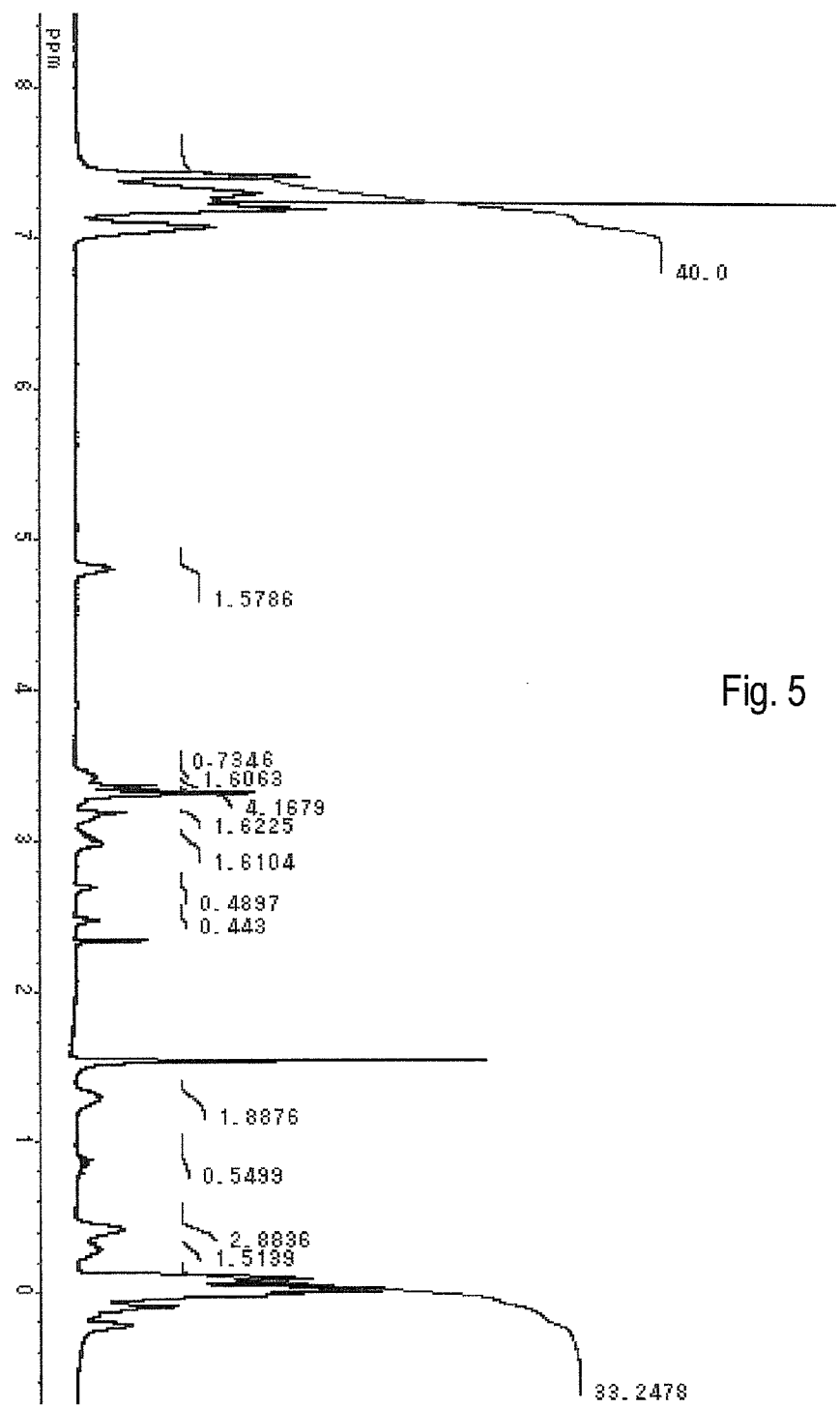
FIG. 5 shows a $^1$H-NMR chart of compound 3 obtained in Example 3.

As shown in FIG. 5, compound 3 was found to have an epoxy group, an isocyanuric ring skeleton, an alkoxysilyl group (methoxysilyl group) and also an SiH group.

Example 4

Synthesis of Compound 4

According to the reaction formula below, compound 4 was synthesized, in which, in the formula (1) above, the number of groups is: A {formula (a)}=2.526, 2C {formula (c-i)}=0.345, 2C {formula (c-ii)}=0.478, and D=0.65.

Formula 66

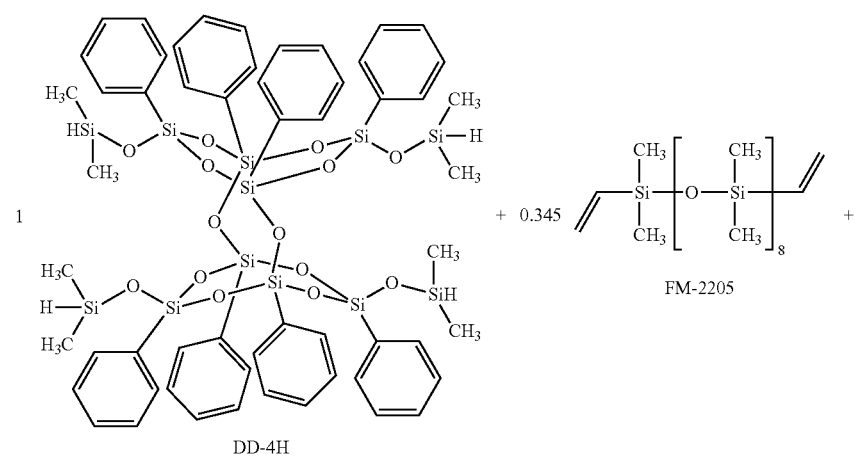

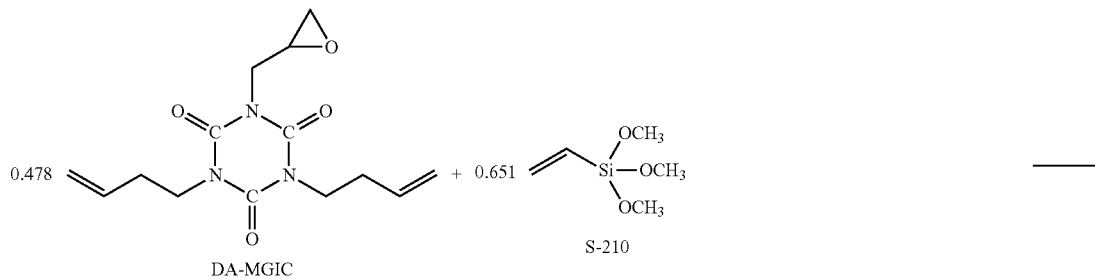

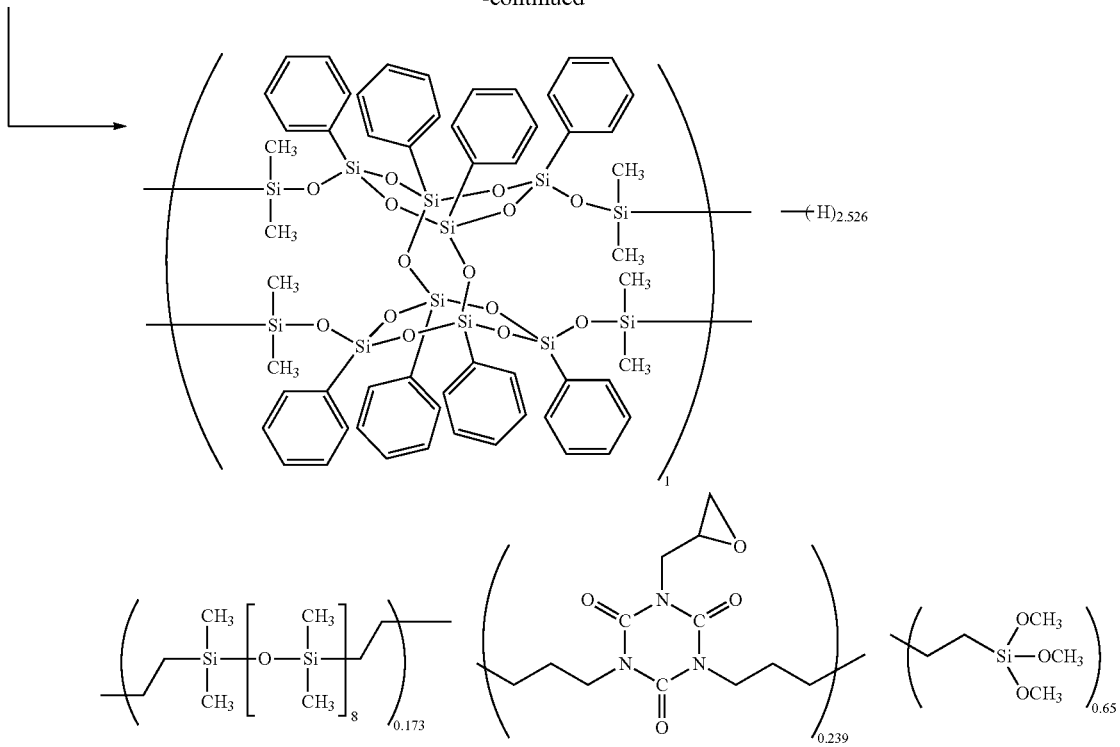

A synthesis was made to give 64 g of colorless transparent solid in a manner identical with the procedures in Example 1 except that change was for DD-4H to 25 g (0.0192 mol), vinyl silicone (FM-2205) to 4.634 g (0.0066 mol), diallyldiepoxy isocyanurate (DA-MGIC) to 2.58 g (0.00917 mol), S210 to 1.847 g (0.0125 mol), and toluene as the solvent to 30 g. In addition, disappearance of DA-MGIC was confirmed by GC herein to terminate the reaction.

Molecular weight of the resulting product analyzed by GPC was: number average molecular weight: Mn=4,100, and weight average molecular weight: Mw=19,000. A $^1$H-NMR chart of the product obtained is shown in FIG. 6.

Figure 6:
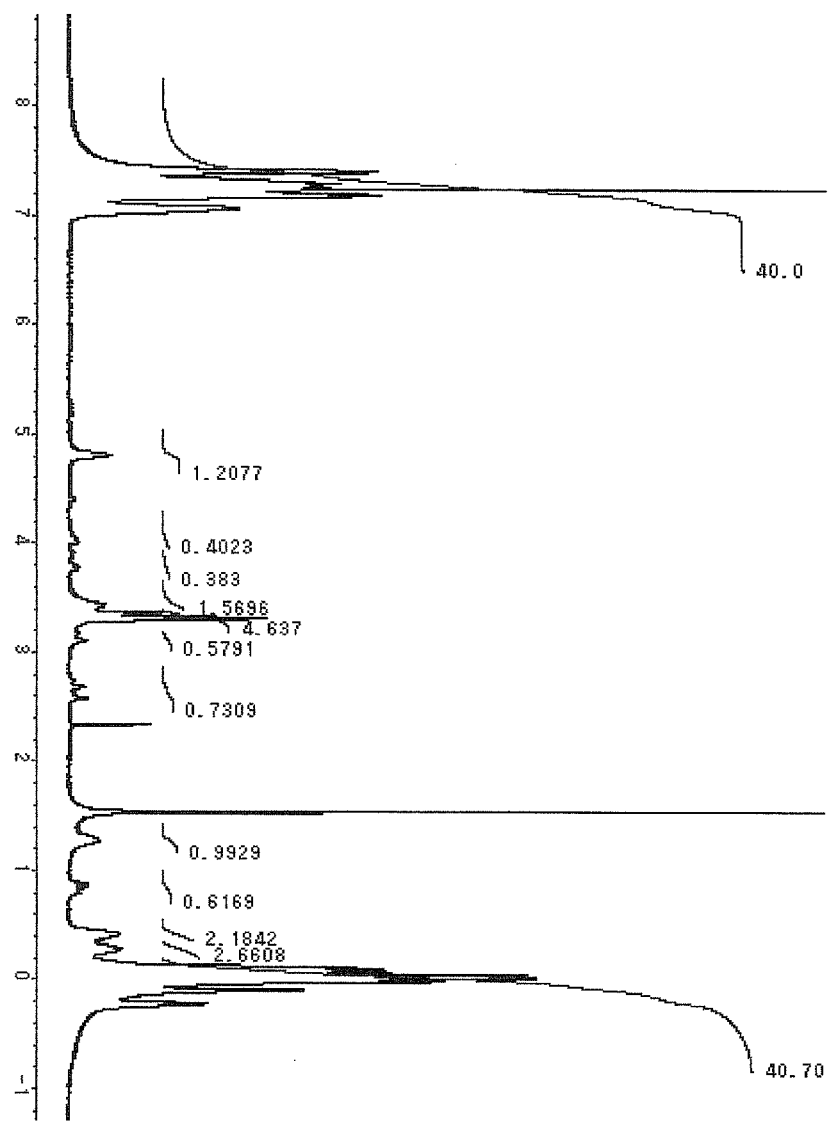
FIG. 6 shows a $^1$H-NMR chart of compound 4 obtained in Example 4.

As shown in FIG. 6, compound 4 was found to have an epoxy group, an isocyanuric ring skeleton, an alkoxysilyl group (methoxysilyl group) and also an SiH group.

Comparative Synthesis Example 1

Synthesis of Comparative Compound 1

According to the reaction formula below, comparative compound 1 was synthesized, in which, in the formula (1) above, the number of groups is: A {formula (a)}=1.32, B {formula (b-i)}=1.30, 2C {formula (c-i)}=1.38, and D {formula (d)}=0.

Formula 67

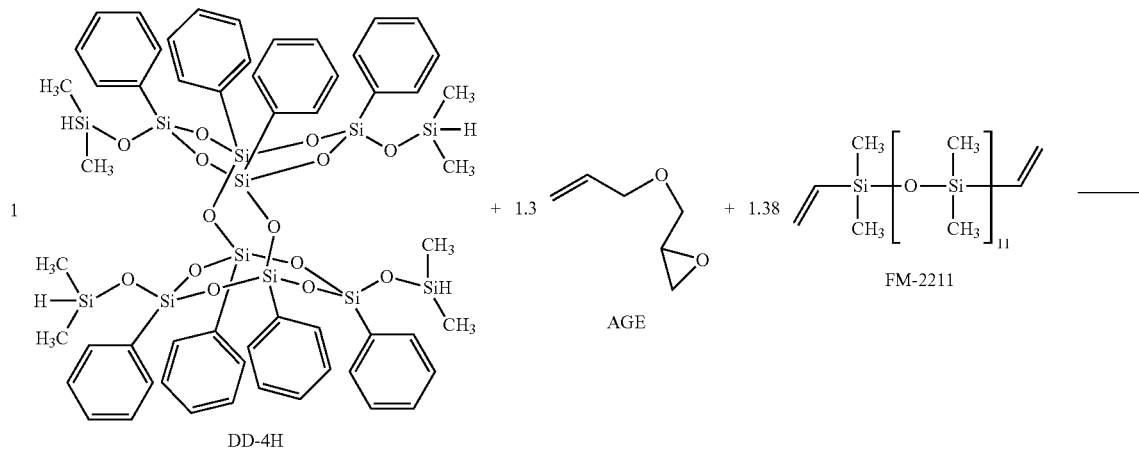

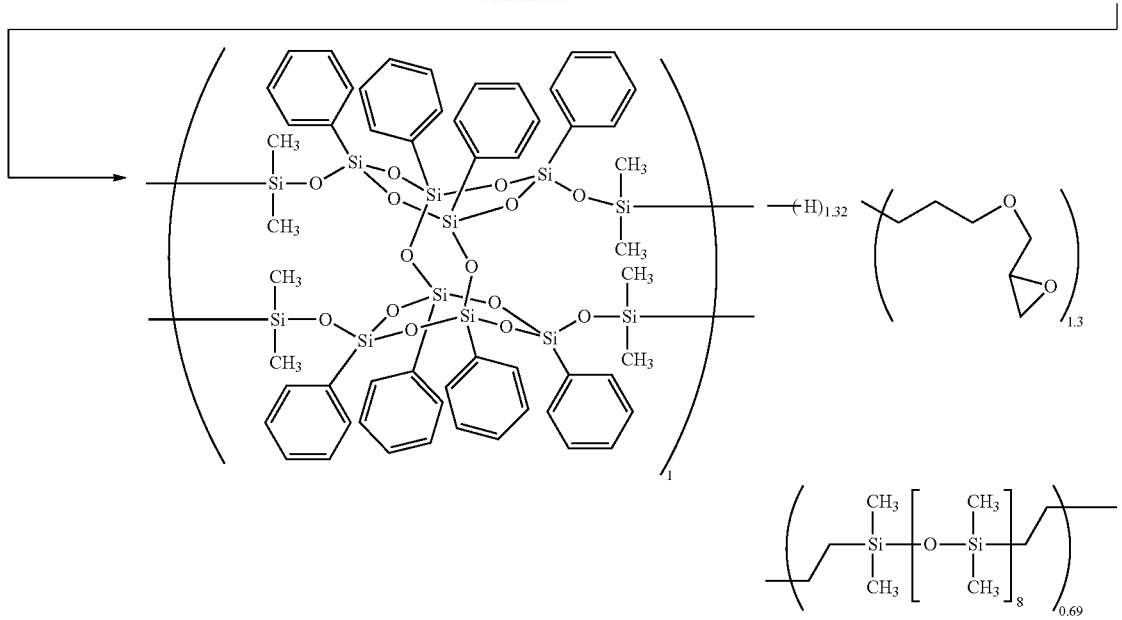

A synthesis was made to give 78 g of colorless transparent solid in a manner identical with the procedures in Example 1 except that change was for DD-4H to 50 g (0.0384 mol), vinyl silicone (FM-2210) to 23.8 g (0.0265 mol), AGE to 5.7 g (0.05 mol), and toluene as the solvent to 50 g.

Figure 7:
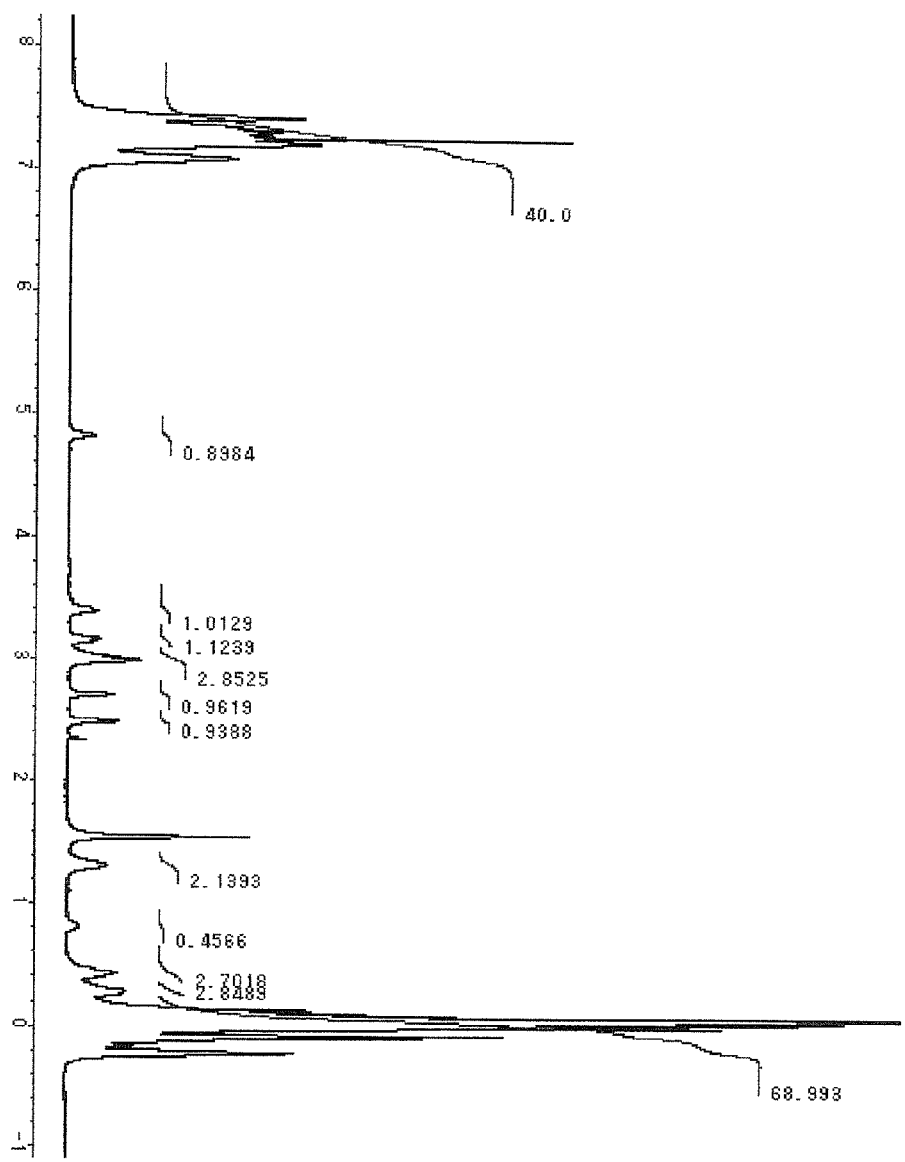
FIG. 7 shows a $^1$H-NMR chart of comparative compound 1 obtained in Comparative Synthesis Example 1.

Molecular weight of the resulting product analyzed by GPC was: number average molecular weight: Mn=5,000, and weight average molecular weight: Mw=29,800. A $^1$H-NMR chart of the product obtained is shown in FIG. 7.

Comparative Synthesis Example 2

Synthesis of Comparative Compound 2

According to the reaction formula below, comparative compound 2 was synthesized, in which, in the formula (1) above, the number of groups is: A {formula (a)}=1.97, B {formula (b-i)}=0, 2C {formula (c-i)}=0.69, 2C {formula (c-ii)}=0.69, and D {formula (d)}=0.65.

Formula 68

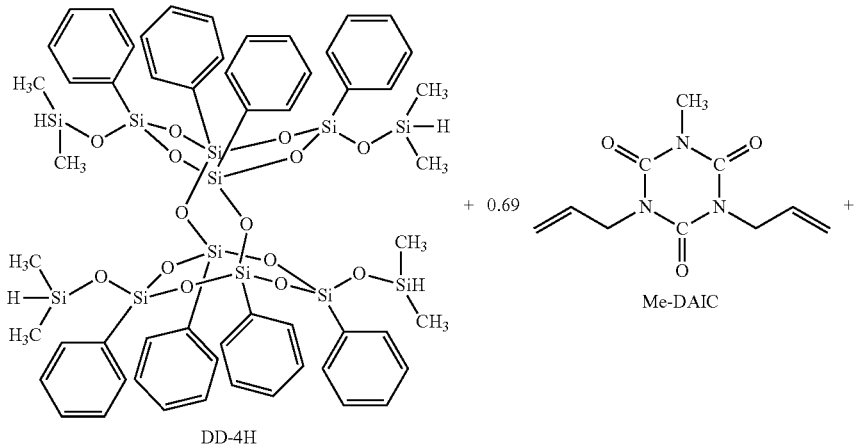

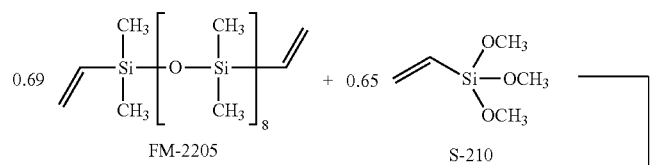

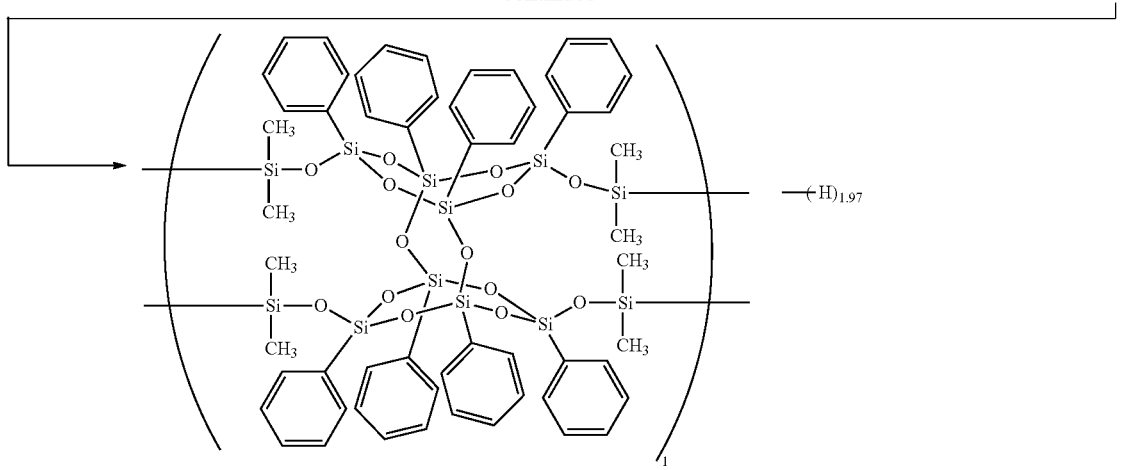

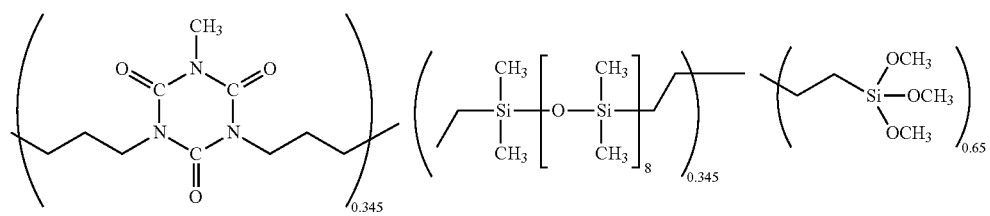

A synthesis was made to give 32 g of colorless transparent solid in a manner identical with the procedures in Example 1 except that change was for DD-4H to 25 g (0.0192 mol), vinyl silicone (FM-2205) to 4.634 g (0.0066 mol), methyldiallyl isocyanurate (MeDAIC) to 2.047 g (0.0092 mol), S210 to 1.847 g (0.0125 mol), and toluene as the solvent to 30 g. In addition, disappearance of MeDAIC was confirmed by GC herein to terminate the reaction.

Figure 8:
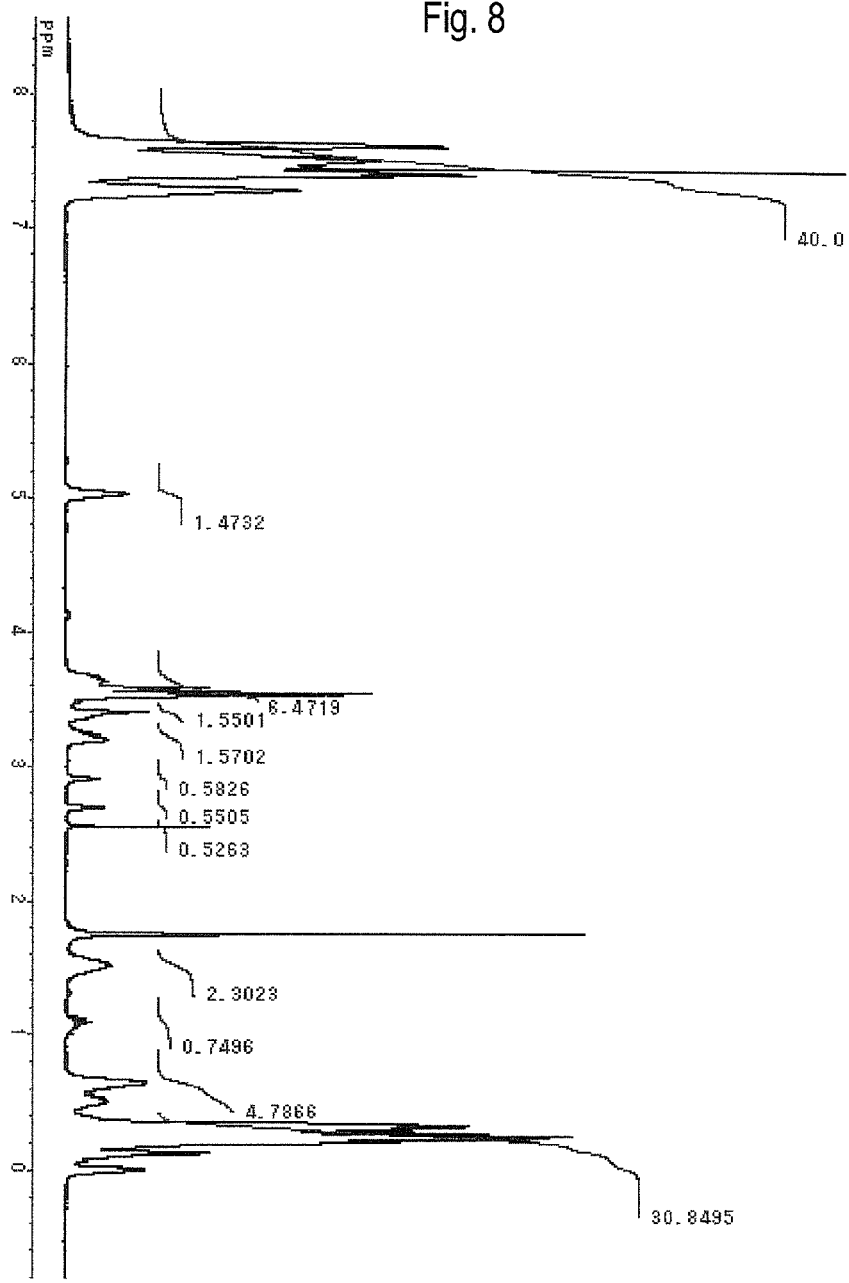
FIG. 8 shows a $^1$H-NMR chart of comparative compound 2 obtained in Comparative Synthesis Example 2.

Molecular weight of the resulting product analyzed by GPC was: number average molecular weight: Mn=5,000, and weight average molecular weight: Mw=29,800. A $^1$H-NMR chart of the product obtained is shown in FIG. 8.

Synthesis Example 3

Synthesis of SiH Silicone (1) . . .
M'M'/D'4/D4=1/1/1

Into a 300 mL three-necked flask, activated clay (1.6 g), 1,1,3,3-tetramethyldisiloxane (M'M', 27 g), octamethylcyclotetrasiloxane (D4, 59 g), 1,3,5,7-tetramethyl cyclotetrasiloxane (D'4, 49 g) were put, and the resulting mixture was heated in an oil bath at 90° C., while being stirred, and allowed to react for 18 hours. The reaction mixture was cooled to room temperature and activated clay was removed by filtration under reduced pressure. A low-boiling portion of the filtrate was removed under conditions of 70° C./1 Torr to give a colorless liquid product. According to $^1$H-NMR measurement, the product was confirmed to be a target SiH silicone compound.

Synthesis Example 4

Synthesis of SiH Silicone (2) . . .
M'M'/D'4/D4=1/1/3

A synthesis was made in a manner similar to the procedures described above except that 178 g of D4 was used.

Example 5

Synthesis of Compound 5

According to the reaction formula below, compound 5 was synthesized, in which, in the formula (2) above, the number of groups is: A {formula (a)}=0.5, B {formula (b-i)}=0.25, and D {formula (d)}=0.25.

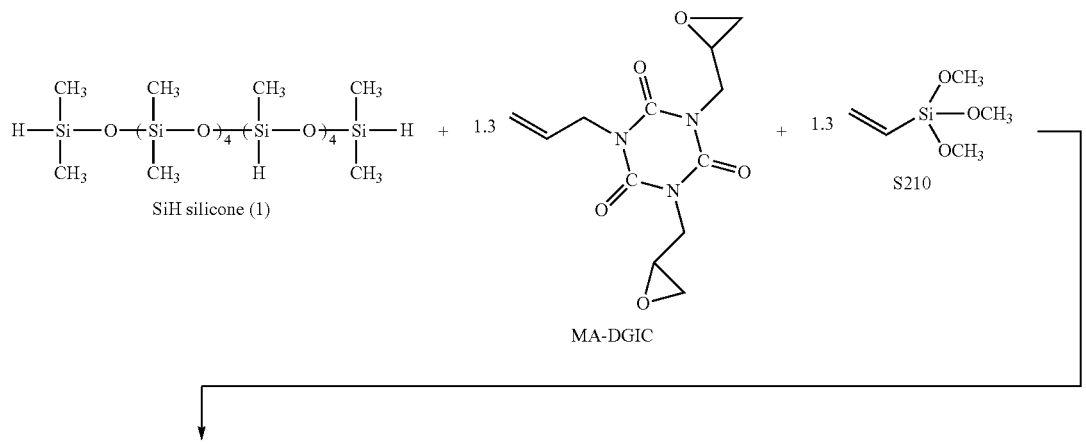

Formula 69

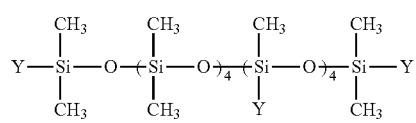

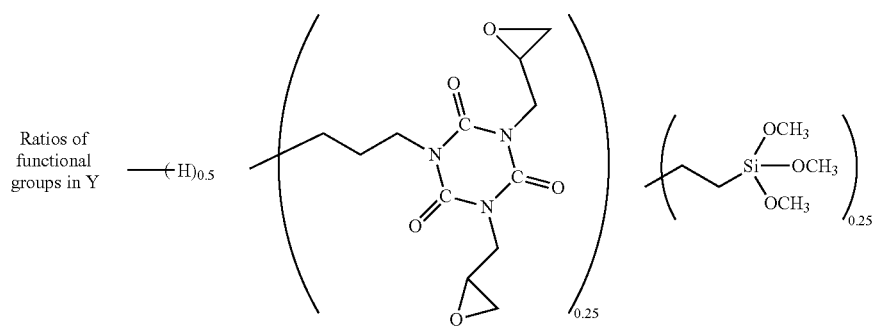

Into a 100 mL three-necked flask, SiH silicone (1) and (13 g) obtained in Synthesis Example 3, 7.0 g (0.0236 mol) of MA-DGIC, and toluene (13 g) were put, and the resulting mixture was heated in an oil bath at 90° C., while being stirred. A Karstedt catalyst (0.3% concentration, 13 microliters) was added into the mixture.

The reaction was continued at the temperature, and after 1 hour, 3.7 g (0.025 mol) of vinyltrimethoxysilane was further added and allowed to react. The reaction was further continued for 30 minutes at the temperature. The reaction mixture was cooled to room temperature, and 0.5 g of activated carbon added thereto and stirred overnight. Then, the mixture was filtered under pressure. The filtrate was heated under pressure, and toluene was removed to give a colorless liquid.

Figure 9:
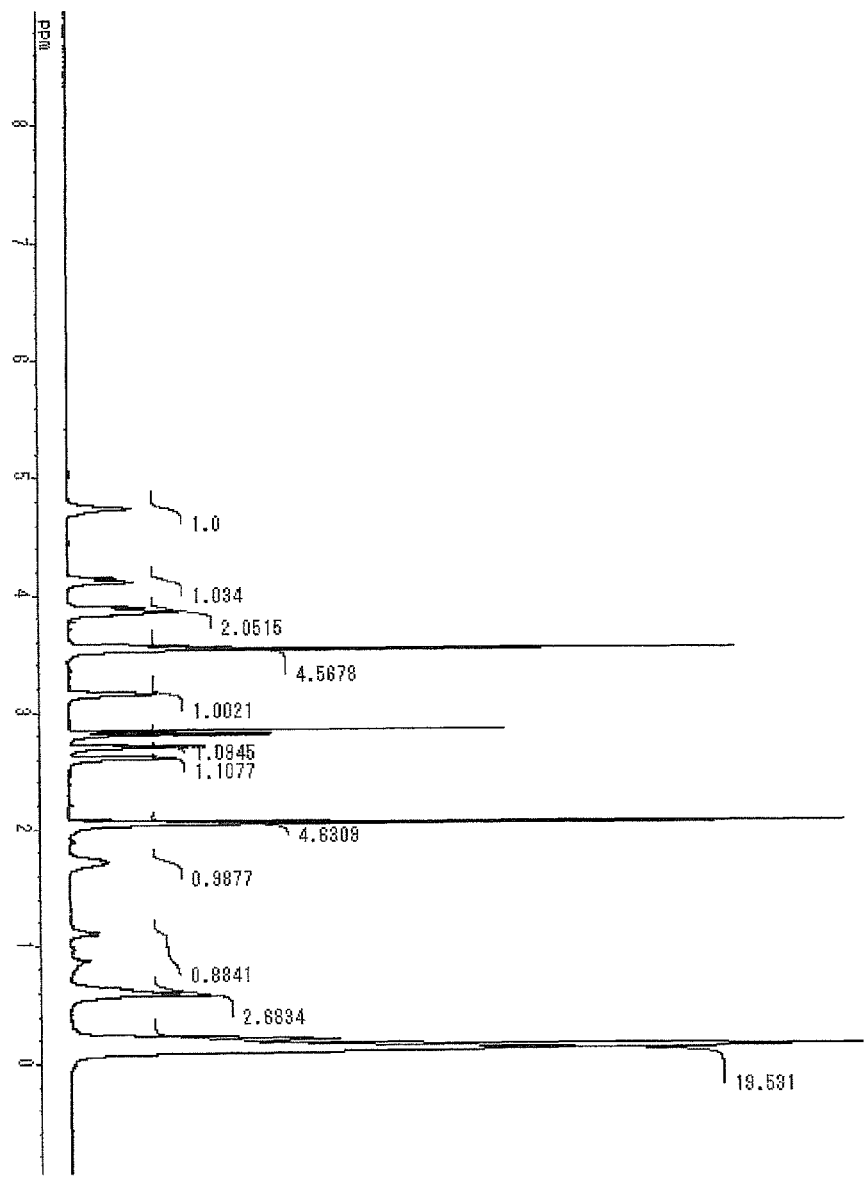
FIG. 9 shows a $^1$H-NMR chart of compound 5 obtained in Example 5.

Molecular weight of the resulting product analyzed by GPC was: number average molecular weight: Mn=1,900, and weight average molecular weight: Mw=2,600. A $^1$H-NMR chart of the product obtained is shown in FIG. 9.

Example 6

Synthesis Compound 6

According to the reaction formula below, compound 6 was synthesized, in which, in the formula (2) above, the number of groups is: A {formula (a)}=0.625, B {formula (b-i)}=0.125, and D {formula (d)}=0.25.

Formula 70

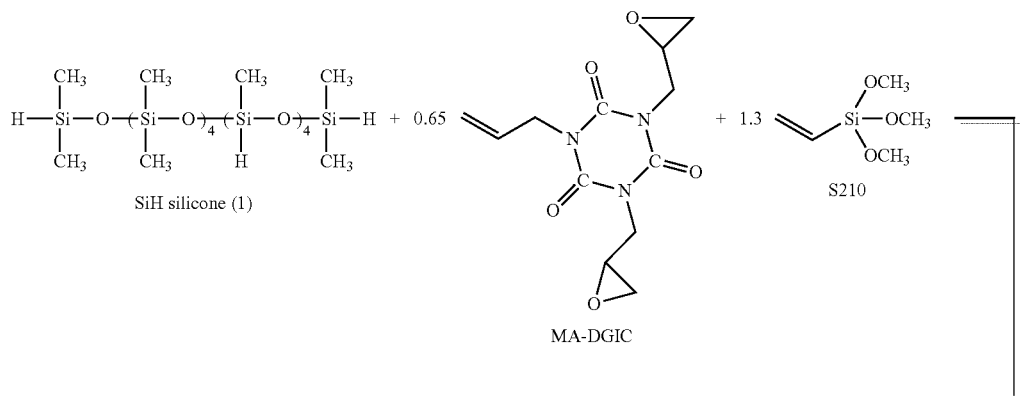

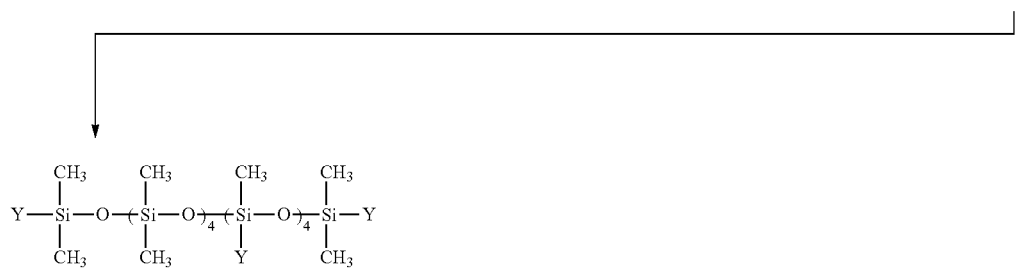

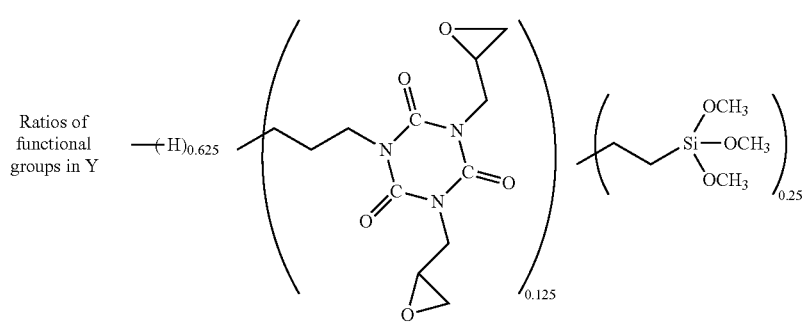

Compound 6 was obtained in a manner identical with the procedures in the synthesis of compound 5 except that 3.5 g of MA-DGIC was used.

Figure 10:
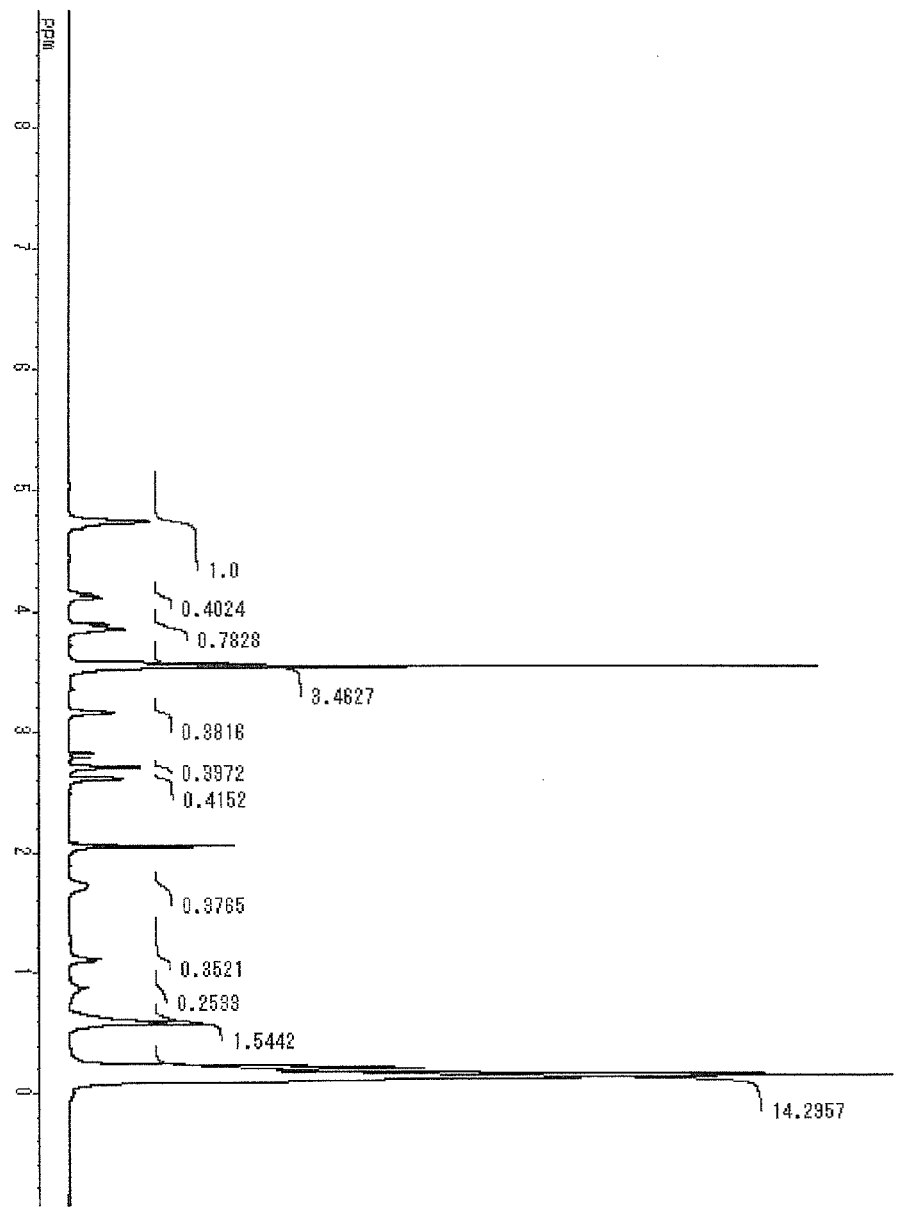
FIG. 10 shows a $^1$H-NMR chart of compound 6 obtained in Example 6.

Molecular weight of the resulting product analyzed by GPC was: number average molecular weight: Mn=1,800, and weight average molecular weight: Mw=2,400. A $^1$H-NMR chart of the product obtained is shown in FIG. 10.

Example 7

Synthesis Compound 7

According to the reaction formula below, compound 7 was synthesized, in which, in the formula (2) above, the number of groups is: A {formula (a)}=0.5, B {formula (b-i)}=0.25, and D {formula (d)}=0.25.

Formula 71

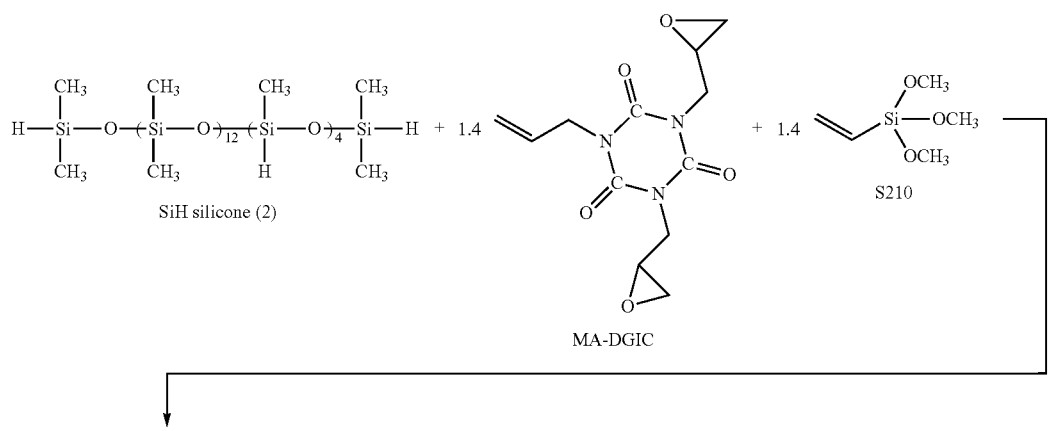

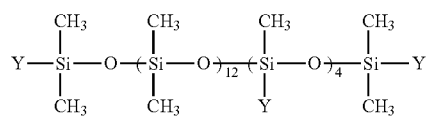

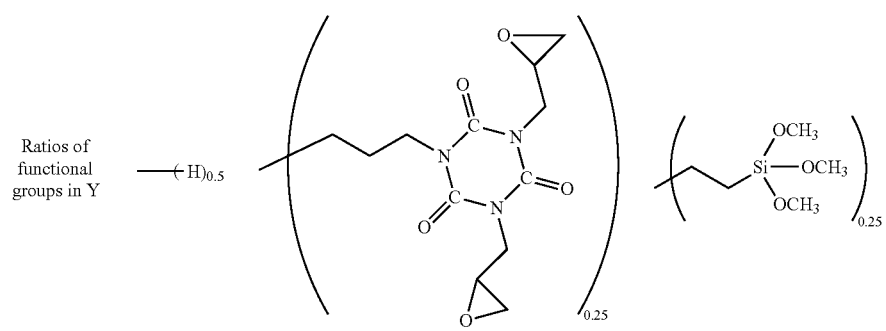

Compound 7 was obtained in a manner identical with the procedures in the synthesis of compound 7 except that SiH silicone (2) (23 g) was used in place of SiH silicone (1).

Figure 11:
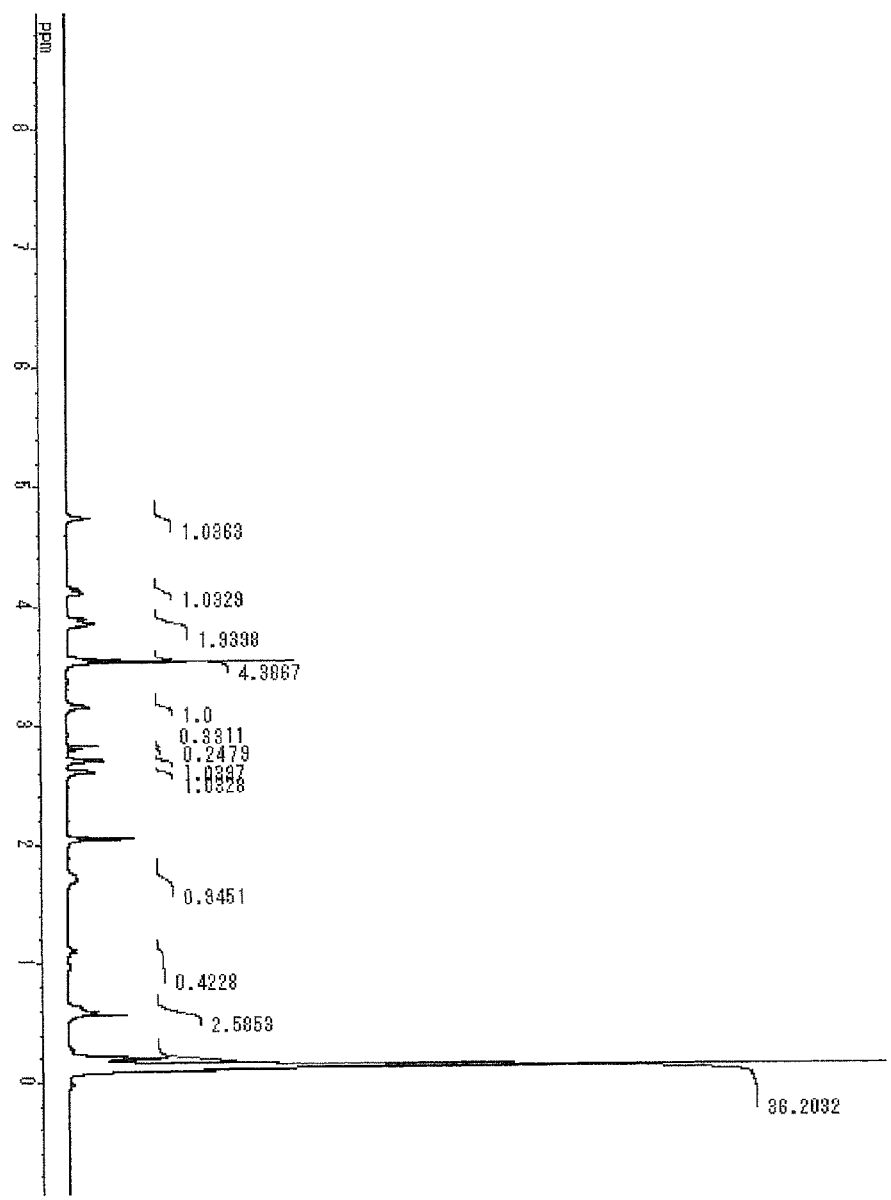
FIG. 11 shows a $^1$H-NMR chart of compound 7 obtained in Example 7.

Molecular weight of the resulting product analyzed by GPC was: number average molecular weight: Mn=2,400, and weight average molecular weight: Mw=4,100. A $^1$H-NMR chart of the product obtained is shown in FIG. 11.

Example 8

Synthesis Compound 8

According to the reaction formula below, compound 8 was synthesized, in which, in the formula (2) above, the number of groups is: A {formula (a)}=0.625, B {formula (b-i)}=0.125, and D {formula (d)}=0.25.

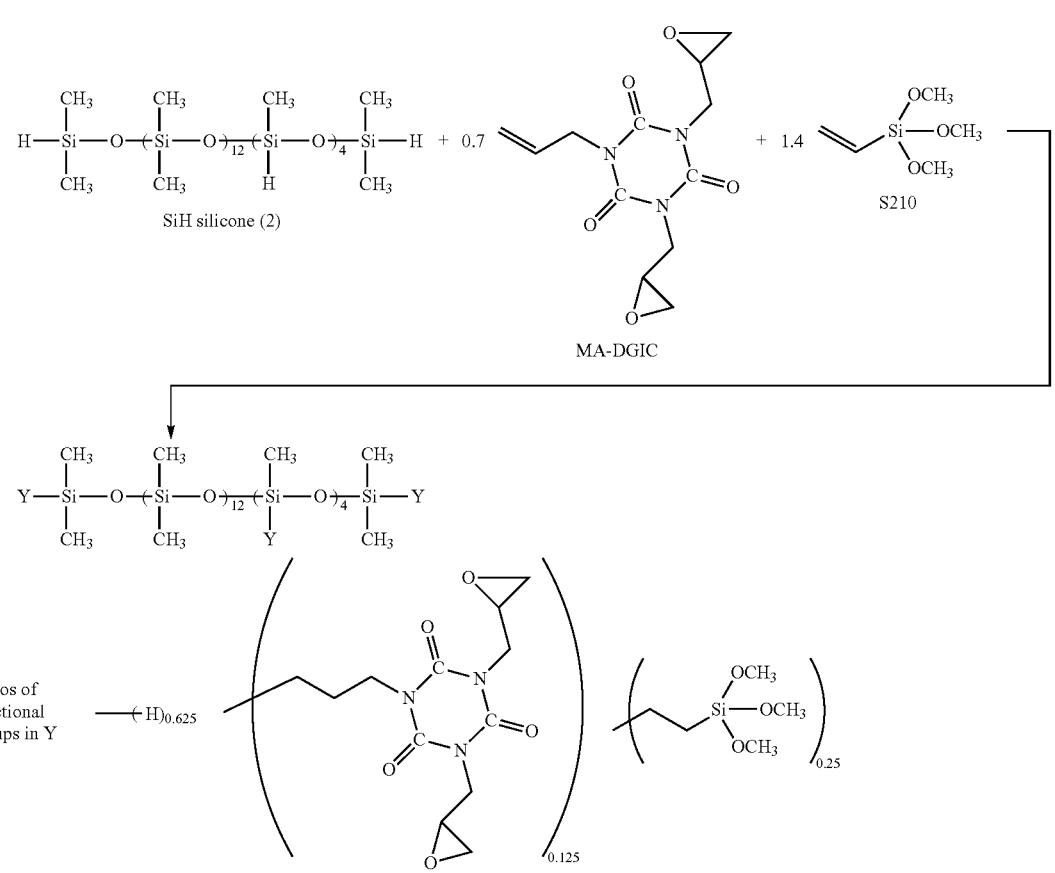

Formula 72

Compound 8 was obtained in a manner identical with the procedures in the synthesis of compound 5 except that 3.5 g of MA-DGIC was used.

Figure 12:
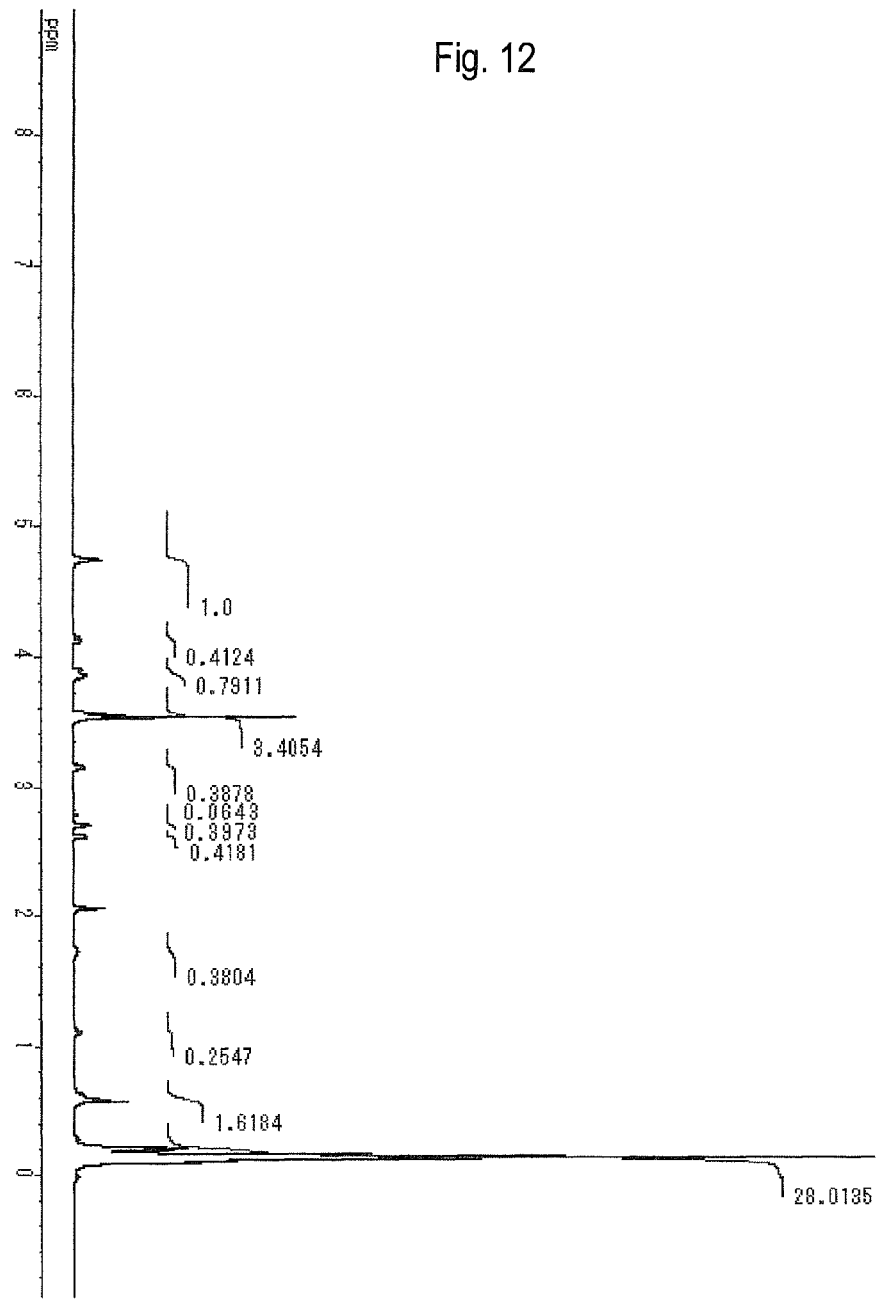
FIG. 12 shows a $^1$H-NMR chart of compound 8 obtained in Example 8.

Molecular weight of the resulting product analyzed by GPC was: number average molecular weight: Mn=2,400, and weight average molecular weight: Mw=4,000. A $^1$H-NMR chart of the product obtained is shown in FIG. 12.

Comparative Synthesis Example 3

Synthesis Comparative Compound 3

According to the reaction formula below, comparative compound 3 having structure below was obtained.

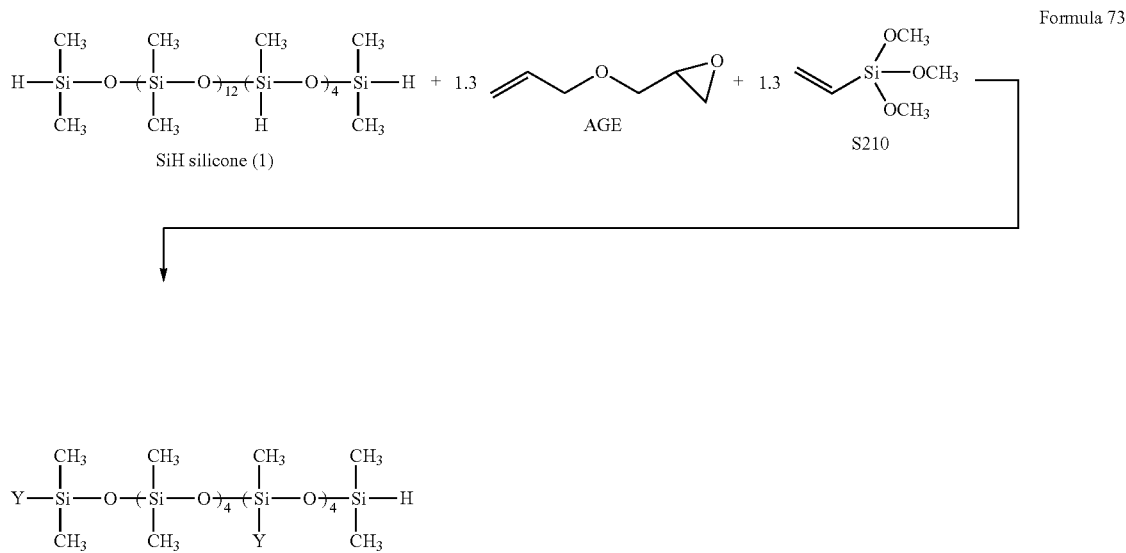

Formula 73

Ratios of functional groups in Y ——(H)₀.₅ 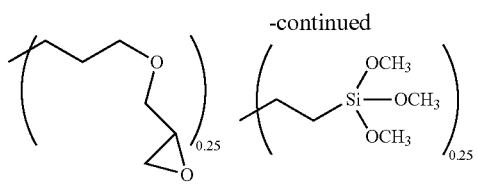

Comparative compound 3 was obtained in a manner identical with the procedures in Example 4 except that MA-DGIC was changed to AGE and 2.7 g thereof was used.

Figure 13:
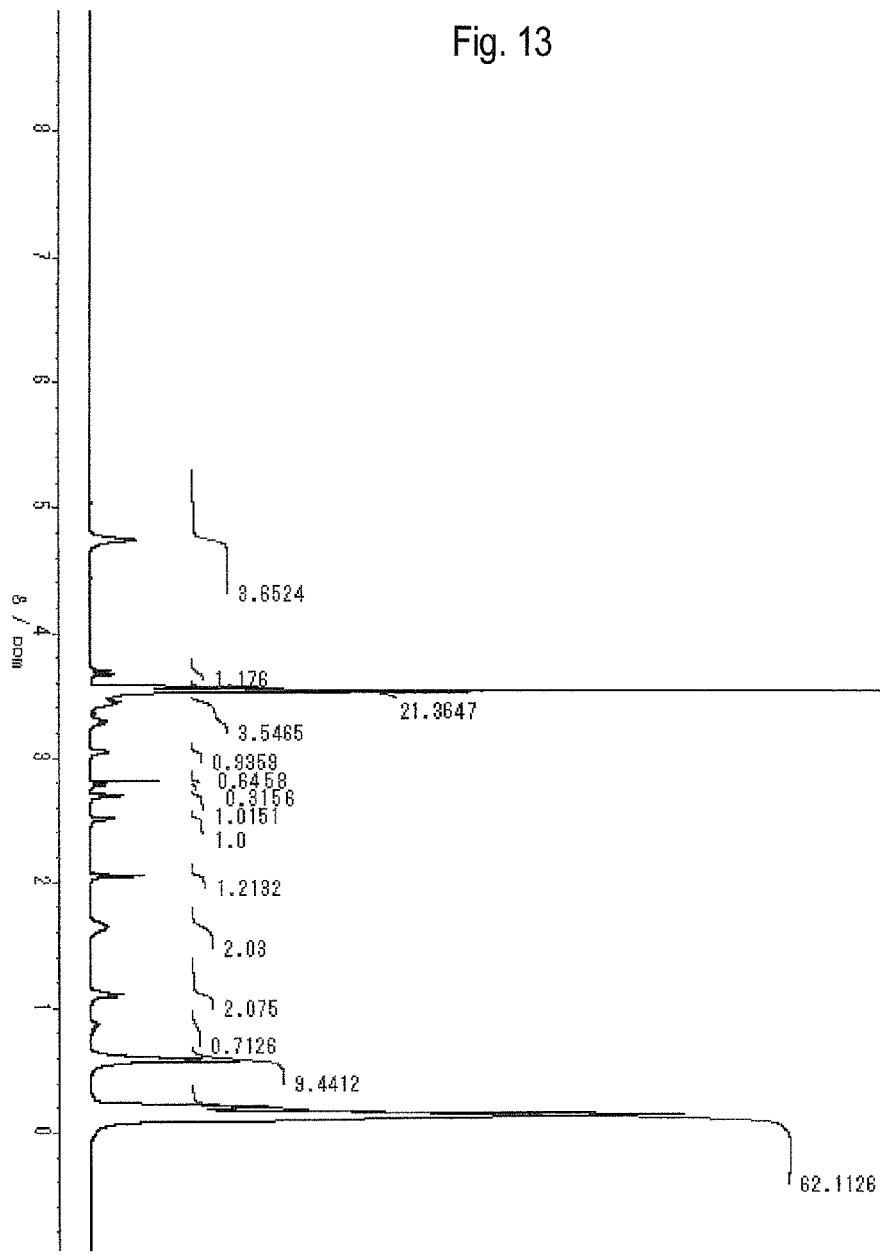
FIG. 13 shows a $^1$H-NMR chart of comparative compound 3 obtained in Comparative Synthesis Example 3.

Molecular weight of the resulting product analyzed by GPC was: number average molecular weight: Mn=1,800, and weight average molecular weight: Mw=2,400. A $^1$H-NMR chart of the product obtained is shown in FIG. 13.

Comparative Synthesis Example 4

Synthesis Comparative Compound 4

According to the reaction formula below, comparative compound 4 having structure below was obtained.

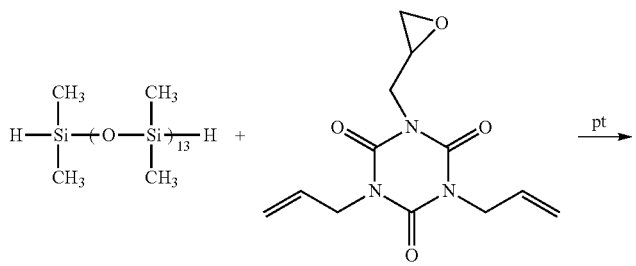

Into a 200 mL (internal volume) reaction vessel equipped with a thermometer, a reflux condenser and a stirrer, 50 g (0.05 mol) of organopolysiloxane having a number average molecular weight of 1,000, an SiH equivalent of 500 g/mol, and having SiH groups at both ends (FM-1111, made by JNC Corporation), 13.9 g (0.0625 mol) of diallylmonoepoxy isocyanurate (DA-MGIC, made by Shikoku Chemicals Corporation), and 50 g of toluene as a solvent were put.

Under a nitrogen atmosphere, heating stirring was started. After the contents reached 100° C., addition of Pt catalyst was made in an amount to be 10 ppm in Pt concentration based on DD-4H, and heating stirring was performed as was for 15 hours. Disappearance of an SiH group was confirmed by IR measurement to terminate the reaction. Toluene was distilled off by an evaporator under reduced pressure conditions of 1 mmHg at 90° C. to give 63 g of pale yellow liquid.

Figure 14:
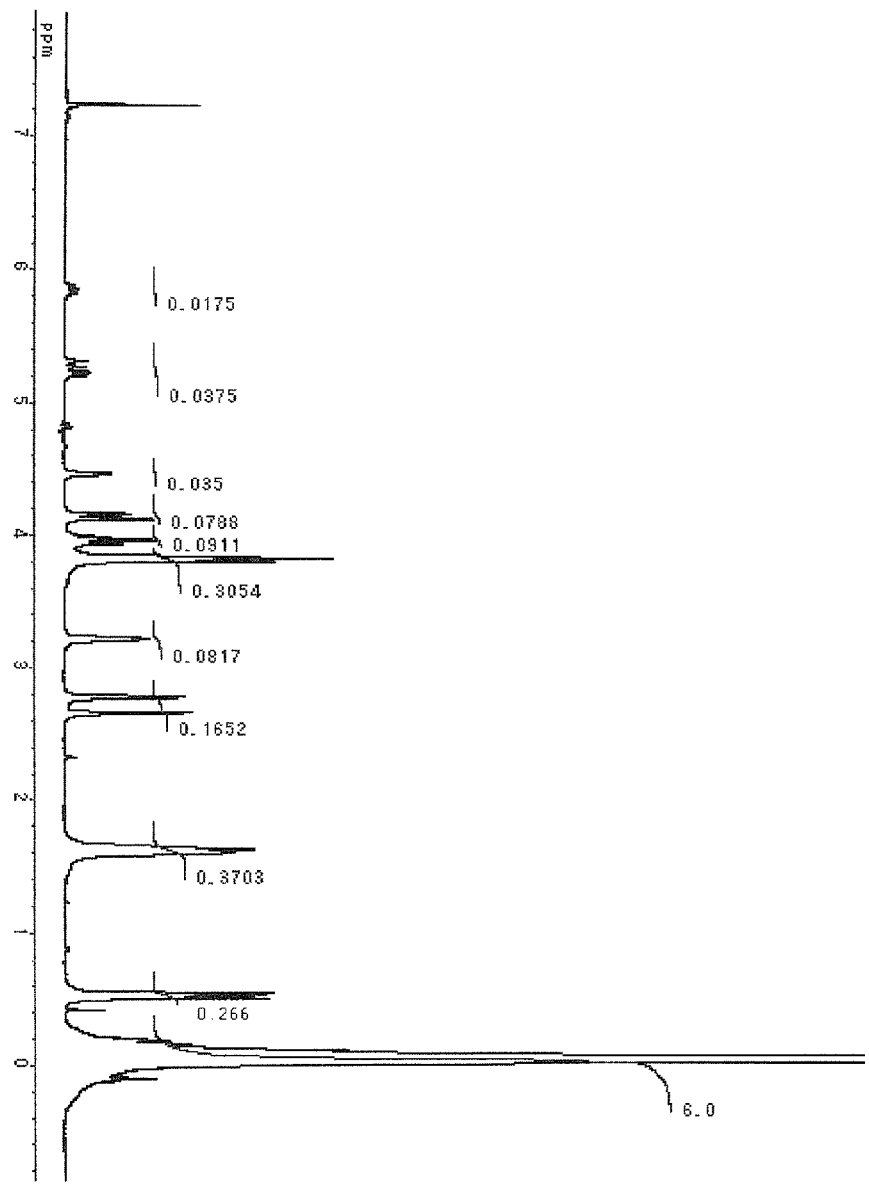
FIG. 14 shows a $^1$H-NMR chart of comparative compound 4 obtained in Comparative Synthesis Example 4.

Molecular weight of the resulting product analyzed by GPC was: number average molecular weight: Mn=7,700 and weight average molecular weight: Mw=17,500. A $^1$H-NMR chart of the product obtained is shown in FIG. 14.

Formula 74

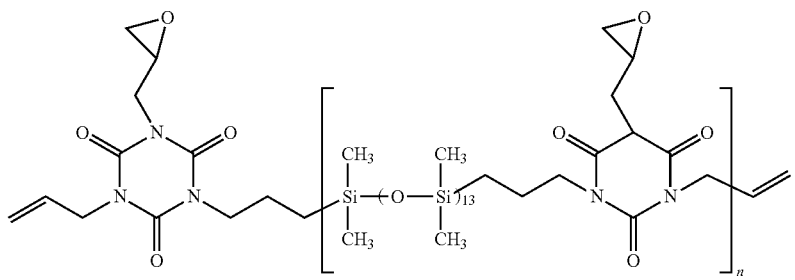

Example 9

Synthesis Compound 9

According to the reaction formula below, compound 9 was synthesized, in which, in the formula (1) above, the number of groups is: A {formula (a)}=2.0, and B {formula (b-i)}=2.0.

Formula 75

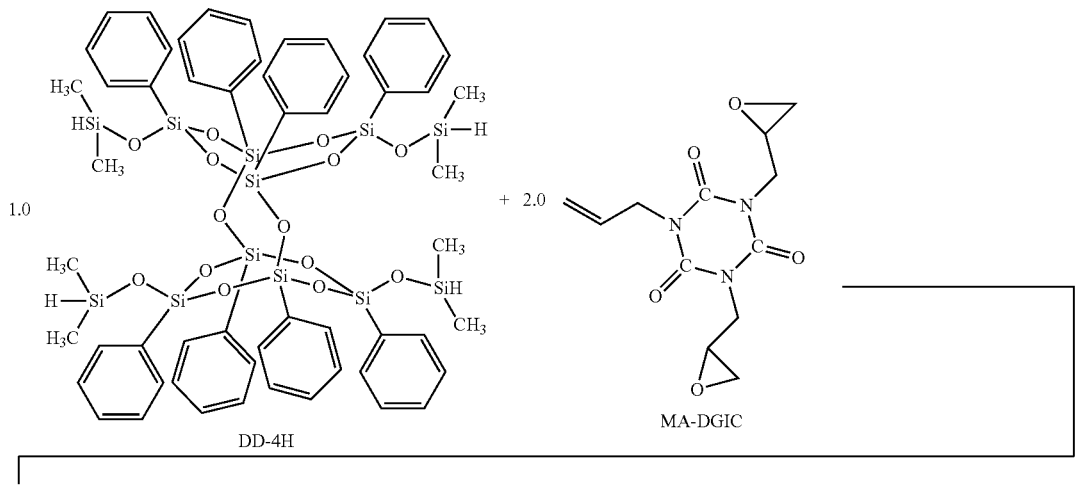

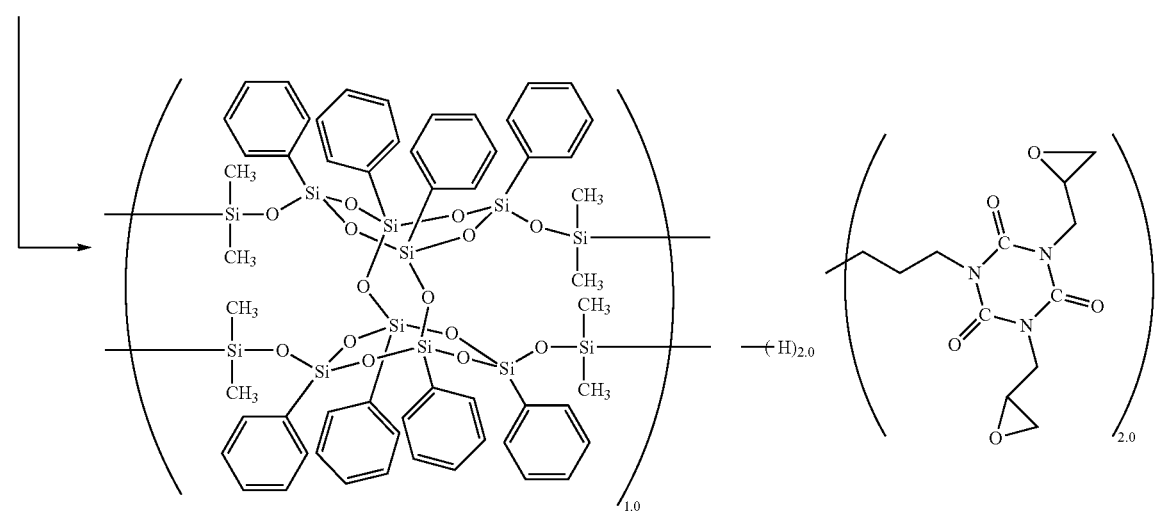

A synthesis was made to give 70 g of colorless transparent solid in a manner identical with the procedures in Example 1 except that change was for DD-4H to 50 g (0.0384 mol), monoallyldiepoxy isocyanurate (MA-DGIC) to 22.8 g (0.0769 mol), and toluene as the solvent to 50 g. In addition, disappearance of MA-DGIC was confirmed by GC herein to terminate the reaction.

Molecular weight of the resulting product analyzed by GPC was: number average molecular weight: Mn=1,180, and weight average molecular weight: Mw=1,240. A $^1$H-NMR chart of the product obtained is shown in FIG. 15.

Figure 15:
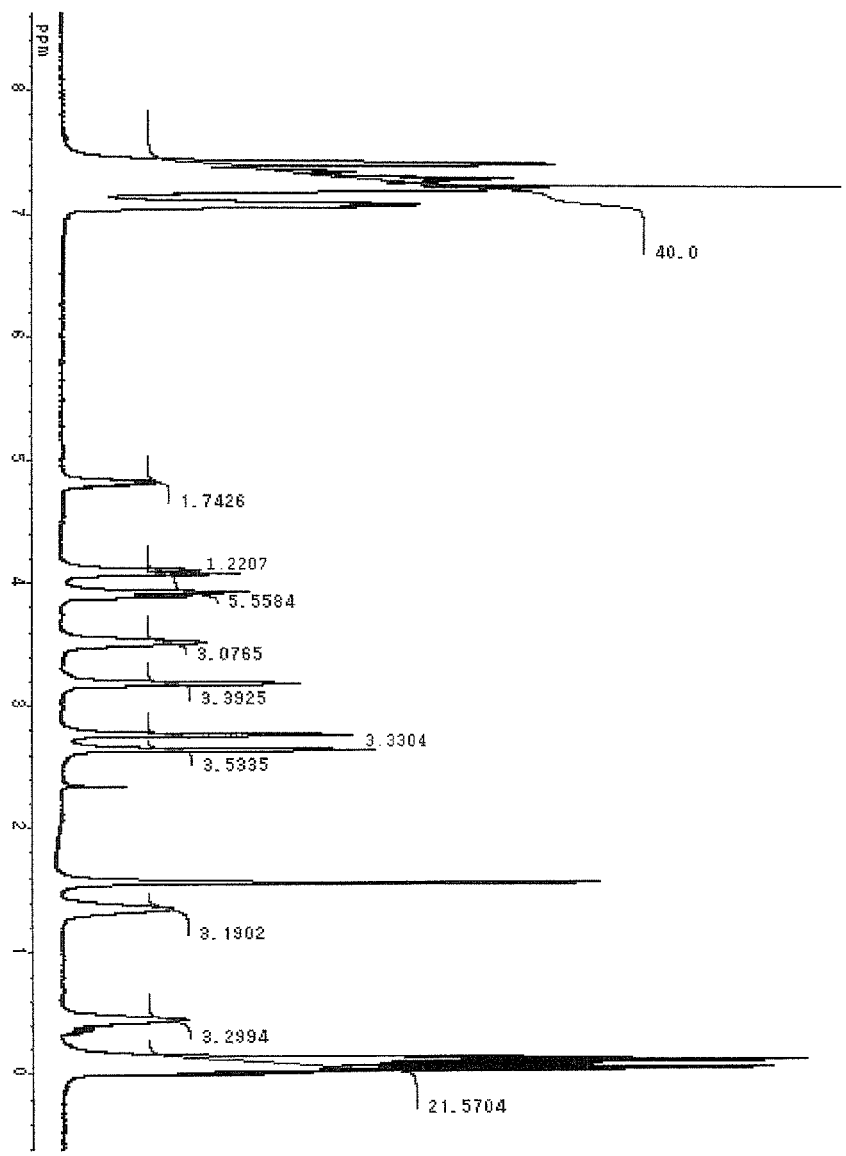
FIG. 15 shows a $^1$H-NMR chart of compound 9 obtained in Example 9.

As shown in FIG. 15, compound 9 was found to have an epoxy group, an isocyanuric ring skeleton and also an SiH group.

Example 10

Synthesis Compound 10

According to the reaction formula below, compound 10 was synthesized, in which, in the formula (1) above, the number of groups is: A {formula (a)}=2.66, B {formula (b-i)}=0.65, 2C {formula (c-i)}~1.38, and D {formula (d)}=0.

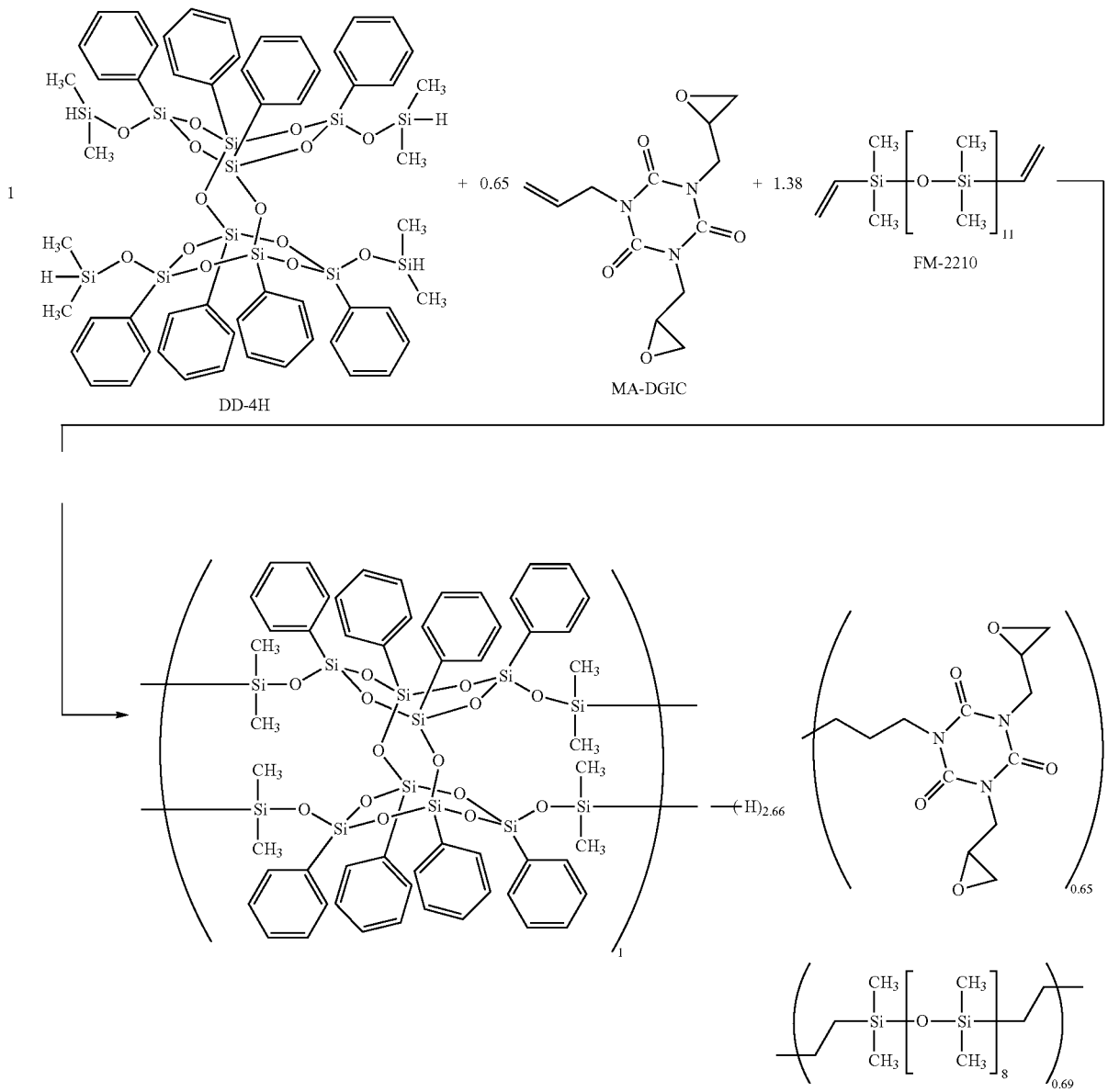

Formula 76

A synthesis was made to give a colorless transparent liquid in a starch syrup state in a manner identical with the procedures in Example 1 except that change was for DD-4H to 50 g (0.0384 mol), vinyl silicone (FM-2210) to 23.8 g (0.0265 mol), monoallyldiepoxy isocyanurate (MA-DGIC) to 7.48 g (0.025 mol), and toluene as the solvent to 50 g.

Molecular weight of the resulting product analyzed by GPC was: number average molecular weight: Mn=3,700, and weight average molecular weight: Mw=14,600. A $^1$H-NMR chart of the product obtained is shown in FIG. 16.

Figure 16:
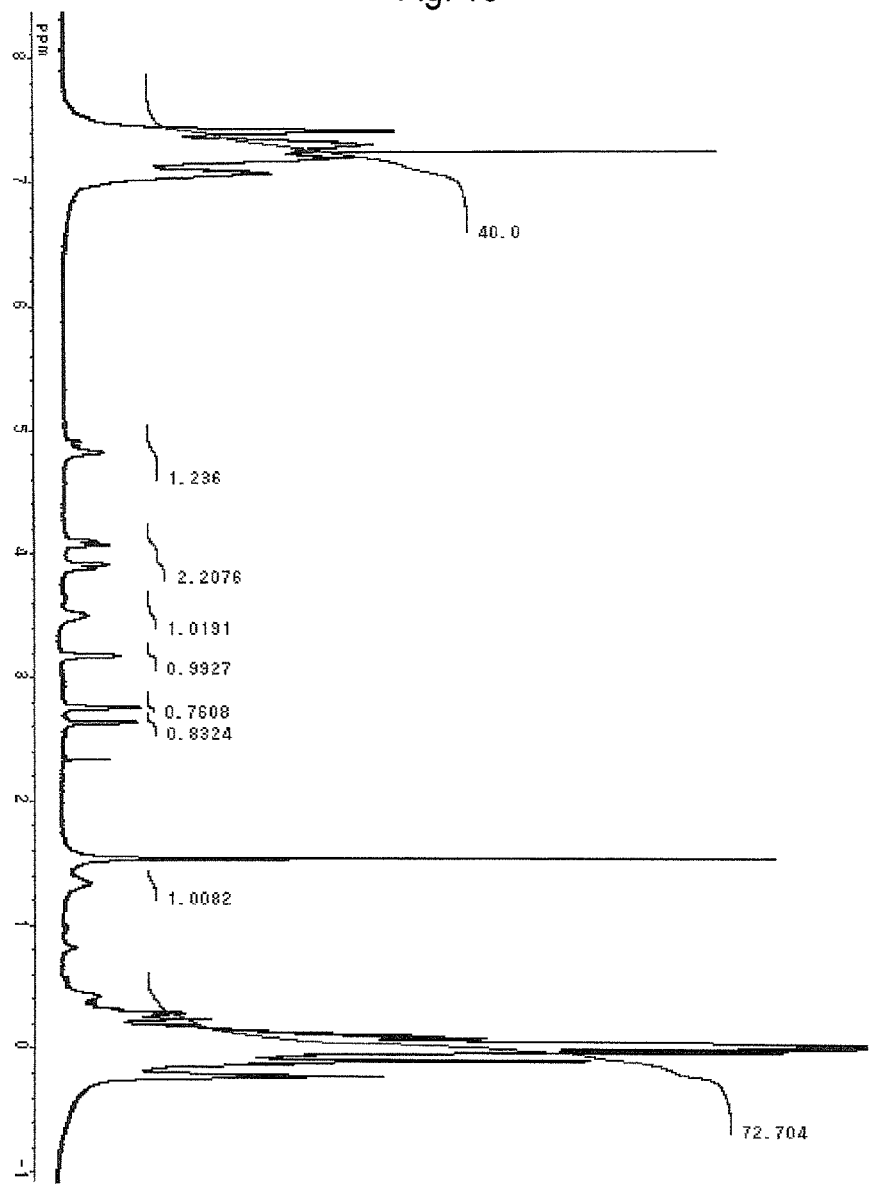
FIG. 16 shows a $^1$H-NMR chart of compound 10 obtained in Example 10.

As shown in FIG. 16, compound 10 was found to have an epoxy group, an isocyanuric ring skeleton, and also an SiH group.

Example 11

Synthesis Compound 11

According to the reaction formula below, compound 11 was synthesized. Into a 300 mL (internal volume) reaction vessel equipped with a thermometer, a reflux condenser and a stirrer, 50 g (0.0384 mol) (0.154 SiH mol) of DD-4H, 7.48 g (0.025 mol) of monoallyldiepoxy isocyanurate (MA-DGIC), and 50 g of toluene as a solvent were put.

Under a nitrogen atmosphere, heating stirring was started. After the contents reached 100° C., addition of Pt catalyst was made in an amount to be 1 ppm in Pt concentration based on DD-4H, and then temperature was increase to 120° C., and heating stirring was performed for 3 hours. Disappearance of MA-DGIC was confirmed by GC to terminate a first-step reaction. The number of moles of remaining SiH was 0.1286 SiH mol at the above time.

Formula 77

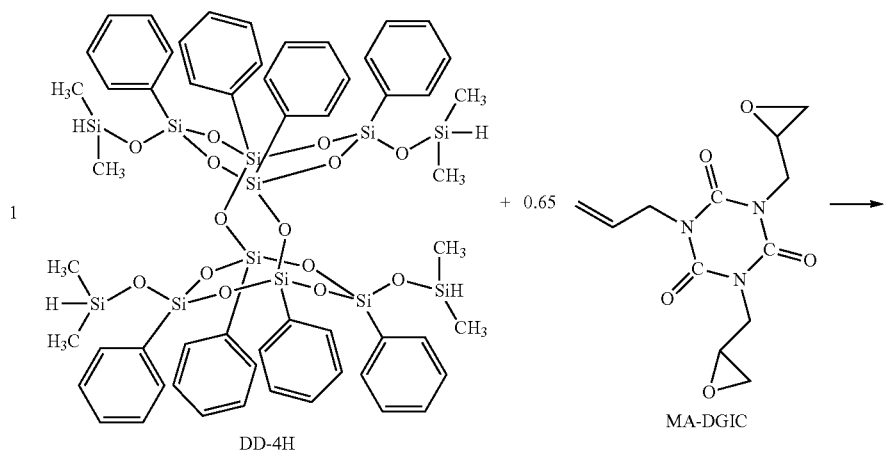

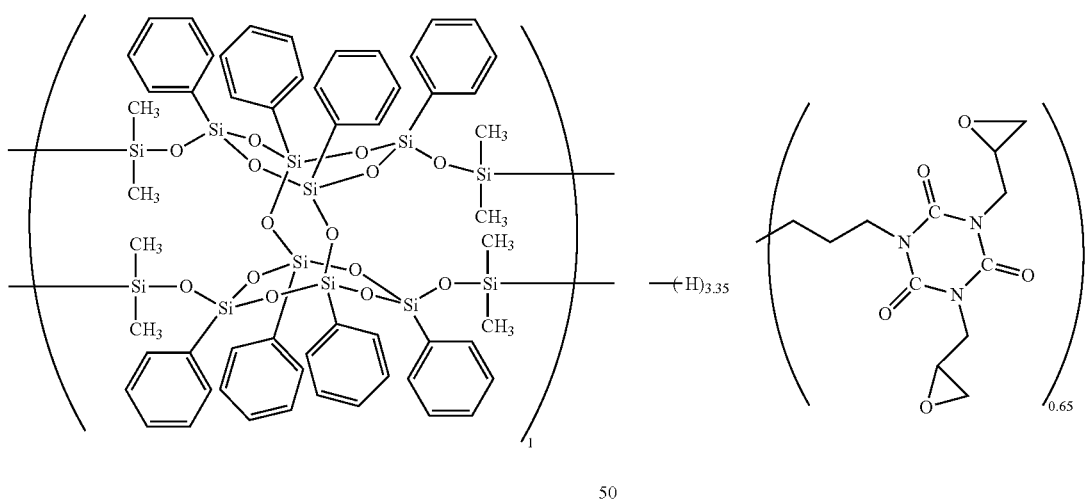

Then, 52.7 g (0.192 mol) (0.192 vinyl mole) of vinyl silicone (Synthesis Example 3) in an excess amount of about 1.5 times based on the number of moles of the SiH group of the compound produced in the first step was charged. Furthermore, a catalyst was added in an amount to be 1 ppm in Pt concentration based on DD-4H to allow a reaction at 120° C. for 2 hours, and then stop the reaction. Cooling was made to room temperature, and then 1.0 g of activated carbon was added, the resulting mixture was stirred for 1 hour or more, and then activated carbon was removed by filtration.

The filtrate was put into an evaporator, and toluene being the solvent, and a part of extra vinyl silicone (Synthesis Example 3) not involved in the reaction were distilled off under reduced pressure conditions of 1 mmHg at 100° C. Furthermore, extra vinyl silicone was removed by performing cutting under reduced pressure conditions of 1 mmHg at 150° C. using an internal condenser type of thin-film evaporator to give 60 g of viscous liquid.

Figure 17:
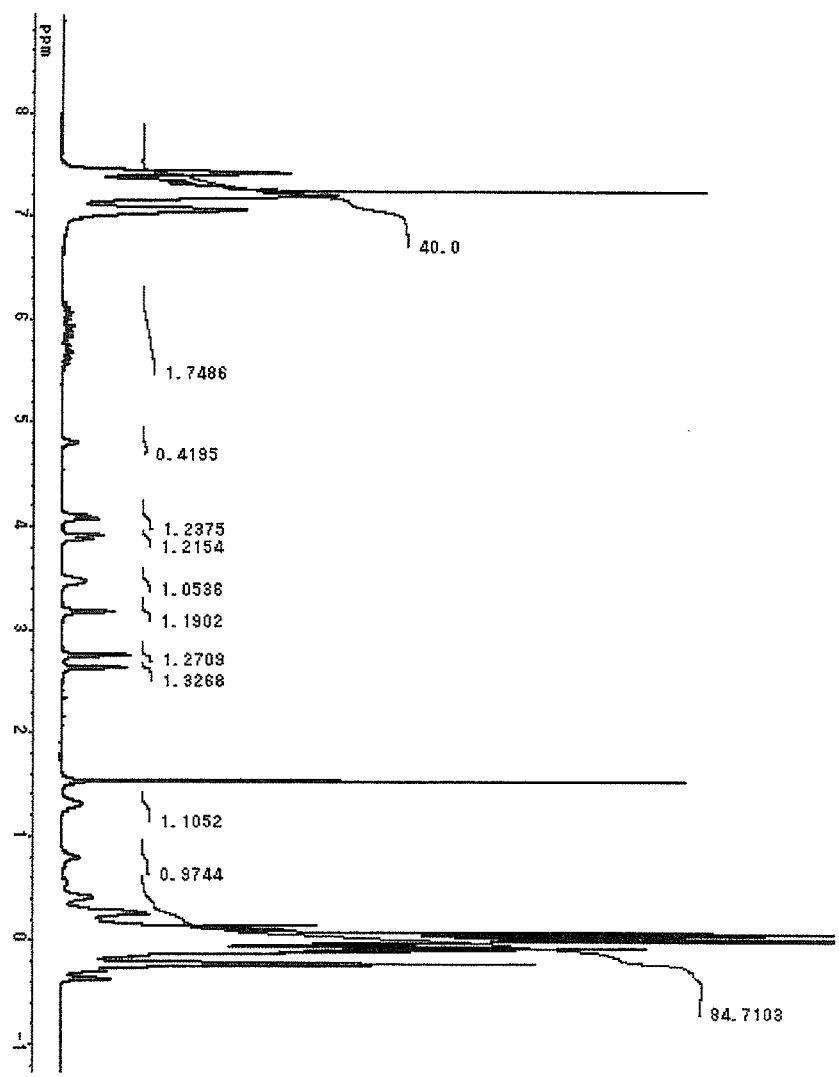
FIG. 17 shows a $^1$H-NMR chart of compound 11 obtained in Example 11.
Figure 18:
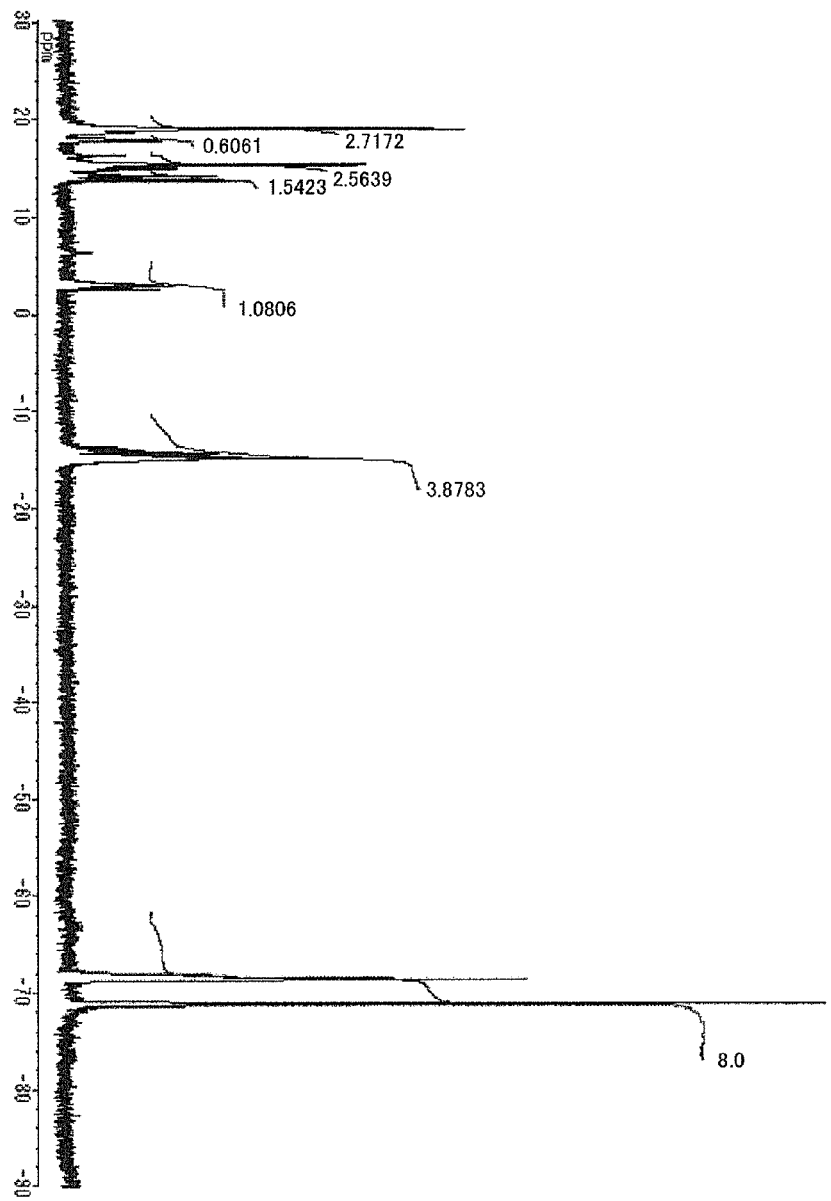
FIG. 18 shows an Si-NMR chart of compound 11 obtained in Example 11.
Figure 19:
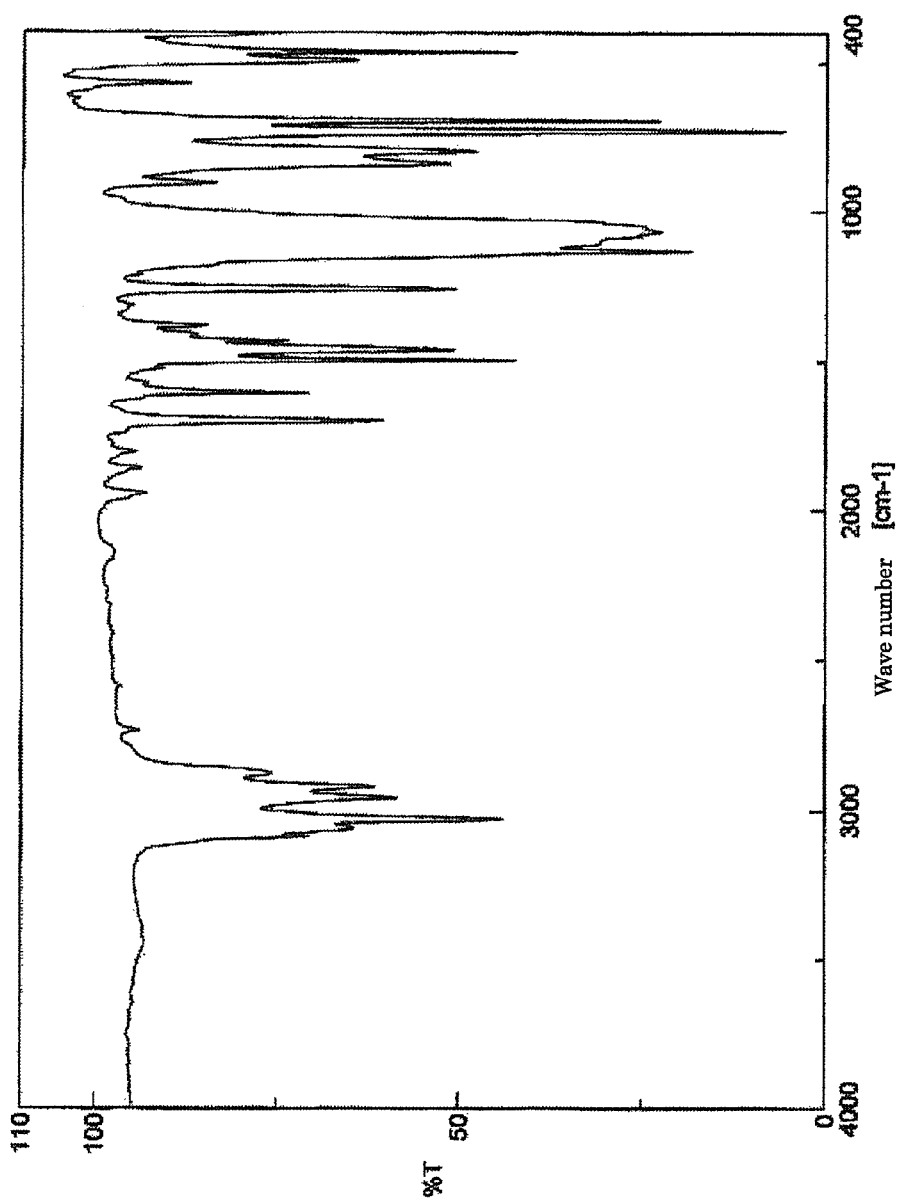
FIG. 19 shows an IR chart of compound 11 obtained in Example 11.

Molecular weight analyzed by GPC was: number average molecular weight: Mn=2,300, and weight average molecular weight: Mw=4,300. A $^1$H-NMR chart of the product obtained is shown in FIG. 17. Moreover, an Si-NMR chart is shown in FIG. 18. An IR chart of the product obtained is shown in FIG. 19. In addition, IR was measured using a liquid diluted two times with a toluene solvent.

As shown in FIGS. 17 and 19, compound 1 was found to have an epoxy group, an isocyanuric ring skeleton and also an SiH group.

When analysis results are synthesized, the reaction formula and the final product are shown as described below.

Formula 78
First-step reaction + excess
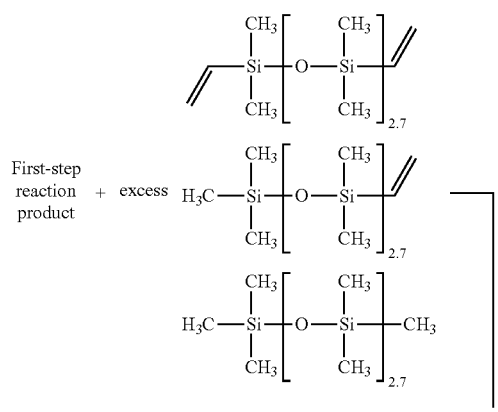
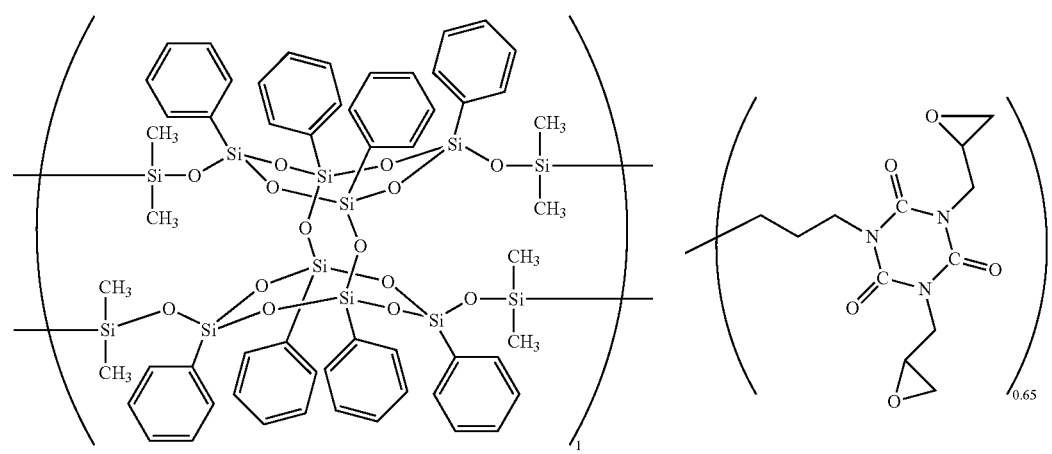
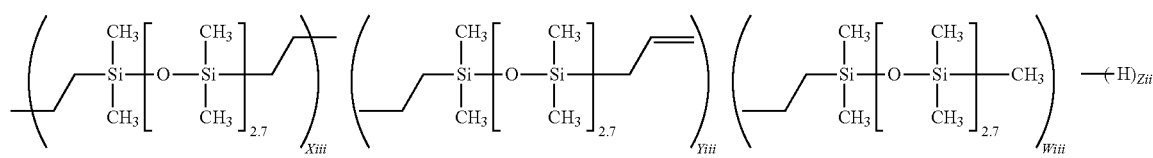
extra
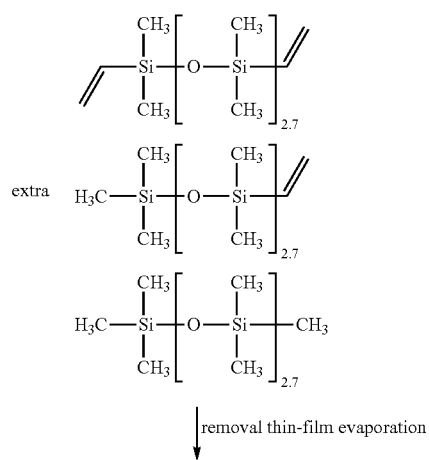
↓ removal thin-film evaporation

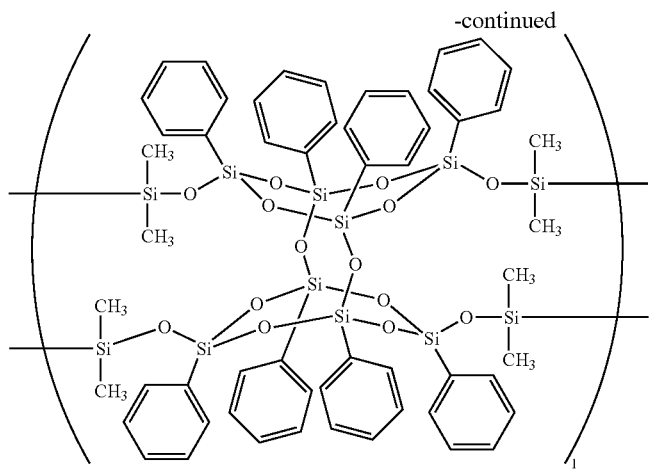
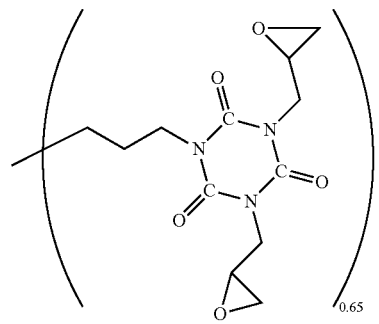

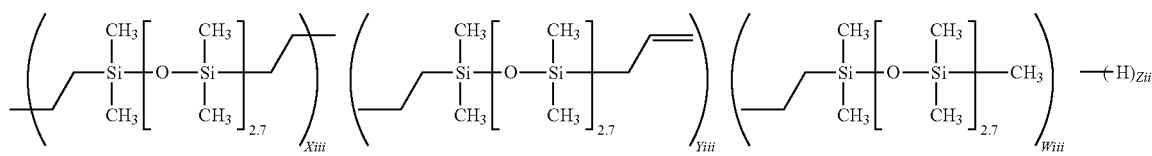

In the reaction formula, Xiii is 0.31, Yiii is 1.08, Wiii is 1.54, and Zii is 0.42. In addition, Xiii, Yiii, Wiii, and Zii were specified as described below.

Zii=integral value of a proton peak of an Si—H group δ (ppm) (4.8).

Yiii=peak integral value of Si of a vinyl group bond δ (ppm) (3.0).

Wiii=peak integral value of Si of a trimethylsilyl group δ (ppm) (14).

Xiii=4−0.65−Xiii−Yiii−Wiii−Zii.

Example 12

Synthesis Compound 12

According to the reaction formula below, compound 12 was synthesized. Into a 300 mL (internal volume) reaction vessel equipped with a thermometer, a reflux condenser and a stirrer, 50 g (0.0384 mol) of DD-4H, 7.48 g (0.025 mol) of monoallyldiepoxy isocyanurate (MA-DGIC), and 50 g of toluene as a solvent were put.

Under a nitrogen atmosphere, heating stirring was started. After the contents reached 100° C., addition of Pt catalyst was made in an amount to be 1 ppm in Pt concentration based on DD-4H, and then temperature was increased to 120° C., and heating stirring was performed for 3 hours. Disappearance of MA-DGIC was confirmed by GC to terminate a first-step reaction.

Formula 79

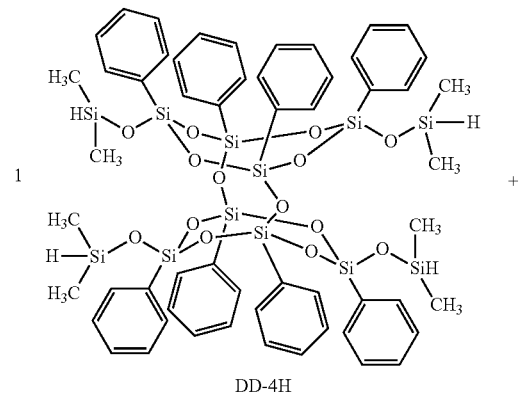

DD-4H

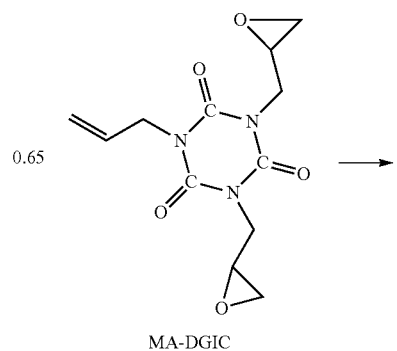

MA-DGIC

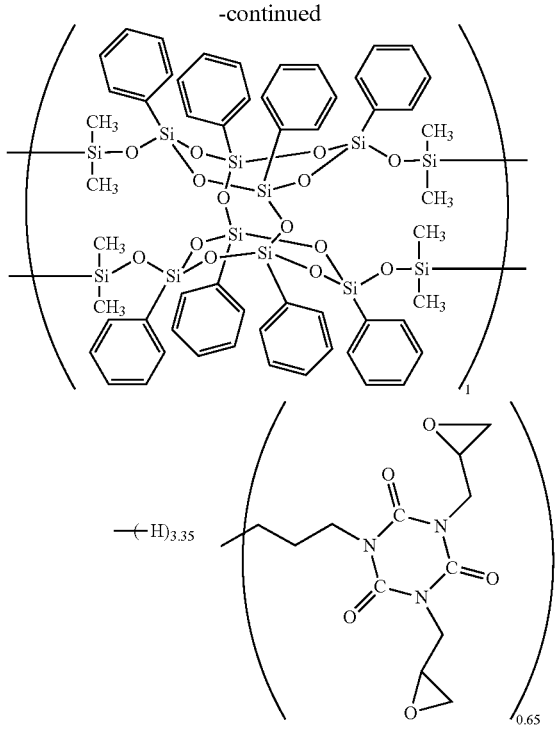

Subsequently, according to a second-step reaction, 68.8 g (0.096 mol) of vinyl silicone (FM-2205) in an excess amount of about 1.5 times based on the number of moles of the SiH group of the compound produced in the first step was added dropwise in 30 minutes and charged. A reaction was allowed at 120° C. for 2 hours, and then stop the reaction. Cooling was made to room temperature, and then 1.0 g of activated carbon was added, the resulting mixture was stirred for 1 hour or more, and then activated carbon was removed by filtration.

The filtrate was put into an evaporator, and toluene being the solvent was distilled off under reduced pressure conditions of 1 mmHg at 100° C. to give 105 g of viscous liquid.

Figure 20:
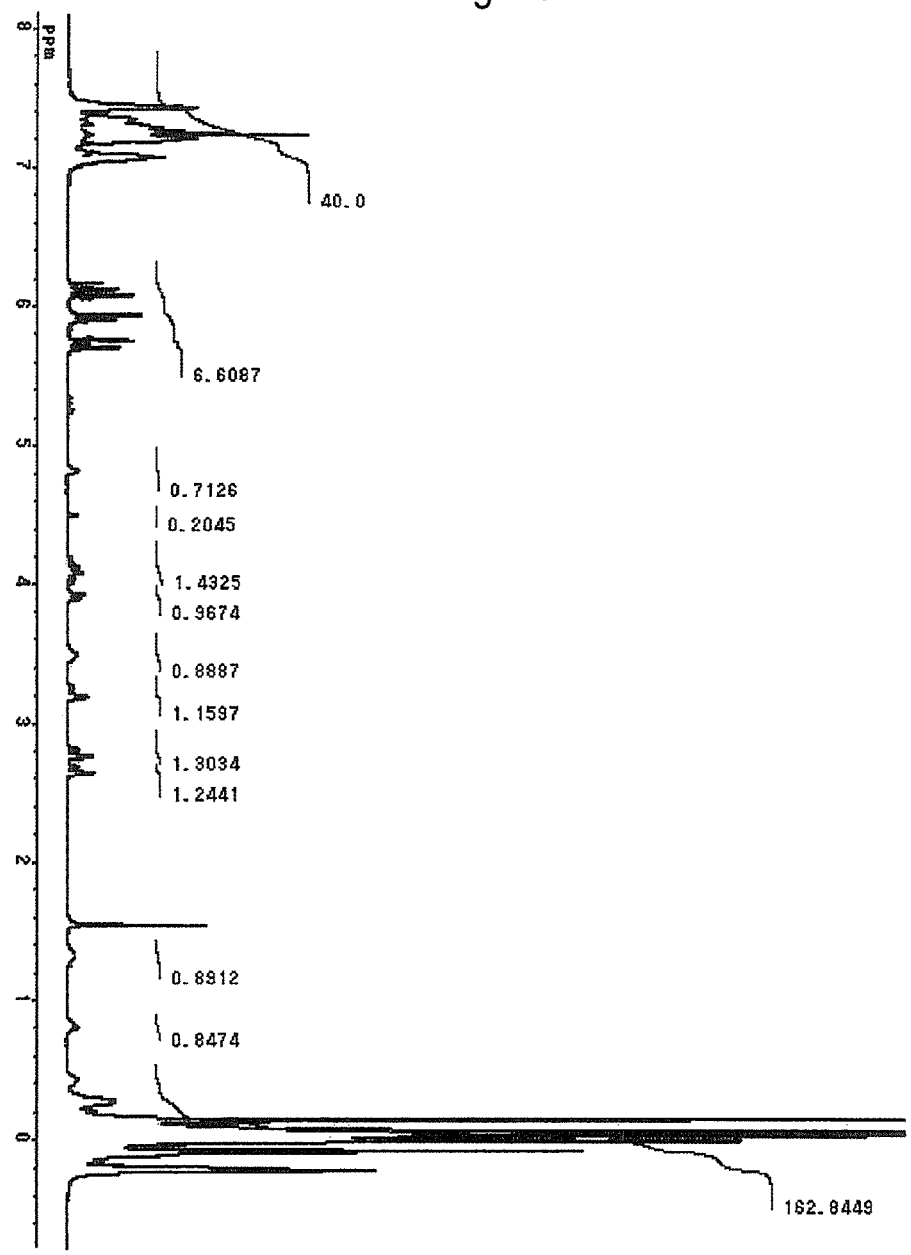
FIG. 20 shows a $^1$H-NMR chart of compound 12 obtained in Example 12.
Figure 21:
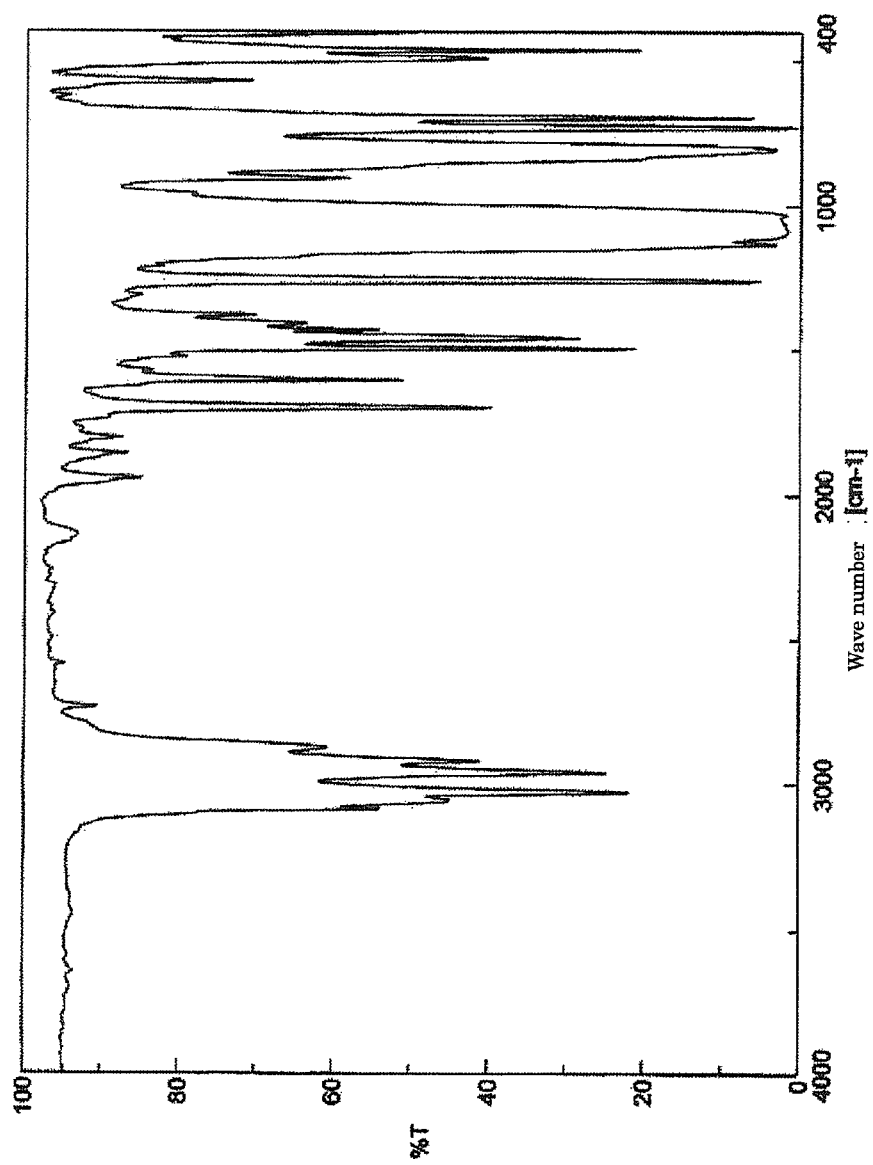
FIG. 21 shows an IR chart of compound 12 obtained in Example 12.

Molecular weight analyzed by GPC was: number average molecular weight: Mn=6,100, and weight average molecular weight: Mw=11,500. A $^1$H-NMR chart of the product obtained is shown in FIG. 20. Moreover, an IR chart of the product obtained is shown in FIG. 21. In addition, IR was measured using a liquid diluted tow times with a toluene solvent.

Quantitative Determination of Unreacted Remaining FM-2205

GC of a mixture of toluene and FM-2205 at weight ratios of 1:1, 2:1 and 4:1 was measured, and a calibration curve of FM-2205 was prepared. A correction coefficient was calculated to be 18.6. Subsequently, when the product and toluene were mixed at a weight ratio of 1:1, and then GC was measured to quantitatively determine remaining FM-2205, the remaining FM-2205 was 12.3% by mass.

As shown in FIG. 20, compound 1 was found to have an epoxy group, an isocyanuric ring skeleton and also an SiH group.

When analysis results are synthesized, the reaction formula and the final product are shown as described below.

Formula 80

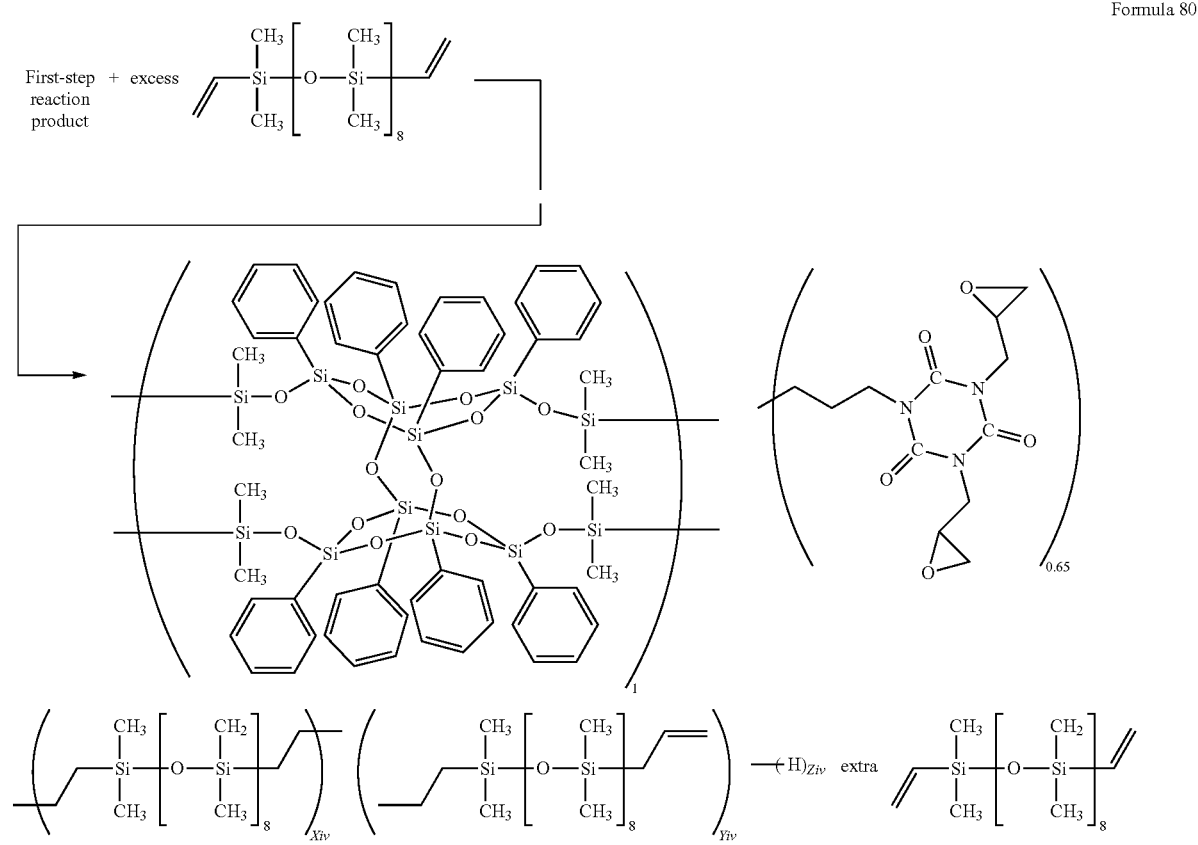

In the reaction formula, Xiv is 0.76, Yiv is 1.96, and Ziv is 0.63. In addition, values of Xiv, Yiv and Ziv described above were specified below.

$$Ziv = \text{integrated intensity of proton peak of an SiH group} \times (100-12.3)/100.$$

$$Yiv = \text{integrated intensity of proton peak of a vinyl group} \times \frac{1}{3} \times (100-12.3)/100.$$

$$Xiv = 4 - 0.65 - Ziv - Yiv.$$

In addition, 12.3 in the calculation formula of Ziv and Yiv refers to % by mass of unreacted remaining vinyl silicone (FM-2205) described above.

Preparation of Thermosetting Resin Composition

A mixture of the compound synthesized in the Example, and DVTS or organopolysiloxane synthesized in the Synthesis Example were put into a screw vial. The screw vial was set to Planetary Centrifugal Mixer (Thinky Mixer (registered trademark) ARE-250, made by Thinky Corporation), and mixing and defoaming were performed.

A hardening retarder: MVS-H (trade name, 1,3,5,7-tetravinyl-1,3,5,7-tetramethylcyclotetrasiloxane: made by JNC Corporation) was added to be 10 ppm in the concentration and a platinum catalyst to be 1 ppm in the concentration, and mixing and defoaming were performed again by Planetary Centrifugal Mixer, and thus compositions a to j and comparative compositions a to i being thermosetting resin compositions were obtained. An amount of compounding (g) of each thermosetting resin composition is shown in Tables 1, 3 and 5.

Preparation of a Hardened Material

With regard to the thermosetting resin composition, Naflon SP packing (diameter of 4 mm) made by NICHIAS Corporation was interposed as a spacer between two sheets of glass, a thermosetting resin composition was poured thereinto and defoamed under reduced pressure, heated at 80° C. for 1 hour, and then at 150° C. for 4 hours, thereby hardening the composition, and the glass was pealed to give 4-mm thick hardened materials a to j and comparative hardened materials a to i having smooth surfaces were obtained.

Physical properties of hardened materials a to j and comparative hardened materials a to i were evaluated by the methods described below. Results thereof are presented in Tables 2, 4 and 6.

Measurement of Transmittance

A transmittance at 400 nanometers was measured by a UV-Vis spectrophotometer UV-1650 made by Shimadzu Corporation.

Refractive Index

A hardened material is cut with a band saw, and a test specimen prepared according to JIS K7142 (2008). The test specimen was used, and a refractive index was measured using a D line (586 nm) of a sodium vapor lamp by an Abbe refractometer (NAR-2T made by ATAGO Co., Ltd.). As an intermediate liquid methylene iodide was used.

Hardness

Measurement was carried out by Durometer WR-105D made by Nishitokyo Seimitsu Co., Ltd. according to JIS K6253 (1997).

Heat Resistance Test

A heat resistance test was conducted according to the method described below and evaluated. Two pieces of 4 mm-thick hardened materials were prepared, each luminous transmittance was measured by a UV-Vis spectrophotometer, and a measured value was taken as an initial transmittance. A hardened material was put into an oven at 180° C. (constant-temperature dryer: DX302 made by Yamato Scientific Co., Ltd.) and subjected to heat treatment for a fixed period of time (1,000 hours in Tables 2, 4 and 6).

Resistance to Thermal Yellowing

Luminous transmittance of a hardened material after the heat resistance test was measured by a UV-Vis spectrophotometer, and from transmittance at a wavelength of 400 nanometers, a retention ratio at the wavelength transmittance after heat treatment for a fixed period of time/initial transmittance (at each wavelength)×100) was calculated and evaluated. A retention ratio of transmittance at 400 nanometers after 1,000 hours of heat resistance test at 180° C. is preferably 85% or more.

Adhesion Strength Test: Polyphthalamide Resin

A test was conducted according to JIS K6850 (1999). A thermosetting resin composition was interposed between base materials prepared by adjusting a dimension of the base material (PA9T (trade name) Genestar TA112 made by Kuraray Co., Ltd.) according to JIS K6850 (1999), and subjected heating hardening at 80° C. for 1 hour and then at 150° C. for 1 hour, and thus a test specimen was prepared. As an adhesion test, strength was measured using a load cell of 5 kN by a tensile compression tester (Autograph AGS-500B made by Shimadzu Corporation). In addition, "substrate break" in Tables presents that adhesion between a hardened material and a substrate is significantly strong, and substrate strength cannot withstand the adhesion test, and resulted in break of the substrate.

Adhesion Strength Test: Ag

A test was conducted according to JIS K6850 (1999). A thermosetting resin composition was interposed between base materials being silver-plated standard test substrates (made by Nihon Testpanel Co., Ltd.), and subjected heating hardening at 80° C. for 1 hour and then at 150° C. for 4 hours, and thus a test specimen was prepared. As an adhesion test, strength was measured using a load cell of 5 kN by a tensile compression tester (Autograph AGS-5003 made by Shimadzu Corporation).

Adhesion Strength Test: LCP

A test was conducted according to JIS K6850 (1999). A thermosetting resin composition was interposed between base materials prepared by adjusting a dimension of the base material, liquid crystal polymer (LCP) trade name: Sumica Super LCP E4008, according to JIS K6850 (1999), and subjected heating hardening at 80° C. for 1 hour and then at 150° C. for 4 hours, and thus a test specimen was prepared. As an adhesion test, strength was measured using a load cell of 5 kN by a tensile compression tester (Autograph AGS-500B made by Shimadzu Corporation).

Reflow Heat Cycle Test

Into 15 pieces of premolded packages for power LED, each package having a thickness of 1.5 mm, one side of 5 mm, an opening diameter of 3.5 mm, and silver-plated bottom, a thermosetting resin composition was poured by a dispenser, and the composition was subjected to heating hardening. In accordance with JEDEC standards, the resulting material was, through an IR reflow furnace under temperature conditions (260° C.), put into a test area of cold impact tester TSE-11 made by ESPEC Corporation, and subjected to testing by repeating 100 cycles by taking as one cycle exposure at −40° C. for 30 minutes, and at 150° C. for 30 minutes. In addition, the test conducted by adjusting transfer time to be 2 minutes between both exposure temperatures. Generation of peeling and a crack was observed by a microscope. A fraction defective in 15 pieces is presented.

TABLE 1

|  | Composition |  |  |  | Compounding amount (g) Comparative composition |  |  |  |
|---|---|---|---|---|---|---|---|---|
|  | a | b | c | d | a | b | c | d |
| Silsesquioxane base polymer 1 | 10 | 10 | 10 | 10 | 10 | 10 | 10 | 10 |
| Vinyl silicone (FM-2205) | 1.8 | 1.8 | 1.8 | 1.8 | 1.8 | 1.8 | 1.8 | 1.8 |
| Compound 1 | 0.59 | | | | | | | |
| Compound 2 | | 0.48 | | | | | | |
| Compound 3 | | | 0.295 | | | | | |
| Compound 4 | | | | 0.295 | | | | |
| S510 | 0.03 | | | | 0.03 | | | |
| MA-DGIC | | | | | | 0.06 | | |
| Comparative compound 1 | | | | | | | 0.59 | |
| Comparative compound 2 | | | | | | | | 0.295 |

TABLE 2

|  | Hardened material |  |  |  | Comparative hardened material |  |  |  |
|---|---|---|---|---|---|---|---|---|
|  | a | b | c | d | a | b | c | d |
| Refractive index | 1.50 | 1.50 | 1.50 | 1.50 | 1.50 | 1.50 | 1.50 | 1.50 |
| D hardness | 26 | 30 | 26 | 28 | 32 | 34 | 30 | 31 |
| Resistance to thermal yellowing (Retention ratio % at 400 nm) | 92 | 91 | 91 | 92 | 93 | 87 | 87 | 90 |
| Adhesion strength test PA9T (MPa) | 2.7 | Substrate break | 1.7 | 1.7 | 0.7 | 1.2 | 1.9 | 0.2 |
| Adhesion strength test LCP (MPa) | 2.5 | 2.9 | 1.5 | 2.0 | 1.2 | 2.6 | 1.2 | 0.9 |
| Adhesion strength test Ag (MPa) | 1.5 | 2.7 | 1.5 | 1.3 | 1.3 | 1.5 | 1.1 | 1.3 |
| Heat cycle test (Fraction defective) | 20 | 0 | 50 | 80 | 40 | 90 | 100 | 100 |

Table 2 presents that all of hardened materials a to d prepared using compounds 1 to 4 according to the invention as the adhesion-imparting agent were found to be superior in resistance to thermal yellowing, adhesion properties with polyphthalamide resin (PA9T) or Ag, and a heat cycle resistance.

In contrast, comparative hardened materials a and b containing comparative compound 1 or 2 were poor in adhesion force with polyphthalamide resin, and heat cycle resistance. Moreover, comparative hardened material c has an epoxy group, but containing comparative compound 1 with no isocyanuric ring skeleton, and therefore was found to be a hardened material having weak adhesion with silver.

TABLE 3

|  | Composition |  |  |  | Compounding amount (g) Comparative composition |  |
|---|---|---|---|---|---|---|
|  | e | f | g | h | e | f |
| Silsesquioxane base polymer 1 | 10 | 10 | 10 | 10 | 10 | 10 |
| Vinyl silicone (FM-2205) | 1.8 | 1.8 | 1.8 | 1.8 | 1.8 | 1.8 |
| Compound 5 | 0.057 | | | | | |
| Compound 6 | | 0.055 | | | | |
| Compound 7 | | | 0.16 | | | |
| Compound 8 | | | | 0.24 | | |
| Comparative compound 3 | | | | | 0.059 | |
| Comparative compound 4 | | | | | | 0.66 |

TABLE 4

|  | Hardened material |  |  |  | Comparative composition |  |
|---|---|---|---|---|---|---|
|  | e | f | g | h | e | f |
| Refractive index | 1.5 | 1.5 | 1.5 | 1.5 | 1.5 | 1.5 |
| D hardness | 30 | 30 | 30 | 30 | 30 | 30 |
| Resistance to thermal | 88 | 88 | — | — | 88 | No test due to |

TABLE 4-continued

|  | Hardened material | | | | Comparative composition | |
| --- | --- | --- | --- | --- | --- | --- |
|  | e | f | g | h | e | f |
| yellowing (Retention ratio % at 400 nm) |  |  |  |  |  | white turbidity |
| Adhesion strength test PA9T (MPa) | Substrate break | Substrate break | 3.1 | 2.8 | 0.7 | No test due to white turbidity |
| Adhesion strength test LCP (MPa) | 3.1 | 2.9 | 2.8 | 2.8 | 1.4 | 0.6 |
| Adhesion strength test Ag (MPa) | 2.6 | 1.8 | 1.5 | 1.1 | 0.7 | 0.7 |
| Heat cycle test (Fraction defective) | 20 | 10 | 10 | 60 | 100 | No test due to white turbidity |

Table 4 presents that all of hardened materials e to h prepared using compounds 5 to 8 according to the invention as the adhesion-imparting agent were found to be superior in resistance to thermal yellowing, adhesion properties with polyphthalamide resin (PA9T) or Ag, and heat cycle resistance.

In contrast, comparative hardened material e containing comparative compound 3 having the epoxy group in a side chain but including no isocyanuric ring skeleton were poor in adhesion force with polyphthalamide resin, and heat cycle resistance. Moreover, comparative hardened material f using comparative compound 4 became white turbid, and measurement of the refractive index was not allowed, and has low adhesion strength.

TABLE 5

|  | Composition | | Comparative composition | | |
| --- | --- | --- | --- | --- | --- |
|  | h | i | g | h | i |
| Silsesquioxane base polymer 2 | 10 | 10 | 10 | 10 | 10 |
| Vinyl silicone (FM-2205) | 1.1 | 1.1 | 1 | 1.1 | 1.1 |
| Compound 1 | 0.11 |  |  |  |  |
| Compound 2 |  | 0.28 |  |  |  |
| S510 | 0.03 |  | 0.03 | 0.03 | 0.03 |
| MA-DGIC |  |  |  | 0.56 | 1.12 |

TABLE 6

|  | Hardened material | | Comparative hardened material | | |
| --- | --- | --- | --- | --- | --- |
|  | h | i | g | h | i |
| Refractive index | 1.51 | 1.51 | 1.51 | 1.51 | 1.51 |
| D hardness | 65 | 65 | 65 | 65 | 65 |
| Resistance to thermal yellowing (Retention ratio % at 400 nm) | 86% | 90 | 91 | 87 | 69 |
| Adhesion strength test PA9T (MPa) | Substrate break | Substrate break | 2.2 | 3.3 | 3.3 |
| Adhesion strength test LCP (MPa) | 5.9 | 7.4 | 3.7 | 4.9 | 5 |

TABLE 6-continued

|  | Hardened material | | Comparative hardened material | | |
| --- | --- | --- | --- | --- | --- |
|  | h | i | g | h | i |
| Adhesion strength test Ag (MPa) | 6.1 | 5.9 | 3.6 | 4.8 | 5.4 |
| Heat cycle test (Defective ratio) | 0 | 50 | 100 | 100 | 60 |

Table 6 presents that all of hardened materials h to i prepared using compound 1 to 2 according to the invention as the adhesion-imparting agent were found to be superior in resistance to thermal yellowing, adhesion properties with polyphthalamide resin (PA9T), Ag or liquid crystal polymer (LCP), and heat cycle resistance.

In contrast, comparative hardened material g using a commercially available silane coupling agent was found to be weak in heat cycle resistance. Moreover, comparative hardened materials h and i using commercially available monoallyldiepoxy isocyanurate was found to have relatively improved adhesion strength, but to be low in a heat-resistant retention ratio and heat cycle resistance.

Although the invention has been described in detail using a specific embodiment, it is clear that numerous changes and modifications can be resorted to by those skilled in the art without departing from the spirit and scope of the invention. In addition, the present application is based on Japanese patent application (application for patent 2011-148476) filed on Jul. 4, 2011, and entirely is incorporated by reference.

The invention claimed is:

1. A compound obtained by allowing a hydrosilylation addition reaction of (A) and (B), and when necessary (C) as described below, the compound comprising a silsesquioxane skeleton including as an essential component an isocyanuric ring skeleton and an epoxy group, and having an SiH-group residue:

(A) a compound including a silsesquioxane skeleton, and having three or more SiH groups in one molecule;

(B) an epoxy derivative having one aliphatic unsaturated group in one molecule; and (C) organopolysiloxane having two alkenyl groups in one molecule and having a number average molecular weight of 100 to 500,000, or an isocyanurate compound having two alkenyl groups in one molecule;

wherein the compound comprising the silsesquioxane skeleton including as the essential component the isocyanuric ring skeleton and the epoxy group, and having the SiH group residue is a compound represented by general formula (1):

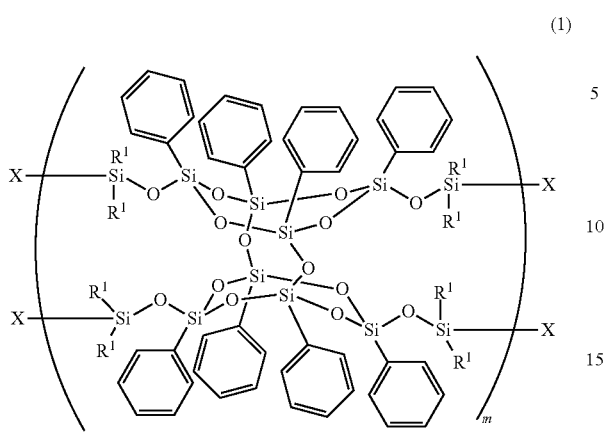
(1)

wherein, in formula (1), X is each independently a group represented by formula (a), formula (b-i), formula (b-ii), formula (b-iii), formula (c-i), formula (c-ii), formula (c-iii) or formula (d) below, and with regard to the number of groups per one molecule of compound represented by formula (1) (per one molecule on average of the compound when the compound is a mixture in which a ratio of the group represented by formula (a), a ratio of the group represented by formula (b-i) and a ratio of the group represented by formula (b-ii) and formula (b-iii) are different), in the case where the number of groups represented by formula (a) is taken as A, the number of groups represented by formula (b-i), formula (b-ii) or formula (b-iii) is taken as B, the number of groups represented by formula (c-i), formula (c-ii) or formula (c-iii) is taken as C, and the number of groups represented by formula (d-i), formula (d-ii) or formula (d-iii) is taken as D, expressions: $A+B+2C+D=4$, $0.1 \leq A \leq 3.5$, $0.1 \leq B \leq 3.5$, $0 \leq 2C \leq 2.0$, and $0 \leq D \leq 3.0$ hold; and $R^1$ is each independently a group selected from alkyl having 1 to 4 carbons, cyclopentyl and cyclohexyl, and m is 1 to 100:

—H  (a)

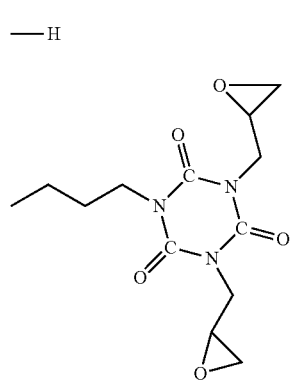
(b-i)

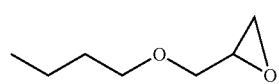
(b-ii)

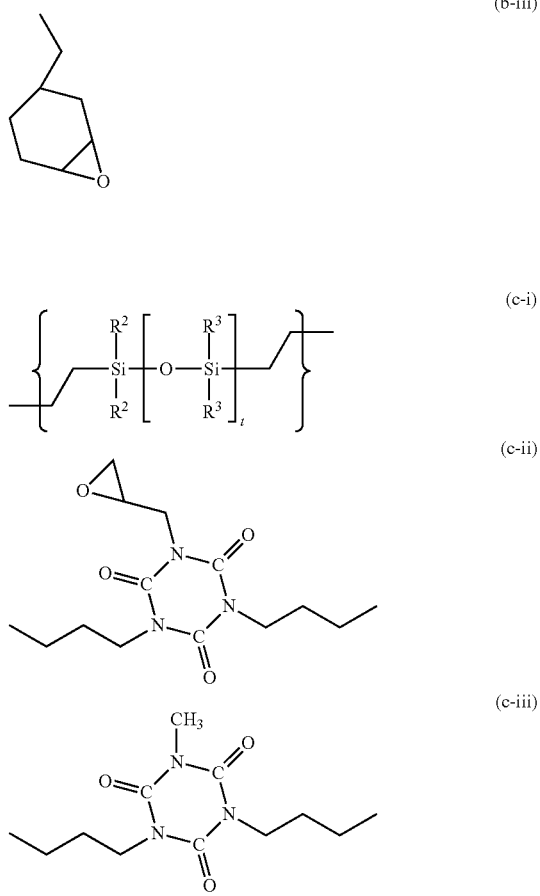

wherein, in formula (c-i), $R^2$ and $R^3$ are each independently a group selected from alkyl having 1 to 4 carbons, cyclopentyl, cyclohexyl and phenyl, and t is the number of repetitions of —OSi($R^3$)$_2$—, and is a mean value satisfying 1 to 100:

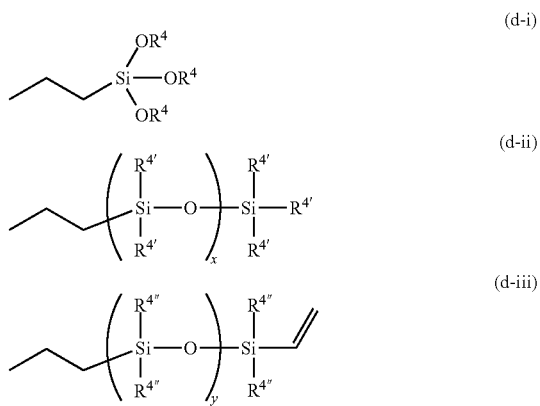

wherein, in formulas (d-i) to (d-iii), $R^4$, $R^{4'}$ and $R^{4''}$ are each independently a group selected from methyl, ethyl, butyl and isopropyl, x is the number of repetitions of —OSi($R^{4'}$)$_2$—, and is a mean value satisfying 1 to 20, and y is the number of repetitions of —OSi($R^{4''}$)$_2$—, and is a mean value satisfying 1 to 20.

2. The compound comprising the silsesquioxane skeleton including as the essential component the isocyanuric ring skeleton and the epoxy group, and having the SiH-group residue according to claim 1, obtained by allowing a hydrosilylation addition reaction of (A) and (B), and when necessary (C) and also (D):
(D) a compound having an aliphatic unsaturated group and an alkoxysilyl group, a trialkylsilyl group or a silyl group having a vinyl group.

3. A thermosetting resin composition containing (I) to (IV) below:
(I) a reaction product of double-decker silsesquioxane and organopolysiloxane, and thermosetting resin having an SiH group or both an SiH group and an alkenyl group;
(II) thermosetting resin being an organosiloxane compound that has two or more alkenyl groups and may include a silsesquioxane skeleton;
(III) the compound according to claim 1 as an adhesion-imparting agent; and
(IV) a Pt catalyst.

4. The thermosetting resin composition according to claim 3, wherein the thermosetting resin (I) is a compound represented by formula (I) below:

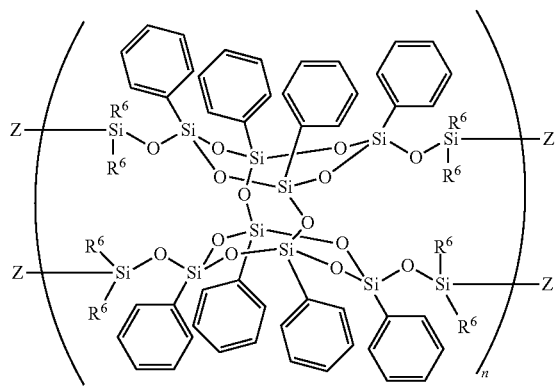

(I)

wherein, in formula (I), Z is each independently a group represented by formula (Z-i), formula (Z-ii) or formula (Z-iii) below, and with regard to the number of groups per one molecule of the compound represented by formula (I) (per one molecule on average of the compound being a mixture of compounds in which a ratio of the group represented by formula (Z-i), a ratio of the group represented by formula (Z-ii) and a ratio of the group represented by formula (Z-iii) are different), in the case where the number of groups represented by formula (Z-i) is taken as e, the number of groups represented by formula (Z-ii) is taken as f, and the number of groups represented by formula (Z-iii) is taken as g, expressions: $e+2f+g=4$, $1.0 \le e \le 3.0$, $0 \le 2f \le 2.0$, and $0 \le g \le 2.0$ hold; and $R^6$ is each independently a group selected from alkyl having 1 to 4 carbons, cyclopentyl and cyclohexyl, and n is 1 to 100:

—H  (Z-i)

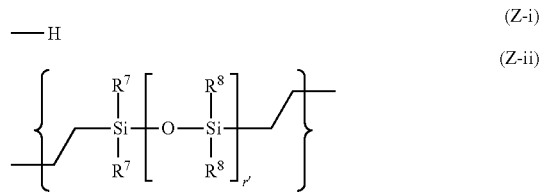

(Z-ii)

wherein, in formula (Z-ii), $R^7$ and $R^8$ are each independently a group selected from alkyl having 1 to 4 carbons, cyclopentyl, cyclohexyl and phenyl, r' is the number of repetitions of —OSi($R^8$)$_2$—, and r' is a mean value satisfying 2 to 100:

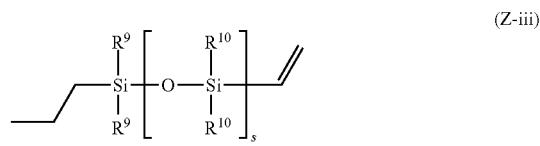

(Z-iii)

wherein, in formula (Z-iii), $R^9$ and $R^{10}$ are each independently a group selected from alkyl having 1 to 4 carbons, cyclopentyl, cyclohexyl and phenyl, s is the number of repetitions of —OSi($R^{10}$)$_2$—, and s is a mean value satisfying 2 to 50.

5. The thermosetting resin composition according to claim 3, containing the thermosetting resin (I) in a ratio of 40 to 95% by mass, the thermosetting resin (II) in a ratio of 0.1 to 50% by mass, the compound (III) in a ratio of 0.01 to 15.0% by mass, and the Pt catalyst (IV) in a ratio of 0.0001 ppm to 10 ppm, based on the total amount of the thermosetting resin composition.

6. The thermosetting resin composition according to claim 3, wherein at least one of silica or a phosphor is further dispersed thereinto.

7. A hardened material, obtained by hardening the thermosetting resin composition according to claim 3.

8. A coating film, obtained by hardening the thermosetting resin composition according to claim 3.

9. A composition for an optical semiconductor, containing the thermosetting resin composition according to claim 3.

10. An optical semiconductor device, comprising the composition for the optical semiconductor according to claim 9 as a sealing agent.

* * * * *